United States Patent

Kim et al.

[11] Patent Number: 5,461,026
[45] Date of Patent: Oct. 24, 1995

[54] PYRIDINE SULFONYL UREA DERIVATIVES

[75] Inventors: Dae-Whang Kim; Hae Sung Chang; Jae Wook Ryu; In Ho Jo, all of Daejeon, Rep. of Korea

[73] Assignee: Korea Research Institute of Chemical Technology, Daejeon, Rep. of Korea

[21] Appl. No.: 107,816

[22] PCT Filed: Feb. 25, 1992

[86] PCT No.: PCT/KR92/00005

§ 371 Date: Nov. 29, 1993

§ 102(e) Date: Nov. 29, 1993

[87] PCT Pub. No.: WO92/14728

PCT Pub. Date: Sep. 3, 1992

[30] Foreign Application Priority Data

Feb. 25, 1991 [KR] Rep. of Korea .................. 91-3014

[51] Int. Cl.$^6$ ................ C07D 401/12; C07D 401/14; A01N 43/54
[52] U.S. Cl. ............ 504/215; 544/319; 544/320; 544/321; 544/324; 544/327; 544/331; 544/333; 544/122; 544/123
[58] Field of Search ............... 504/215; 544/319, 544/320, 321, 324, 327, 331, 333, 122, 123

*Primary Examiner*—John M. Ford
*Attorney, Agent, or Firm*—Kenyon & Kenyon

[57] ABSTRACT

The present invention relates to novel pyridinesulfonylurea derivatives, having a herbicidal activity, which is described in the following structure of general formula (I)

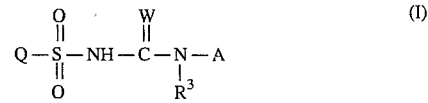

wherein, Q is Q-1, Q-2, Q-3 or Q-4 as follows;

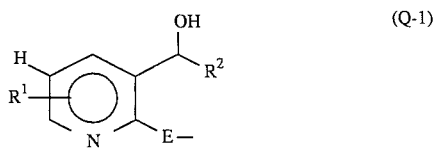

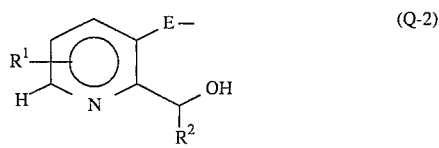

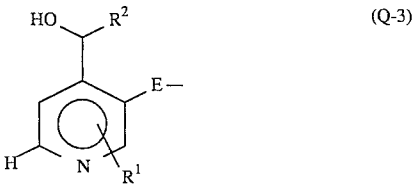

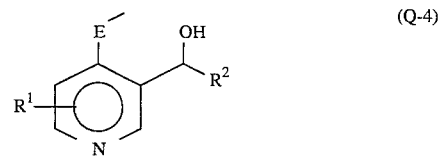

E is single bond or $CH_2$
$R^2$ is $C_1$–$C_6$ alkyl substituted with 1 to 3 halogens;
$R^1$, $R^3$, W and A are defined in the claims; and these may be an agriculturally suitable salt.

33 Claims, No Drawings

PYRIDINE SULFONYL UREA DERIVATIVES

This application is a 371 of PCT/KR92/0005, filed Feb. 25, 1992.

TECHNICAL FIELD

The present invention relates to novel pyridine sulfonyl urea derivatives having agriculturally suitable for herbicidal activity.

BACKGROUND OF THE INVENTION

It is publicly well known that sulfonyl urea derivatives have a herbicidal activity. Here are the formulas for the sulfonyl ureas.

1) U.S. Pat. No. 4,332,611 discloses the compound having the following formula

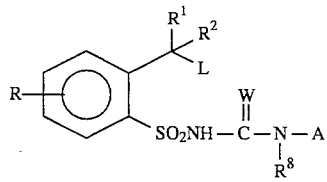

wherein,
L is OH,

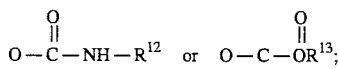

R is H, F, Cl, Br, $NO_2$, $CF_3$ or $C_1$–$C_3$ alkyl or alkoxy;
$R^1$ is H or $C_1$–$C_4$ alkyl;
$R^2$ is H or $CH_3$;
$R^8$ is H, $CH_3$ or $OCH_3$;
A is pyrimidine or triazine.

2) U.S. Pat. No. 4,786,314 discloses the compound having the following formula

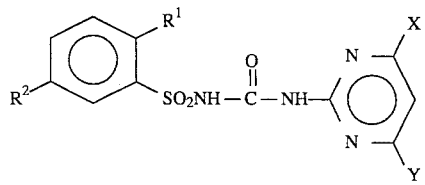

wherein,
$R^1$ is F, Cl, Br, $C_1$–$C_4$ alkyl, OH, alkoxy, alkylthio or $C_1$–$C_2$ alkyl substituted with phenyl group;
$R^2$ is —CHR—CN etc.

3) U.S. Pat. No. 4,838,926 discloses the compound having the following formula

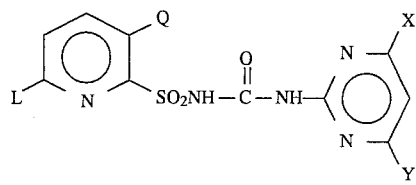

wherein,
Q is $C_1$–$C_4$ alkyl substituted with $R^2$;
$R^2$ is $OR^3$,

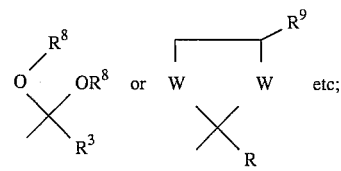

$R^3$ is H, $C_1$–$C_4$ alkyl;
L is

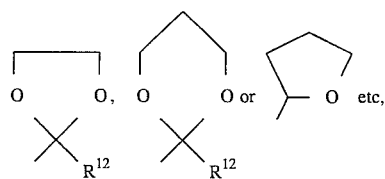

$R^{12}$ is H or $CH_3$.

4) European Patent No. 125,205 discloses the compound having the following formula

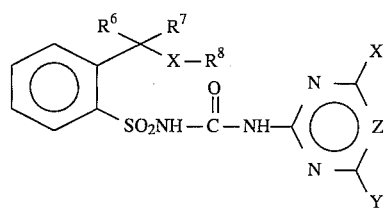

wherein,
$R^6$ is H, alkyl or F;
$R^7$ is H or $CH_3$;
W is O or S;
$R^8$ is haloalkyl or alkoxyalkyl.

5) U.S. Pat. No. 4,348,220 discloses the compound having the following formula

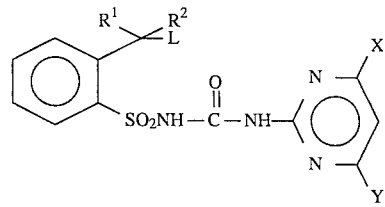

wherein,
L is $OR^9$;
$R^1$ is H or $C_1$–$C_4$ alkyl;

$R^2$ is H or $CH_3$;
$R^9$ is $C_1$–$C_6$ alkyl.

6) U.S. Pat. No. 4,822,403 discloses the compound having the following formula

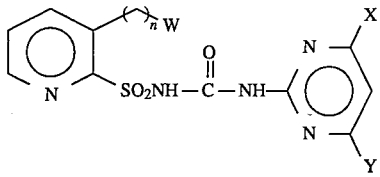

wherein,
n is 0 or 1;
W is $C_2$–$C_8$ alkenyl substituted with 1~3 F, Cl, Br, OH or alkoxy.

7) U.S. Pat. No. 4,662,933 discloses the compound having the following formula

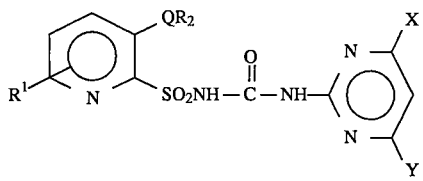

wherein,
Q is linear —$(CH_2)_n$-substituted with $C_1$–$C_3$ haloalkyl;
n is an integer of 1~3;
$R^2$ is SH, $N_3$ or SCN.

8) European Patent No. 13,480 discloses the compound having the following formula

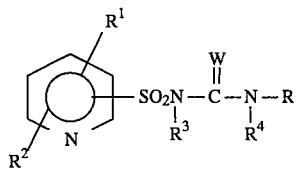

wherein,
$R^1$ is H, Cl, Br, F, alkyl, alkoxy, alkylthio or $CO_2R^5$.

9) U.S. Pat. Nos. 4,435,206 and 4,522,645 disclose 2-pyridine sulfonyl urea substituted with $R^1$ on 3-position, wherein R1 is H, Cl, Br, F, alkyl, alkoxy, alkylthio, $CO_2R^5$ or $SO_2NR^6R^7$.

10) U.S. Pat. No. 4,339,267 discloses 3-pyridine sulfonyl urea compound having the following formula

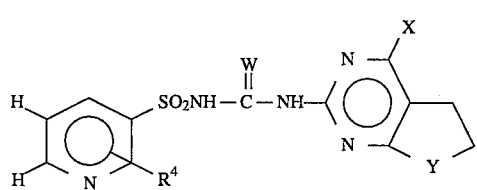

wherein,
$R^4$ is H, Cl, Br, F, alkyl, alkoxy, $NO_2$, $CO_2R^6$ or $SR^{13}$.

11) European Patent No. 30,433 disclose the compound having the following formula

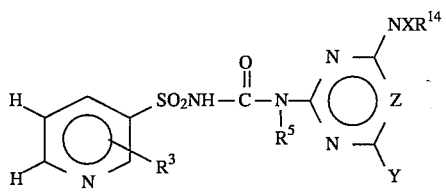

wherein,
$R^3$ is H, Cl, Br, F, $CO_2R^{11}$ or $SOnR^{12}$.

12) U.S. Pat. No. 4,456,469 discloses the compound having the following formula

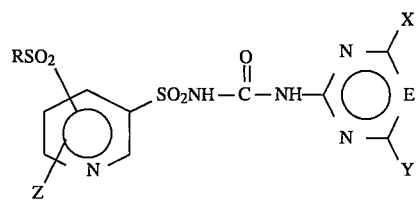

wherein,
R is alkyl, alkenyl, $CF_3$, $CHF_2$ or $CH_2CF_3$;
Z is H, F, Cl, Br or $SCH_3$.

13) U.S. Pat. No. 4,487,626 discloses 2,3- or 4-substituted pyridine sulfonyl urea compound having the following formula

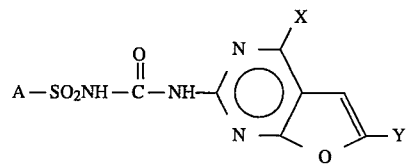

wherein,
A is

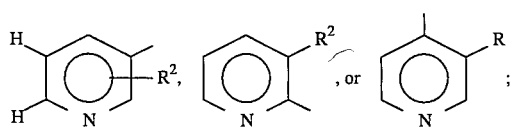

$R^2$ is H, Cl, Br, F, alkyl, alkoxy, $CO_2R^5$, $SOmR^6$, $SO_2NR^{18}R^{19}$ or $SO_2N(OCH_3)CH_3$.

14) U.S. Pat. Nos. 4,421,550 and 4,496,392, and European Patents No. 125,846/155,767/161,905/164,269/171,286 disclose pyridine sulfonyl urea substituted with Cl, Br, $SO_2R$ or $SO_2NR^1R^2$ on 2- or 3-position.

15) U.S. Pat. No. 4,549,898 discloses pyridine sulfonyl urea compound having the following formula

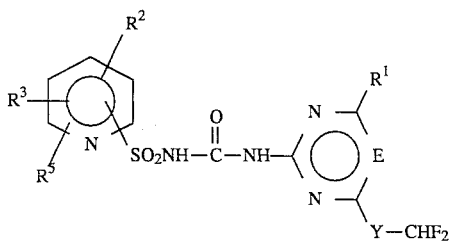

wherein, $R^2$ is H, alkyl, haloalkyl, halogen, $NO_2$, alkoxy,

$SO_2NR^6R^7$ or $SOnR$;

$R^3$ is H, halogen, alkyl, $OCH_3$, $NO_2$ or $CF_3$;

$R^5$ is H, $NO_2$, F, Cl, Br, $CH_3$, $CF_3$, SOn alkyl, $-CO_2R$ or alkoxy.

16) U.S. Pat. No. 4,579,583 discloses pyridine sulfonyl urea compound having the following formula

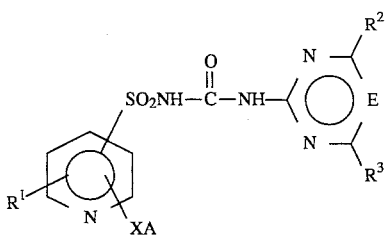

wherein,

X is O, S, SO or $SO_2$;

A is a optionally substituted alkyl, alkenyl or alkynyl;

$R^1$ is H, halogen, alkyl, alkoxy, haloalkyl, alkylthio or alkylsulfonyl.

17) U.S. Pat. No. 4,518,776 discloses a method for preparing the compound having the following formula

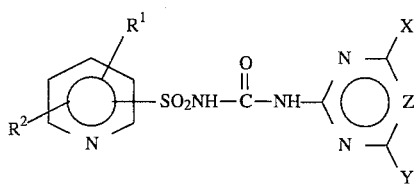

wherein, $R^1$ is alkylsulfonyl or dialkylamino sulfonyl group;

$R^2$ is H, halogen, $No_2$, $CF_3$, alkyl or alkoxy.

18) European Patent No. 101,670 discloses manufacture of pyridine sulfonyl urea having the following formula

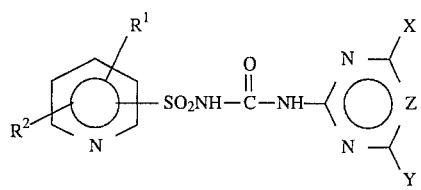

wherein, $R^1$ is Q alkyl or $SO_2N\ R^4R^5$;

Q is S or SOn;

$R^2$ is H, halogen, $CF_3$, $NO_2$, alkyl or alkoxy.

19) U.S. Pat. No. 4,521,597 discloses manufacture of pyridine sulfonyl urea compound having the following formula

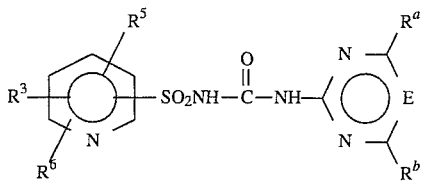

wherein, $R^3$ is H, F, Cl, Br, $NO_2$, $OCH_3$ or $CF_3$;

$R^5$ is SOm alkyl or $SO_2NR^8R^9$;

$R^6$ is H, F, $CH_3$ or $OCH_3$.

20) European Patent No. 184,385 discloses the compound having the following formula

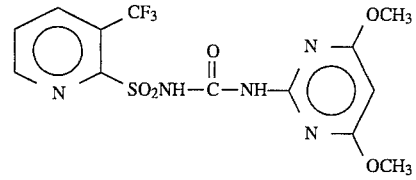

21) U.S. Pat. No. 4,747,870 discloses O-alkylcarbonyl pyridine sulfonyl urea compound, and U.S. Pat. No. 4,838,926 discloses O-substituted alkylpyridine urea compound. And, U.S. Pat. No. 4,747,337 discloses the compound having the following formula

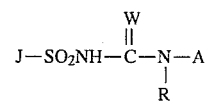

wherein,

J is

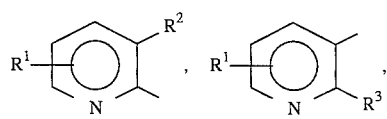

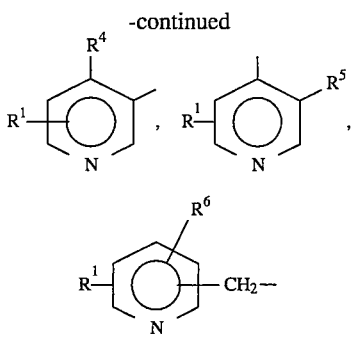

R¹ is H, alkyl, haloalkyl, halogen, NO₂, alkoxy, alkylthio or CN;

R²–R⁶ are alkylthio, alkylsulfinyl, alkylsulfonyl, cycloalkylthio, SO₂R⁸, SO₃R⁸N₃, CN, CH₂F, CHF₂, CH₂Cl, haloalkyl or PO(O alkyl)₂.

As the above patents, many sulfonyl urea herbicides have known until recently.

Even with these herbicides, more and more weeds develop immunity forwards these herbicides and cause undesirable vegetations. Thus, continuous research is in demand to develop more effective and newer for a good harvest.

Therefore, the object of the presentation is to invent a new pyridine sulfonyl urea derivative having a very prominent herbicidal activity with a good selectivity for various vegetations and agriculturally suitable herbicides for treatment of pre-emergence and/or post-emergence or plant growth regulants.

SUMMARY OF THE INVENTION

The present invention relates to novel pyridine sulfonyl urea derivatives having the following formula (I)

$$P-\overset{\overset{O}{\|}}{\underset{\underset{O}{\|}}{S}}-NH-\overset{\overset{W}{\|}}{C}-\underset{R^3}{N}-A \quad (I)$$

wherein,

P is P-1, P-2, P-3 or P-4 as follows;

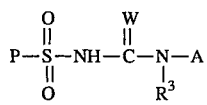   (P-1)

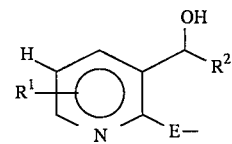   (P-2)

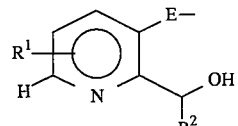   (P-3)

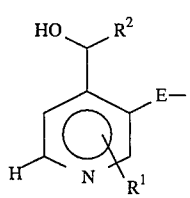   (P-4)

E is single bond or CH₂;

R¹ is H, C₁–C₃ alkyl, C₁–C₃ haloalkyl, halogen, CN, NO₂, C₁–C₃ alkoxy, C₁–C₃ haloalkoxy, SO₂NR′R″, C₁–C₃ alkylthio, C₁–C₃ alkylsulfinyl, C₁–C₃ alkylsulfonyl, SCH₂F, NH₂, NHCH₃, N(CH₃)₂, C₁–C₂ alkyl substituted with C₁–C₂ alkoxy, C₁–C₂ haloalkoxy, SH, SCH₃, CN or OH or CO₂R′″; and then R′ is H, C₁–C₄ alkyl, C₂–C₃ cyanoalkyl, methoxy or ethoxy; R″ is H, C₁–C₄ alkyl, C₃–C₄ alkenyl, or when taken together, connecting R′ and R″, —(CH₂)₃—, —(CH₂)₄—, —(CH₂)₅— or CH₂CH₂OCH₂CH₂—, may be formed;

R′″ is C₁–C₄ alkyl, C₃–C₄ alkenyl, C₃–C₄ alkynyl, C₁–C₄ alkyl substituted with 1~2 halogen or cyano groups, C₅–C₆ cycloalkyl, C₃–C₇ cycloalkylalkyl or C₂–C₄ alkoxyalkyl;

R² is C₁–C₆ alkyl substituted with 1~3 halogen;

R³ is H or CH₃;

W is O or S;

A is A1, A2, A3, A4, A5, A6 or A7 as following;

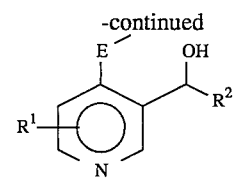   A1

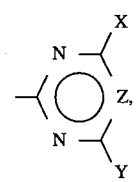   A2

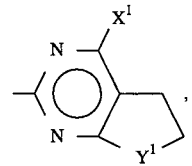   A3

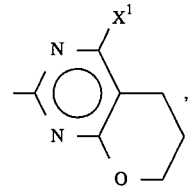   A4

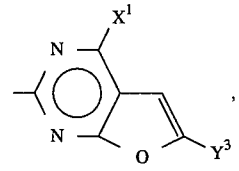   A5

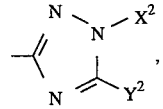

-continued

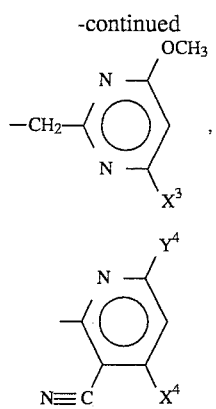  A6

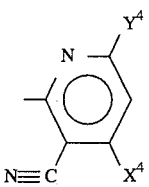  A7 wherein,

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogene, $C_2$–$C_5$ alkoxyalkyl, $C_2$–$C_5$ alkoxyalkoxy, amino, $C_1$–$C_3$ alkylamino, di($C_1$–$C_3$ alkyl)amino or $C_3$–$C_5$ cycloalkyl;

Y is H, $C_1$–$C_4$ alkyl, $C_1$–$C_4$ alkoxy, $C_1$–$C_4$ haloalkoxy, $C_1$–$C_4$ haloakylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_2$–$C_5$ alkylthioalkyl, $C_1$–$C_4$ haloalkyl, $C_2$–$C_4$ alkynyl, azido, cyano, $C_2$–$C_5$ alkylsulfinylalkyl, $C_2$–$C_5$ alkylsulfonylalkyl, $CH_2OH$, $C_3$–$C_5$ cycloalkyl, $C_3$–$C_5$ cycloalkoxy, $C_3$–$C_4$ alkynyloxy,

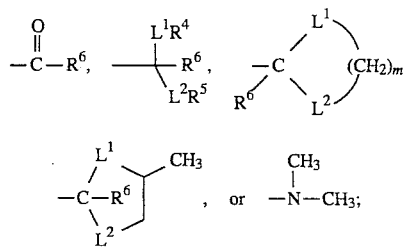

m is 2 or 3;
$L^1$ and $L^2$ are independently O or S;
$R^4$ and $R^5$ are independently $C_1$–$C_2$ alkyl;
$R^6$ is H, or $CH_3$;
Z is CH, N, $CCH_3$ or $CC_2H_5$;
$Y^1$ is O or $CH_2$;
$X^1$ is $CH_3$, $OCH_3$, $OC_2H_5$ or $OCHF_2$;
$Y^3$ is H or $CH_3$;
$Y^2$ is $CH_3$, $CH_2CH_3$, $OCH_3$, $OCH_2CH_3$, $SCH_3$ or $SCH_2CH_3$;
$X^2$ is $CH_3$, $CH_2CH_3$, or $CH_2CF_3$;
$X^3$ is $CH_3$ or $OCH_3$;
$Y^4$ is $CH_3$, $OCH_3$, $OC_2H_5$, $CH_2OCH_3$ or Cl;
$X^4$ is $CH_3$, $OCH_3$, $OC_2H_5$, $CH_2OCH_3$ or Cl; and these may be an agriculturally suitable salt, and then, (1) if X is Cl, Br, F or I, Z is CH and Y is $OCH_3$, $OC_2H_5$, $NCH_3(OCH_3)$, $NH_2$, $NHCH_3$, $N(CH_3)_2$ or $OCHF_2$;
(2) if X or Y is $OCHF_2$, Z is CH;
(3) $X^4$ and $Y^4$ are not Cl simultaneously;
(4) if W is S, $R^3$ is H, A is $A_1$, Z is CH or N and, Y is $CH_3$, $OCH_3$, $OCH_2CH_3$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

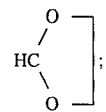

(5) if a number of total carbon atoms X and Y are more than 4, a number of carbon atoms of $R^2$ is 4 or less than 4.

DETAILED DESCRIPTION OF THE INVENTION

Among the definitions according to the present invention, the following terms have the following meanings;

a) "Alkyl" used ether alone or in compound word such as "alkylthio" or "haloalkyl" etc. denotes straight chain or branched alkyls such as methyl, ethyl, n-propyl, isopropyl or buthyl isomers.

b) "Alkoxy" denotes methoxy, ethoxy, n-propoxy, isopropoxy or buthoxy isomers.

c) "Alkenyl" denotes straight chain or branched alkenes, for example, vinyl, 1-prophenyl, 2-prophenyl, or buthenyl, pentenyl, hexenyl or heptenyl isomers etc.

d) "Alkynyl" denotes straight chain or branched alkynyl such as ethynyl, 1-propynyl, 2-propynyl, or buthynyl, pentynyl or hexynyl isomers.

e) "Halogen" used ether alone or in compound ward "halo" denotes chlorine, fluorine, bromine or Iodine.

A preferred group of pyridine sulfonyl urea derivatives having the formula shown as the below (I), in view of compounding of the polymer and herbicidal activity, wherein (1) $R^3$ is H, W or O;
(2) $R^1$ is H, F, Cl, $C_1$–$C_2$ alkyl, $C_1$–$C_2$ haloalkyl, $C_1$–$C_2$ alkoxy, $C_1$–$C_2$ haloalkoxy, $C_1$–$C_2$ alkylthio, $CH_2OCH_3$, or $CH_2SCH_3$;
(3) X is $CH_3$, $OCH_3$, $OCH_2CH_3$, Cl, F, Br, $OCHF_2$, $CH_2F$, $OCH_2CH_2F$, $OCH_2CHF_2$, $OCH_2CF_3$, $CF_3$, $CH_2Cl$ or $CH_2Br$;

Y is H, $C_1$–$C_3$ alkyl, $OCH_3$, $OCH_2CH_3$, $CH_2OCH_3$, $NHCH_3$, $NCH_3(OCH_3)$, $N(CH_3)_2$, $CF_3$, $SCH_3$, $OCH_2CH=CH_2$, $OCH_2C\equiv CH$, $CH_2OC_2H_5$, $OCH_2CH_2OCH_3$, $CH_2SCH_3$, $OCHF_2$, $SCHF_2$, cyclopropyl, $C\equiv CH$, or $C\equiv C-CH_3$;
(4) $R^2$ is $CH_2F$, $CHF_2$, $CHFCl$, $CH_2Cl$, $CH_2Br$, $CHFCH_3$, $CH_2CH_2F$, $CH_2CH_2Cl$, $CHClCH_3$, $CHCl_2$, $CHFCH_2F$, $CHClCH_2Cl$, $CHFCH_2Cl$ or $CH_2CF_3$;
(5) A is $A_1$, and Z is CH;
X is $CH_2OCH_3$, $OCH_2CH_3$, Cl or $OCHF_2$;
Y is $CH_3$, $C_2H_5$, $OCH_3$, $CH_2OCH_3$, $CH(OCH_3)_2$, $OCHF_2$, $NHCH_3$, $N(Me)_2$ or cyclopropyl, and $R^1$ is H, $CH_3$, $OCH_3$ or Cl.

The novel compounds having the above formula(I) according to the present invention have a very strong herbicidal activity and a good selectivity for a useful vegetation.

The compounds of the present invention can be prepared by reactions as described in herein below.

The compound of general formula(I) can be obtained by hydrolyzing the compound of following formula(II) with alkali under water, organic solvent or the mixture solution thereof.

(Method 1)

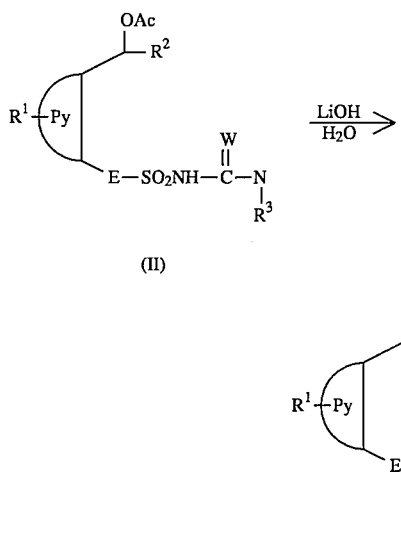

(II)

(I)

wherein,

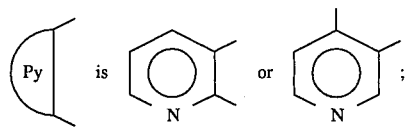

and $R^1$ is not para substituent of sulfonyl urea.

In the above reaction scheme of Method 1, Ac is acetyl group, but it may be a protecting group easily dissolved by acid, alkali or others. In order to hydrolyze the above Ac group, alkali base such as NaOH, KOH, LiOH, $Na_2CO_3$, $K_2CO_3$, etc., preferably LiOH, may be used.

The above reaction of Method I is carried out under water or organic solvent, and also a mixture of water with unreacting solvent such as methanol, ethanol, acetone or THF etc., or solvent alone.

The hydrolysis in the reaction occurs at the temperature of 0°~80° C. and the reaction time of 1~24 hours, and then the obtained product may be easily seperated by acidifying with HCl water solution.

As an other process, after acidifying, the obtained product is extracted with methylene chloride, ethyl acetate, etc. then concentrated/crystallized to obtain the final product. If necessary, a pure product can be obtained by purification to column chromatograph.

The compound of the above formula(I) according to the present invention can be prepared by reaction the compound having the following formula(III) with alkali at the temperature of 25°~40° C. (Method 2)

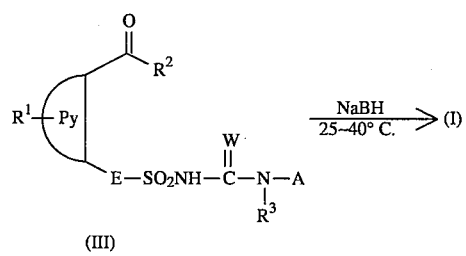

(III)

The reaction of Method 2 may be preferably carried out under alkali such as NaOH etc. of a small quantity. The product may be seperated as the same with the above Method I.

On the other hand, the compound of the above formula(II) used in the present invention can be prepared by reacting the compound of following formula(IV) with formula(V).

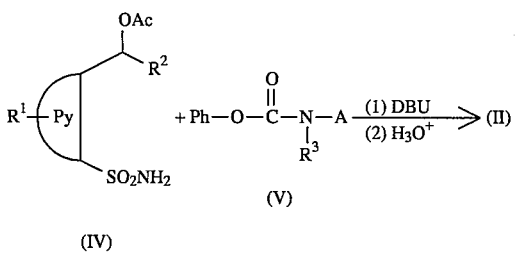

(IV)                (V)

The above reaction may be carried out in solvent of dioxane or acetonitryl under in active atmosphere at the temperature of 25° C. for 1~2 hours. The obtained product may be easily seperated by acidifying with HCl water solution.

As another process, after acidifying, the obtained product is extracted with solvent of methylene chloride or ethylacetate and dried/evaporated to obtain final product.

Also, the compound of the above formula(III) used in the present invention can be obtained by the method disclosed on U.S. Pat. No. 4,370,480.

Meanwhile, phenylcarbamate(V) used for preparing the above formula(II) can be composed by reacting heterocyclic amine of $A-NHR^3$ of formula(VI) with diphenylcarbonate or phenylchloroformate under a base such as NaH, pyridine, $K_2CO_3$, etc. after adding of dimethyl aminopyridine(D-MAP), and then the reacting mixture is stirred in a solvent such as THF etc. at 25°~65° C. for 12~36 hours.

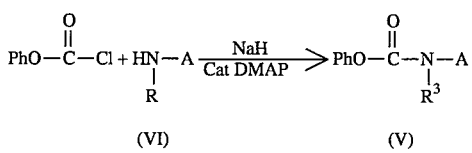

(VI)                (V)

The compound of the formula(IV) can be prepared by treating N-t-buthylsulfonamide(IV) with an acid such as trifluoroacetic acid(TFA), polyphosphoric acid(PPA) or p-toluensulfonic acid(p-TSA).

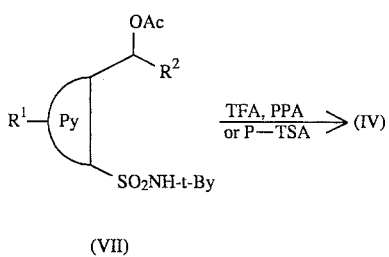

(VII)

In order to prepare the above formula(IV), the compound of the above formula(VII) is added in trifluoroacetic acid (about 0.3M) of an excess. And they are stirred at about 25° C. for 1~72 hours to easily carry out the reaction.

Then, a volatile metter is evaporated under vacuum and the residue is crystallized in a solvent such as diethylether, 1-chlorobutane, ethylacetate, etc. to isolate the product, sulfonamide of formula(IV). This reaction shall be referenced by J. D. Catt and W. L. Matier, J. Org. Chem., 38, 1974(1973).

Also, sulfonamide of the above formula(IV) can be prepared by the following reaction process.

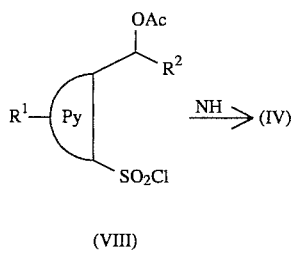

(VIII)

As the above reaction, the compound of formula(IV) can be obtained by adding ammonia of a great quantity in sulfonylchloride, preferably temperature below −10° C., and as a solvent such as ethylacetate, ether, THF, methylene chloride etc. may be used.

On the other hand, the compound of the above formula(VII) can be prepared by the following reaction process.

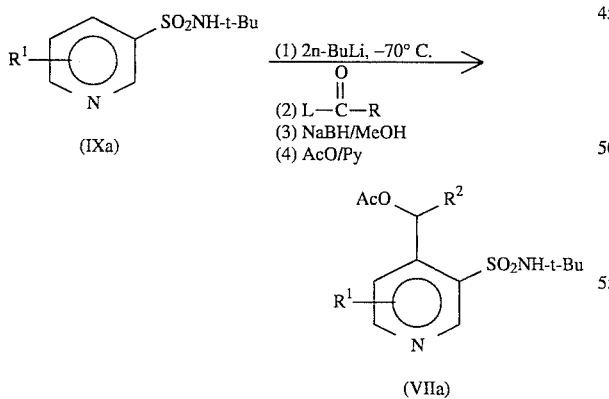

(VIIa)

(wherein, L is H, $OC_2H_5$, $NMe_2$ or $N(OCH_3)CH_3$)

In the above reaction, n-butyl lithium of 2 equivalents is added in the compound of the above formula(IXa) in order to lithiation; and thereafter aldehyde, ester or amide taking ketone compound, or N,O-dimethyl hydroxyamide is added; if aldehide is used, hydroxy compound is produced directly; and then the compound of formula(VIIa) can be prepared by acylation under pyridine; if the compound of $R^2CHO$ is not obtained, after obtaining ketone compound then hydroxy compound be obtained by reduction of that with $NaBH_4$; and then the compound of formula(VIIa) is easily obtained by acylation.

This reaction process is able to be carried out by a skill person in this technical field.

Also, in the case of 2-pyridine sulfonamide, the compound of formula(VIIa) can be obtained by the same with the above reaction process.

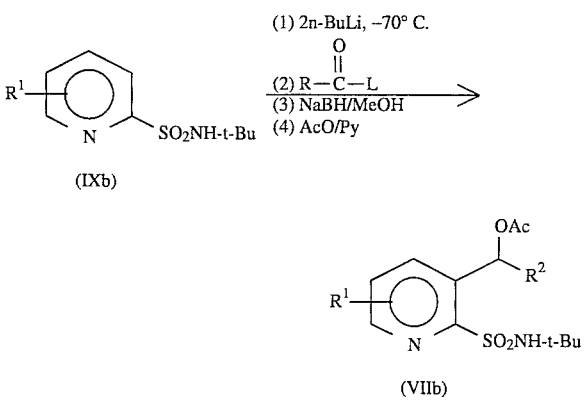

(VIIb)

Also, sulfonamide can be obtained by reacting sulfonylchloride(VIII) with t-$BuNH_2$ as the following reaction scheme.

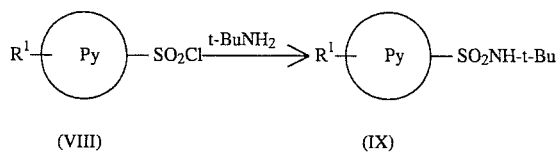

(VIII)         (IX)

In the above reaction, sulfonylchloride can be prepared by the method of U.S. Pat. Nos. 4,456,469 or 4,740,233 as following scheme.

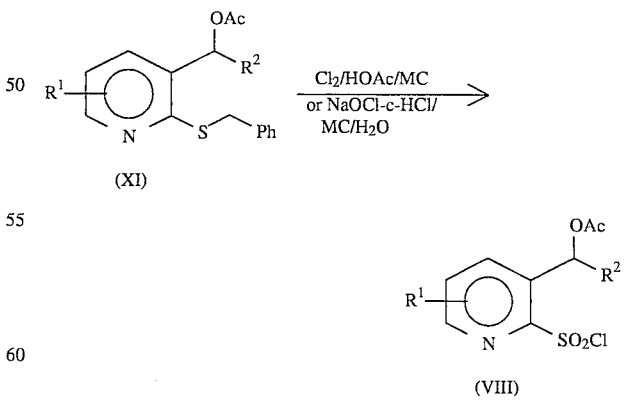

(VIII)

Wherein, the reaction may be preferably carried out at low temperature of 10° C. and below it.

The compound of formula(XII) can be prepared by the following reaction scheme.

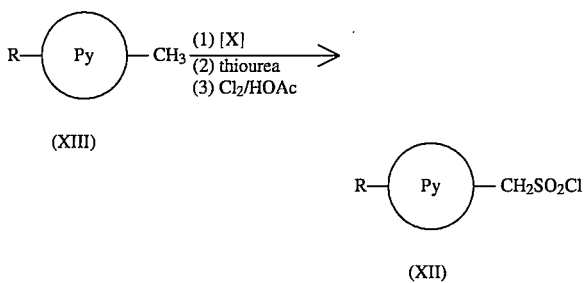

This reaction is disclosed in U.S. Pat. No. 4,420,325.

The compound of formula(XI) can be prepared by the following reaction process.

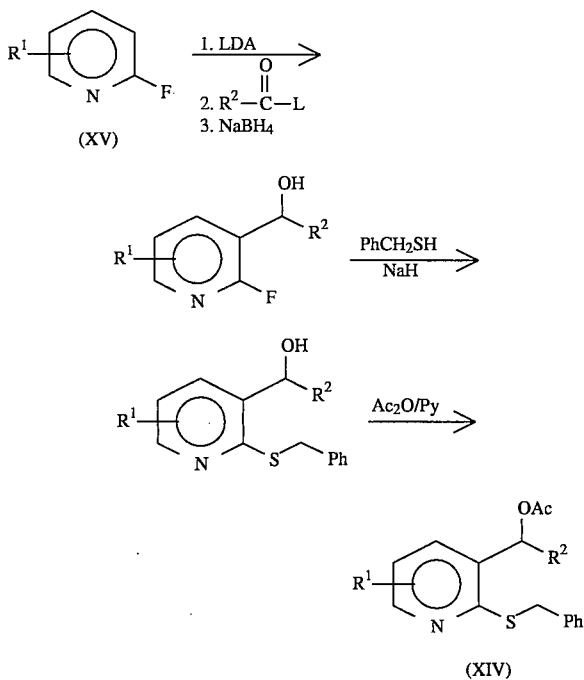

In the reaction process, metalation reaction using LDA of 2-fluoropyridine may be carried out by the method of T, Gungor, F. Marsais and G. Gueguiner, J. Organomet Chem., 1981, 215, 139–150, and thereafter acylation by a common method.

Halopyridin of the above formula(XV) is transformed to sulfide of formula(XIV) by reating with a mercaptane under a base. This reaction is disclosed by U.S. Pat. No. 4,456,469.

Lithiation of fluoropyridine or transform reaction to sulfonyl chloride which is consisted of transformation to sulfide from fluoropyridin and its chloridization, can be easily carried out by the method of U.S. Pat. No. 4,774,337.

The compound of formula(XVI) can be composed by the following reaction process.

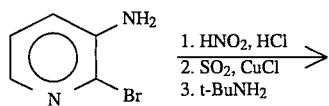

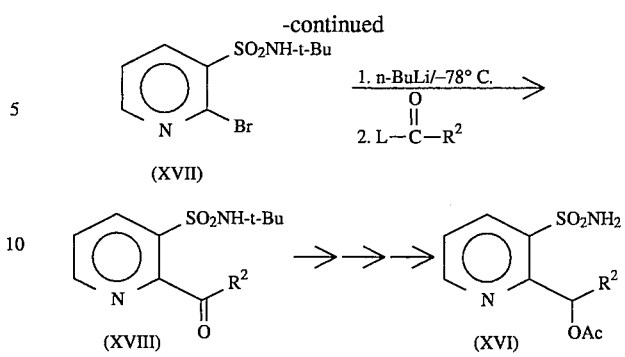

It was well-known the reaction which is transformed aminopyridine to sulfonamide as preferably reference of U.S. Pat. No. 4,456,459. Also, exchange reaction to metal halogen from bromosulfonamide was well-known, and thereafter sulfonamide(XVI) may be prepared by the above reaction scheme for manufacturing the above formula(VIIa).

The heterocyclic amine compound of formula(VI) may be prepared by a skill person in this technical field from a method disclosed in literatures or the simple transformation of it.

For example, European Patent Application No. 84,244 (Pub. Jul. 27, 1983) and J. Am. Chem. Soc., 69,3072(1947) of W. Braker et al. disclose a method for preparing aminopyrimidine and triazine substituted with acetyl group. European Patent No. 72,347 and U.S. Pat. Nos. 4,443,243/ 4,487,915 disclose a method for preparing aminopyrimidine and/or triazine substituted with haloalkyl such as $OCHF_2$, $SCHF_2$, $OCH_2CH_2F$ and $OCH_2CF_3$ etc. and haloalkylthio as a substitution group.

European Patent No. 108,708, U.S. Pat. Nos. 4,515,626/ 4,600,428 disclose cyclo propylpyrimidine and/or triazine substituted with alkyl, haloalkyl, alkoxy, haloalkoxy, alkylamino, dialkylamio and alkoxyalkyl group etc.

European Patent No. 15,863 discloses a method for preparing the compound of the above formula(VI), as 5,6-dihydro-puro[2,3-d] pyrmidine-2-amine compounds and cyclopenta[d]pyrimidine-2-amine compounds which A is $A_2$; and 6,7-dihydro-5H-pyrano-[2,3-d] pyrimidine-2-amine compound which A is $A_3$.

European Patent No. 46,677 discloses puro[2,3-d]pyridine-2-amine compounds which A is $A_4$ in the formula(VI), and European Patent No. 73,562 discloses heterocyclic compounds which A is $A_5$.

The compound of formula(VI) which A is $A_6$ can be prepared by European Patent No. 94,260. The compound of formula(VI) which A is $A_7$, can be manufactured by the method of European Patent No. 125,864.

Common methods for preparing aminopyridine and triazine compounds is arranged on the following literatures: "The chemistry and Heterocyclic compounds", Series, Interscience Publishers, Inc., New York and London; "Pyrimidines", Vol. 16, D. J. Brown Ed.; "S-Triazines and Derivatives", Vol. 13, E. M. Smolin and L. Rapaport. Composition of triazine compounds is disclosed in F. C. Schaefer, U.S. Pat. No. 3,154,547 and K. R. Huffman and F. C. Schaefer, J. Org. Chem., 28, 1812(1963).

On the other hand, salts of the compound of the above formula(I) also is useful as herbicide, and they can be prepared by various methods according to prior art.

For example, metal salts of the compound can be prepared by reacting the above formula(I) compound with strong basic anion, e.g. alkali or alkaline earth metal solution having hydroxyl group alkoxyde or carbonate, and also quaternary amine salt alike.

A salt of the formula(I) compound may also be obtained by cation exchange. The cation exchange can be manufactured by directly reacting solution containing cation for exchange with solution of salt of formula(I), for example aqueous solution of alkali metal or quaternary amine salt.

This method is useful when the desirable salt is water soluble, especially sodium, potassium or calcium salt.

The above manufacturing methods is summarized briefly, but the method can be carried out easily by a skill person in this technical field of composition and manufacturing for sulfonyl urea or organic composition.

The compounds of said general formula(I) of the present invention specify the following Table;

TABLE 1

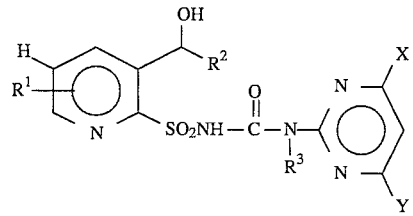

| $R^1$ | $R^2$ | $R^3$ | X | Y | mp (°C.) |
|---|---|---|---|---|---|
| H | $CH_2F$ | H | $OCH_3$ | $OCH_3$ | 119–120 |
| H | $CH_2F$ | H | $CH_3$ | $OCH3$ | 151–152 |
| H | $CH_2F$ | H | $CH_3$ | $CH_3$ | 169–170 |
| H | $CH_2F$ | H | Cl | $OCH_3$ | 138–139 |
| H | $CH_2F$ | H | Br | $OCH_3$ | |
| H | $CH_2F$ | H | H | $CH_3$ | |
| H | $CH_2F$ | H | $OHC_3$ | H | |
| H | $CH_2F$ | H | $OCH_3$ | $CH_2OC_2H_5$ | |
| H | $CH_2F$ | H | $OCF_2H$ | $OCH_3$ | |
| H | $CH_2F$ | H | $OCH_3$ | $CH(OCH_3)_2$ | |
| H | $CH_2F$ | H | $CH_3$ | $OC_2H_5$ | |
| H | $CH_2F$ | H | $CH_3$ | $CH_2OCH_3$ | |
| H | $CH_2F$ | H | $OCH_3$ | $CH_2OCH_3$ | |
| H | $CH_2F$ | H | $C_2H_5$ | $OCH_3$ | |
| H | $CH_2F$ | H | $OC_2H_5$ | $OCH_3$ | |
| H | $CH_2F$ | H | $OCH_2CF_3$ | $OCH_3$ | |
| H | $CH_2F$ | H | $CF_3$ | $OCH_3$ | |
| H | $CH_2F$ | H | $CH_2F$ | $OCH_3$ | |
| H | $CH_2F$ | H | $CH_2Cl$ | $OCH_3$ | |
| H | $CH_2F$ | H | $CH_2Br$ | $OCH_3$ | |
| H | $CH_2F$ | H | F | $OCH_3$ | |
| H | $CH_2F$ | H | I | $OCH_3$ | |
| H | $CH_2F$ | H | $OCH_2CH_2F$ | $OCH_3$ | |
| H | $CH_2F$ | H | $OCH_2CH_2CF_3$ | $OCH_3$ | |
| H | $CH_2F$ | H | $OCH_2CHF_2$ | $CH_3$ | |
| H | $CH_2F$ | H | $OCH_2CF_3$ | $CH_3$ | |
| H | $CH_2F$ | H | Cl | $OC_2H_5$ | 133–135 |
| H | $CH_2F$ | H | $OC_2H_5$ | $NHCH_3$ | |
| H | $CH_2F$ | H | $OC_2H_5$ | $CH_2SCH_3$ | |
| H | $CH_2F$ | H | $OCF_2H$ | $CH_3$ | |
| H | $CH_2F$ | H | Cl | $OCF_2H$ | |
| H | $CHFCH_3$ | H | $OCH_3$ | $OCH_3$ | 132–134 |
| H | $CHFCH_3$ | H | $CH_3$ | $OCH_3$ | 135–137 |
| H | $CHFCH_3$ | H | $CH_3$ | $CH_3$ | 146–148 |
| H | $CHFCH_3$ | H | Cl | $OCH_3$ | 119–121 |
| H | $CHFCH_3$ | H | Br | $OCH_3$ | |
| H | $CHFCH_3$ | H | $CH_3$ | H | |
| H | $CHFCH_3$ | H | $OCH_3$ | H | |
| H | $CHFCH_3$ | H | $OCH_3$ | $CH_2OC_2H_5$ | |
| H | $CHFCH_3$ | H | $OCF_2H$ | $OCH_3$ | |
| H | $CHFCH_3$ | H | $OCH_3$ | $CH(OCH_3)_2$ | |
| H | $CHFCH_3$ | H | $CH_3$ | $OC_2H_5$ | |
| H | $CHFCH_3$ | H | $CH_3$ | $CH_2OCH_3$ | |
| H | $CHFCH_3$ | H | $OCH_3$ | $CH_2OCH_3$ | |
| H | $CHFCH_3$ | H | $OCH_3$ | $C_2H_5$ | |
| H | $CHFCH_3$ | H | $OC_2H_5$ | $OCH_3$ | |
| H | $CHFCH_3$ | H | $OCH_2CF_3$ | $OCH_3$ | |
| H | $CHFCH_3$ | H | $CF_3$ | $OCH_3$ | |
| H | $CHFCH_3$ | H | $CH_2F$ | $OCH_3$ | |
| H | $CHFCH_3$ | H | $CH_2Cl$ | $OCH_3$ | |
| H | $CHFCH_3$ | H | $CH_2Br$ | $OCH_3$ | |
| H | $CHFCH_3$ | H | F | $OCH_3$ | |
| H | $CHFCH_3$ | H | I | $OCH_3$ | |
| H | $CHFCH_3$ | H | $OCH_2CH_2F$ | $OCH_3$ | |
| H | $CHFCH_3$ | H | $OCH_2CH_2CF_3$ | $OCH_3$ | |
| H | $CHFCH_3$ | H | $OCH_2CHF_2$ | $CH_3$ | |
| H | $CHFCH_3$ | H | $OCH_2CF_3$ | $CH_3$ | |

TABLE 1-continued

Structure: pyridine with OH-CHR² group, SO₂NH-C(=O)-N(R³)- linked to pyrimidine bearing X and Y; R¹ on pyridine ring.

| R¹ | R² | R³ | X | Y | mp (°C.) |
|---|---|---|---|---|---|
| H | CHFCH₃ | H | Cl | OC₂H₅ | 112–113 |
| H | CHFCH₃ | H | OC₂H₅ | NHCH₃ | |
| H | CHFCH₂CH₃ | H | OCH₃ | CH₃ | 124–125 |
| H | CHFCH₂CH₃ | H | OCH₃ | OCH₃ | 120–121 |
| H | CHFCH₂CH₃ | H | Cl | OCH₃ | 114–115 |
| H | CH₂F | H | NH₂ | OC₂H₅ | |
| H | CH₂F | H | n-C₃H₇ | OCH₃ | |
| H | CH₂F | H | NHCH₃ | OCH₃ | |
| H | CH₂F | H | OCH₃ | SCH₃ | |
| H | CH₂F | H | OCH₃ | SCF₂H | |
| H | CH₂F | H | OCH₃ | OCH₂CCH | |
| H | CH₂F | H | OCH₃ | OCH₂CH=CH₂ | |
| H | CH₂F | H | OCH₃ | CCH | |
| H | CH₂F | H | OCH₃ | N(CH₃)₂ | |
| H | CH₂F | H | OCH₃ | cyclopropyl | |
| H | CH₂F | H | OCH₃ | NH₂ | |
| H | CH₂F | H | OCH₃ | CF₃ | |
| H | CH₂F | H | OCH₃ | OCH₂CH₂OCH₃ | |
| H | CH₂F | H | OCH₃ | CH₂SCH₃ | |
| H | CH₂F | H | OCH₃ | CHO | |
| H | CH₂F | H | OCH₃ | COCH₃ | |
| H | CH₂F | H | OCH₃ | CH(SCH₃)OC₂H₅ | |
| H | CH₂F | H | OCH₃ | C(CH₃)(SCH₃)₂ | |
| H | CH₂F | H | OCH₃ | C(SC₂H₅)₂ | |
| H | CH₂F | H | OCH₃ | 1,3-dioxolan-2-yl | |
| H | CH₂F | H | OCH₃ | 2-methyl-1,3-oxathiolan-2yl | |
| H | CH₂F | H | OCH₃ | 1,3-oxathian-2-yl | |
| H | CH₂F | H | OCH₃ | 2-methyl-1,3-dithian-2-yl | |
| H | CH₂F | H | OCH₃ | 4-methyl-1,3-dioxolan-2-yl | |
| H | CH₂F | H | OCH₃ | 2-4-dimethyl-1,3-dithiolan-2-yl | |
| H | CH₂F | H | OCH₃ | N(OCH₃)(CH₃) | |
| H | CH₂F | H | OCH₃ | CCCH₃ | |
| H | CH₂F | H | OCH₃ | C₂H₅ | |
| H | CH₂F | H | OCH₃ | OCF₂Br | |
| H | CH₂CH₂F | H | OCH₃ | OCH₃ | |
| H | CH₂CH₂F | H | CH₃ | OCH₃ | |
| H | CH₂CH₂F | H | CH₃ | CH | |
| H | CH₂CH₂F | H | Cl | OCH₃ | |
| H | CH₂CH₂F | H | Br | OCH₃ | |
| H | CH₂CH₂F | H | CH₃ | H | |
| H | CH₂CH₂F | H | OCH₃ | H | |
| H | CH₂CH₂F | H | OCH₃ | CH₂OC₂H₅ | |
| H | CH₂CH₂F | H | OCF₂H | OCH₃ | |
| H | CH₂CH₂F | H | OCH₃ | CH(OCH₃)₂ | |
| H | CH₂CH₂F | H | CH₃ | OC₂H₅ | |
| H | CH₂CH₂F | H | CH₃ | CH₂OCH₃ | |
| H | CH₂CH₂F | H | OCH₃ | CH₂OCH₃ | |
| H | CH₂CH₂F | H | OCH₃ | C₂H₅ | |
| H | CH₂CH₂F | H | OC₂H₅ | OCH₃ | |
| H | CH₂CH₂F | H | OCH₂CF₃ | OCH₃ | |
| H | CH₂CH₂F | H | CF₃ | OCH₃ | |
| H | CH₂CH₂F | H | CH₂F | OCH₃ | |
| H | CH₂CH₂F | H | CH₂Cl | OCH₃ | |
| H | CH₂CH₂F | H | CH₂Br | OCH₃ | |
| H | CH₂CH₂F | H | F | OCH₃ | |
| H | CH₂CH₂F | H | I | OCH₃ | |
| H | CH₂CH₂F | H | OCH₂CH₂F | OCH₃ | |
| H | CH₂CH₂F | H | OCH₂CH₂CF₃ | OCH₃ | |
| H | CH₂CH₂F | H | OCH₂CHF₂ | CH₃ | |
| H | CH₂CH₂F | H | OCH₂CF₃ | CH₃ | |
| H | CH₂CH₂F | H | Cl | OC₂H₅ | |
| H | CH₂CH₂F | H | OC₂H₅ | NHCH₃ | |

TABLE 1-continued

[Structure: pyridine with OH, R¹, R², SO₂NH-C(=O)-N(R³)- linked to pyrimidine with X and Y substituents]

| R¹ | R² | R³ | X | Y | mp (°C.) |
|---|---|---|---|---|---|
| H | CH₂CH₂F | H | OCH₃ | CH₂SCH₃ | |
| H | CH₂CH₂F | H | OCF₂H | CH₃ | |
| H | CH₂CH₂F | H | Cl | OCF₂H | |
| H | CH₂Cl | H | OCH₃ | OCH₃ | 135–137 |
| H | CH₂Cl | H | CH₃ | OCH₃ | 123–124 |
| H | CH₂Cl | H | CH₃ | CH₃ | 139–140 |
| H | CH₂Cl | H | Cl | OCH₃ | 136–137 |
| H | CH₂Cl | H | Br | OCH₃ | |
| H | CH₂Cl | H | CH₃ | H | |
| H | CH₂Cl | H | OCH₃ | H | |
| H | CH₂Cl | H | OCH₃ | CH₂OC₂H₅ | |
| H | CH₂Cl | H | OCF₂H | OCH₃ | |
| H | CH₂Cl | H | OCH₃ | CH(OCH₃)₂ | |
| H | CH₂Cl | H | CH₃ | OC₂H₅ | |
| H | CH₂Cl | H | CH₃ | CH₂OCH₃ | |
| H | CH₂Cl | H | OCH₃ | CH₂OCH₃ | |
| H | CH₂Cl | H | OCH₃ | C₂H₅ | |
| H | CH₂Cl | H | OC₂CF₅ | OCH₃ | |
| H | CH₂Cl | H | OCH₂CF₃ | OCH₃ | |
| H | CH₂Cl | H | CF₃ | OCH₃ | |
| H | CH₂Cl | H | CH₂F | OCH₃ | |
| H | CH₂Cl | H | CH₂Cl | OCH₃ | |
| H | CH₂Cl | H | CH₂Br | OCH₃ | |
| H | CH₂Cl | H | F | OCH₃ | |
| H | CH₂Cl | H | I | OCH₃ | |
| H | CH₂Cl | H | OCH₂CH₂F | OCH₃ | |
| H | CH₂Cl | H | OCH₂CH₂CF₃ | OCH₃ | |
| H | CH₂Cl | H | OCH₂CHF₂ | CH₃ | |
| H | CH₂Cl | H | OCH₂CF₃ | CH₃ | |
| H | CH₂Cl | H | Cl | OC₂H₅ | 117–120 |
| H | CH₂Cl | H | OC₂H₅ | NHCH₃ | |
| H | CH₂Cl | H | OCH₃ | CH₂SCH₃ | |
| H | CH₂Cl | H | OCF₂H | CH₃ | |
| H | CH₂Cl | H | Cl | OCF₂H | |
| H | CHClCH₃ | H | OCH₃ | OCH₃ | 139–142 |
| H | CHClCH₃ | H | CH₃ | OCH₃ | 131–133 |
| H | CHClCH₃ | H | CH₃ | CH₃ | |
| H | CHClCH₃ | H | Cl | OCH₃ | 137–138 |
| H | CHClCH₃ | H | Br | OCH₃ | |
| H | CHClCH₃ | H | CH₃ | H | |
| H | CHClCH₃ | H | OCH₃ | H | |
| H | CHClCH₃ | H | OCH₃ | CH₂OC₂H₅ | |
| H | CHClCH₃ | H | OCF₂H | OCH₃ | |
| H | CHClCH₃ | H | OCH₃ | CH(OCH₃)₃ | |
| H | CHClCH₃ | H | CH₃ | CH₂OCH₃ | |
| H | CHClCH₃ | H | CH₃ | CH₂OCH₃ | |
| H | CHClCH₃ | H | OCH₃ | C₂H₅ | |
| H | CHClCH₃ | H | OCH₃ | C₂H₅ | |
| H | CHClCH₃ | H | OC₂H₅ | OCH₃ | |
| H | CHClCH₃ | H | OCH₂CF₃ | OCH₃ | |
| H | CHClCH₃ | H | CF₃ | OCH₃ | |
| H | CHClCH₃ | H | CH₂F | OCH₃ | |
| H | CHClCH₃ | H | CH₂Cl | OCH₃ | |
| H | CHClCH₃ | H | CH₂Br | OCH₃ | |
| H | CHClCH₃ | H | F | OCH₃ | |
| H | CHClCH₃ | H | I | OCH₃ | |
| H | CHClCH₃ | H | OCH₂CH₂F | OCH₃ | |
| H | CHClCH₃ | H | OCH₂CH₂CF₃ | OCH₃ | |
| H | CHClCH₃ | H | OCH₂CHF₂ | CH₃ | |
| H | CHClCH₃ | H | OCH₂CF₃ | CH₃ | |
| H | CHClCH₃ | H | Cl | OC₂H₅ | |
| H | CHClCH₃ | H | OC₂H₅ | NHCH₃ | |
| H | CHClCH₃ | H | OCH₃ | CH₂SCH₃ | |
| H | CHClCH₃ | H | OCF₂H | CH₃ | |
| H | CHClCH₃ | H | Cl | OCF₂H | |
| H | CH₂BR | H | OCH₃ | OCH₃ | |

TABLE 1-continued

[Structure: pyridine with OH-CHR² substituent, SO₂NH-C(=O)-N(R³)-pyrimidine with X and Y substituents; R¹ on pyridine]

| R¹ | R² | R³ | X | Y | mp (°C.) |
|---|---|---|---|---|---|
| H | CH₂BR | H | CH₃ | OCH₃ | |
| H | CH₂BR | H | CH₃ | CH₃ | |
| H | CH₂BR | H | Cl | OCH₃ | |
| H | CH₂BR | H | Br | OCH₃ | |
| H | CH₂BR | H | CH₃ | H | |
| H | CH₂BR | H | OCH₃ | H | |
| H | CH₂BR | H | OCH₃ | CH₂OC₂H₅ | |
| H | CH₂BR | H | OCF₂H | OCH₃ | |
| H | CH₂BR | H | OCH₃ | CH(OCH₃)₂ | |
| H | CH₂BR | H | CH₃ | OC₂H₅ | |
| H | CH₂BR | H | CH₃ | CH₂OCH₃ | |
| H | CH₂BR | H | OCH₃ | CH₂OCH₃ | |
| H | CH₂BR | H | OCH₃ | C₂H₅ | |
| H | CH₂BR | H | OCH₂CF₃ | OCH₃ | |
| H | CH₂BR | H | OC₂H₅ | OCH₃ | |
| H | CH₂BR | H | CF₃ | OCH₃ | |
| H | CH₂BR | H | CH₂F | OCH₃ | |
| H | CH₂BR | H | CH₂Cl | OCH₃ | |
| H | CH₂BR | H | CH₂Br | OCH₃ | |
| H | CH₂BR | H | F | OCH₃ | |
| H | CH₂BR | H | I | OCH₃ | |
| H | CH₂BR | H | OCH₂CH₂F | OCH₃ | |
| H | CH₂BR | H | OCH₂CH₂CF₃ | OCH₃ | |
| H | CH₂BR | H | OCH₂CHF₂ | CH₃ | |
| H | CH₂BR | H | OCH₂CF₃ | CH₃ | |
| H | CH₂BR | H | Cl | OC₂H₅ | |
| H | CH₂BR | H | OC₂H₅ | NHCH₃ | |
| H | CH₂BR | H | OCH₃ | CH₂SCH₃ | |
| H | CH₂BR | H | OCF₂H | CH₃ | |
| H | CH₂BR | H | Cl | OCF₂H | |
| H | CHF₂ | H | OCH₃ | OCH₃ | |
| H | CHF₂ | H | CH₃ | OCH₃ | |
| H | CHF₂ | H | CH₃ | CH₃ | |
| H | CHF₂ | H | Cl | OCH₃ | |
| H | CHF₂ | H | Br | OCH₃ | |
| H | CHF₂ | H | CH₃ | H | |
| H | CHF₂ | H | OCH₃ | H | |
| H | CHF₂ | H | OCH₃ | CH₂OC₂H₅ | |
| H | CHF₂ | H | OCF₂H | OCH₃ | |
| H | CHF₂ | H | OCH₃ | CH(OCH₃)₂ | |
| H | CHF₂ | H | CH₃ | OC₂H₅ | |
| H | CHF₂ | H | CH₃ | CH₂OCH₃ | |
| H | CHF₂ | H | OCH₃ | CH₂OCH₃ | |
| H | CHF₂ | H | OCH₃ | C₂H₅ | |
| H | CHF₂ | H | OC₂H₅ | OCH₃ | |
| H | CHF₂ | H | OCH₂CF₃ | OCH₃ | |
| H | CHF₂ | H | CF₃ | OCH₃ | |
| H | CHF₂ | H | CH₂F | OCH₃ | |
| H | CHF₂ | H | CH₂Cl | OCH₃ | |
| H | CHF₂ | H | CH₂Br | OCH₃ | |
| H | CHF₂ | H | F | OCH₃ | |
| H | CHF₂ | H | I | OCH₃ | |
| H | CHF₂ | H | OCH₂CH₂F | OCH₃ | |
| H | CHF₂ | H | OCH₂CH₂CF₃ | OCH₃ | |
| H | CHF₂ | H | OCH₂CF₃ | CH₃ | |
| H | CHF₂ | H | OCH₂CHF₂ | CH₃ | |
| H | CHF₂ | H | Cl | OC₂H₅ | |
| H | CHF₂ | H | OC₂H₅ | NHCH₃ | |
| H | CHF₂ | H | OCH₃ | CH₂SCH₃ | |
| H | CHF₂ | H | OCF₂H | CH₃ | |
| H | CHF₂ | H | Cl | OCF₂H | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | Br | OCH₃ | |

TABLE 1-continued

| R¹ | R² | R³ | X | Y | mp (°C.) |
|---|---|---|---|---|---|
| H | CHFCl | H | CH₃ | H | |
| H | CHFCl | H | OCH₃ | H | |
| H | CHFCl | H | OCH₃ | CH₂OC₂H₅ | |
| H | CHFCl | H | OCF₂H | OCH₃ | |
| H | CHFCl | H | OCH₃ | CH(OCH₃)₂ | |
| H | CHFCl | H | CH₃ | OC₂H₅ | |
| H | CHFCl | H | CH₃ | CH₂OCH₃ | |
| H | CHFCl | H | OCH₃ | CH₂OCH₃ | |
| H | CHFCl | H | OCH₃ | C₂H₅ | |
| H | CHFCl | H | OC₂H₅ | OCH₃ | |
| H | CHFCl | H | OCH₂CF₃ | OCH₃ | |
| H | CHFCl | H | CF₃ | OCH₃ | |
| H | CHFCl | H | CH₂F | OCH₃ | |
| H | CHFCl | H | CH₂Cl | OCH₃ | |
| H | CHFCl | H | CH₂Br | OCH₃ | |
| H | CHFCl | H | F | OCH₃ | |
| H | CHFCl | H | I | OCH₃ | |
| H | CHFCl | H | OCH₂CH₂F | OCH₃ | |
| H | CHFCl | H | OCH₂CH₂CF₃ | OCH₃ | |
| H | CHFCl | H | OCH₂CHF₂ | CH₃ | |
| H | CHFCl | H | OCH₂CF₃ | CH₃ | |
| H | CHFCl | H | Cl | OC₂H₅ | |
| H | CHFCl | H | OC₂H₅ | NHCH₃ | |
| H | CHFCl | H | OCH₃ | CH₂SCH₃ | |
| H | CHFCl | H | OCF₂H | CH₃ | |
| H | CHFCl | H | Cl | OCF₂H | |
| H | CHFCl | H | n-C₃F₇ | OCH₃ | |
| H | CHFCl | H | OCH₃ | NHCH₃ | |
| H | CHFCl | H | OCH₃ | N(CH₃)₂ | |
| H | CHFCl | H | OCH₃ | cyclopropyl | |
| H | CHFCl | H | OCH₃ | OCH₂CH₂OCH₃ | |
| H | CHFCl | H | OC₂H₅ | CH₂SCH₃ | |
| H | CHFCl | H | OCH₃ | CH(SCH₃)OC₂H₅ | |
| H | CHFCl | H | OCH₃ | CH(SC₂H₅)₂ | |
| H | CHFCl | H | OCH₃ | 1,3-dioxolan-2-yl | |
| H | CHFCl | H | OCH₃ | N(OCH₃)CH₃ | |
| H | CHFCl | H | OCH₃ | C₂H₅ | |
| H | CHFCl | H | OCH₃ | CF₃ | |
| 6-F | CH₂F | H | OCH₃ | OCH₃ | |
| 6-Cl | CH₂F | H | OCH₃ | OCH₃ | |
| 6-Cl | CH₂Cl | H | OCH₃ | OCH₃ | |
| 6-Cl | CH₂F | H | CH₃ | OCH₃ | |
| 6-Cl | CH₂F | H | CH₃ | CH₃ | |
| 6-Cl | CH₂F | H | Cl | OCH₃ | |
| 6-Br | CH₂F | H | OCH₃ | OCH₃ | |
| 6-CH₂CN | CH₂F | H | OCH₃ | OCH₃ | |
| 6-OCH₃ | CH₂F | H | OCH₃ | OCH₃ | |
| 6-SCH₃ | CH₂F | H | OCH₃ | OCH₃ | |
| 6-OCF₂H | CH₂F | H | OCH₃ | OCH₃ | |
| H | CH₂F | CH₃ | OCH₃ | OCH₃ | |
| H | CH₂F | CH₃ | CH₃ | OCH₃ | |
| H | CH₂Cl | CH₃ | OCH₃ | OCH₃ | |
| H | CHF₂ | CH₃ | OCH₃ | OCH₃ | |
| H | CH₂Br | CH₃ | OCH₃ | OCH₃ | |
| 6-Cl | CH₂Cl | CH₃ | OCH₃ | OCH₃ | |

TABLE 2

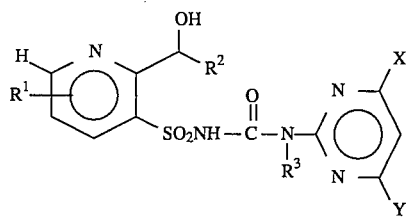

| R¹ | R² | R³ | X | Y | mp (°C.) |
|---|---|---|---|---|---|
| H | CH₂F | H | OCH₃ | OCH₃ | 162–164 |
| H | CH₂F | H | CH₃ | OCH₃ | 147–149 |
| H | CH₂F | H | CH₃ | OCH₃ | 155–151 |
| H | CH₂F | H | Cl | OCH₃ | 125–128 |
| H | CH₂F | H | Br | OCH₃ | |
| H | CH₂F | H | H | CH₃ | |
| H | CH₂F | H | OCH₃ | H | |
| H | CH₂F | H | OCH₃ | CH₂OC₂H₅ | |
| H | CH₂F | H | OCF₂H | OCH₃ | |
| H | CH₂F | H | OCH₃ | CH(OCH₃)₂ | |
| H | CH₂F | H | CH₃ | OC₂H₅ | |
| H | CH₂F | H | CH₃ | CH₂OCH₃ | |
| H | CH₂F | H | OCH₃ | CH₂OCH₃ | |
| H | CH₂F | H | C₂H₅ | OCH₃ | |
| H | CH₂F | H | OC₂H₅ | OCH₃ | |
| H | CH₂F | H | OCH₂CF₃ | OCH₃ | |
| H | CH₂F | H | CF₃ | OCH₃ | |
| H | CH₂F | H | CH₂F | OCH₃ | |
| H | CH₂F | H | CH₂Cl | OCH₃ | |
| H | CH₂F | H | CF₂Br | OCH₃ | |
| H | CH₂F | H | F | OCH₃ | |
| H | CH₂F | H | I | OCH₃ | |
| H | CH₂F | H | OCH₂CH₂F | OCH₃ | |
| H | CH₂F | H | OCH₂CH₂CF₃ | OCH₃ | |
| H | CH₂F | H | OCH₂CHF₂ | CH₃ | |
| H | CH₂F | H | OCH₂CF₃ | CH₃ | |
| H | CH₂F | H | Cl | OC₂H₅ | 115–117 |
| H | CH₂F | H | OC₂H₅ | NHCH₃ | |
| H | CH₂F | H | OC₂H₅ | CH₂SCH₃ | |
| H | CH₂F | H | OCF₂H | CH₃ | |
| H | CH₂F | H | Cl | OCF₂H | |
| H | CH₂F | H | NH₂ | OC₂H₅ | |
| H | CH₂F | H | n-C₃H₇ | OCH₃ | |
| H | CH₂F | H | NHCH₃ | OCH₃ | |
| H | CH₂F | H | OCH₃ | SCH₃ | |
| H | CH₂F | H | OCH₃ | SCF₂H | |
| H | CH₂F | H | OCH₃ | OCH₂CCH | |
| H | CH₂F | H | OCH₃ | OCH₂CH=CH₂ | |
| H | CH₂F | H | OCH₃ | CCH | |
| H | CH₂F | H | OCH₃ | N(CH₃)₂ | |
| H | CH₂F | H | OCH₃ | cyclopropyl | |
| H | CH₂F | H | OCH₃ | NH₂ | |
| H | CH₂F | H | OCH₃ | CF₃ | |
| H | CH₂F | H | OCH₃ | OCH₂CH₂OCH₃ | |
| H | CH₂F | H | OCH₃ | CH₂SCH₃ | |
| H | CH₂F | H | OCH₃ | CHO | |
| H | CH₂F | H | OCH₃ | COCH₃ | |
| H | CH₂F | H | OCH₃ | CH(SCH₃)OC₂H₅ | |
| H | CH₂F | H | OCH₃ | C(CH₃)(SCH₃)₂ | |
| H | CH₂F | H | OCH₃ | C(SC₂H₅)₂ | |
| H | CH₂F | H | OCH₃ | 1,3-dioxolan-2-yl | |
| H | CH₂F | H | OCH₃ | 2-methyl-1,3-oxathiolan-2yl | |
| H | CH₂F | H | OCH₃ | 1,3-oxathian-2-yl | |
| H | CH₂F | H | OCH₃ | 2-methyl-1,3-dithian-2-yl | |
| H | CH₂F | H | OCH₃ | 4-methyl-1,3-dioxolan-2-yl | |
| H | CH₂F | H | OCH₃ | 2-4-dimethyl-1,3-dithiolan-2-yl | |
| H | CH₂F | H | OCH₃ | N(OCH₃)(CH₃) | |
| H | CH₂F | H | OCH₃ | CCCH₃ | |
| H | CH₂F | H | OCH₃ | C₂H₅ | |
| H | CH₂F | H | OCH₃ | OCF₂Br | |
| H | CHFCH₃ | H | OCH₃ | OCH₃ | 137–139 |
| H | CHFCH₃ | H | CH₃ | OCH₃ | |
| H | CHFCH₃ | H | CH₃ | CH₃ | |
| H | CHFCH₃ | H | Cl | OCH₃ | |
| H | CHFCH₃ | H | Br | OCH₃ | |

| | | | | |
|---|---|---|---|---|
| H | CHFCH₃ | H | CH₃ | H |
| H | CHFCH₃ | H | OCH₃ | H |
| H | CHFCH₃ | H | OCH₃ | CH₂OC₂H₅ |
| H | CHFCH₃ | H | OCF₂H | OCH₃ |
| H | CHFCH₃ | H | OCH₃ | CH(OCH₃)₂ |
| H | CHFCH₃ | H | CH₃ | OC₂H₅ |
| H | CHFCH₃ | H | CH₃ | CH₂OCH₃ |
| H | CHFCH₃ | H | OCH₃ | CH₂OCH₃ |
| H | CHFCH₃ | H | OCH₃ | C₂H₅ |
| H | CHFCH₃ | H | OC₂H₅ | OCH₃ |
| H | CHFCH₃ | H | OCH₂CF₃ | OCH₃ |
| H | CHFCH₃ | H | CF₃ | OCH₃ |
| H | CHFCH₃ | H | CH₂F | OCH₃ |
| H | CHFCH₃ | H | CH₂Cl | OCH₃ |
| H | CHFCH₃ | H | CH₂Br | OCH₃ |
| H | CHFCH₃ | H | F | OCH₃ |
| H | CHFCH₃ | H | I | OCH₃ |
| H | CHFCH₃ | H | OCH₂CH₂F | OCH₃ |
| H | CHFCH₃ | H | OCH₂CH₂CF₃ | OCH₃ |
| H | CHFCH₃ | H | OCH₂CHF₂ | CH₃ |
| H | CHFCH₃ | H | OCH₂CF₃ | CH₃ |
| H | CHFCH₃ | H | Cl | OC₂H₅ |
| H | CHFCH₃ | H | OC₂H₅ | NHCH₃ |
| H | CHFCH₃ | H | OCH₃ | CH₂SCH₃ |
| H | CHFCH₃ | H | OCF₂H | CH₃ |
| H | CHFCH₃ | H | Cl | OCF₂H |
| H | CH₂CH₂F | H | OCH₃ | OCH₃ |
| H | CH₂CH₂F | H | CH₃ | OCH₃ |
| H | CH₂CH₂F | H | CH₃ | CH₃ |
| H | CH₂CH₂F | H | Cl | OCH₃ |
| H | CH₂CH₂F | H | Br | OCH₃ |
| H | CH₂CH₂F | H | CH₃ | H |
| H | CH₂CH₂F | H | OCH₃ | H |
| H | CH₂CH₂F | H | OCH₃ | CH₂OC₂H₅ |
| H | CH₂CH₂F | H | OCF₂H | OCH₃ |
| H | CH₂CH₂F | H | OCH₃ | CH(OCH₃)₂ |
| H | CH₂CH₂F | H | CH₃ | OC₂H₅ |
| H | CH₂CH₂F | H | CH₃ | CH₂OCH₃ |
| H | CH₂CH₂F | H | OCH₃ | CH₂OCH₃ |
| H | CH₂CH₂F | H | OCH₃ | C₂H₅ |
| H | CH₂CH₂F | H | OC₂H₅ | OCH₃ |
| H | CH₂CH₂F | H | OCH₂CF₃ | OCH₃ |
| H | CH₂CH₂F | H | CF₃ | OCH₃ |
| H | CH₂CH₂F | H | CH₂F | OCH₃ |
| H | CH₂CH₂F | H | CH₂Cl | OCH₃ |
| H | CH₂CH₂F | H | CH₂Br | OCH₃ |
| H | CH₂CH₂F | H | F | OCH₃ |
| H | CH₂CH₂F | H | I | OCH₃ |
| H | CH₂CH₂F | H | OCH₂CH₂F | OCH₃ |
| H | CH₂CH₂F | H | OCH₂CH₂CF₃ | OCH₃ |
| H | CH₂CH₂F | H | OCH₂CHF₂ | CH₃ |
| H | CH₂CH₂F | H | OCH₂CF₃ | CH₃ |
| H | CH₂CH₂F | H | Cl | OC₂H₅ |
| H | CH₂CH₂F | H | OCH₂H₅ | NHCH₃ |
| H | CH₂CH₂F | H | OCH₃ | CH₂SCH₃ |
| H | CH₂CH₂F | H | OCF₂H | CH₃ |
| H | CH₂CH₂F | H | Cl | OCF₂H |
| H | CH₂Cl | H | OCH₃ | OCH₃ |
| H | CH₂Cl | H | CH₃ | OCH₃ |
| H | CH₂Cl | H | CH₃ | CH₃ |
| H | CH₂Cl | H | Cl | OCH₃ |
| H | CH₂Cl | H | Br | OCH₃ |
| H | CH₂Cl | H | CH₃ | H |
| H | CH₂Cl | H | OCH₃ | H |
| H | CH₂Cl | H | OCH₃ | CH₂OC₂H₅ |
| H | CH₂Cl | H | OCF₂H | OCH₃ |
| H | CH₂Cl | H | OCH₃ | CH(OCH₃)₂ |
| H | CH₂Cl | H | CH₃ | OC₂H₅ |
| H | CH₂Cl | H | CH₃ | CH₂OCH₃ |
| H | CH₂Cl | H | OCH₃ | CH₂OCH₃ |
| H | CH₂Cl | H | OCH₃ | C₂H₅ |
| H | CH₂Cl | H | OC₂H₅ | OCH₃ |
| H | CH₂Cl | H | OCH₂CF₃ | OCH₃ |
| H | CH₂Cl | H | CF₃ | OCH₃ |
| H | CH₂Cl | H | CH₂F | OCH₃ |
| H | CH₂Cl | H | CH₂Cl | OCH₃ |
| H | CH₂Cl | H | CH₂Br | OCH₃ |
| H | CH₂Cl | H | F | OCH₃ |
| H | CH₂Cl | H | I | OCH₃ |
| H | CH₂Cl | H | OCH₂CH₂F | OCH₃ |
| H | CH₂Cl | H | OCH₂CH₂CF₃ | OCH₃ |
| H | CH₂Cl | H | OCH₂CHF₂ | CH₃ |

| | | | | |
|---|---|---|---|---|
| H | CH₂Cl | H | OCH₂CF₃ | CH₃ |
| H | CH₂Cl | H | Cl | OC₂H₅ |
| H | CH₂Cl | H | OC₂H₅ | NHCH₃ |
| H | CH₂Cl | H | OCH₃ | CH₂SCH₃ |
| H | CH₂Cl | H | OCF₂H | CH₃ |
| H | CH₂Cl | H | Cl | OCF₂H |
| H | CHClCH₃ | H | OCH₃ | OCH₃ |
| H | CHClCH₃ | H | CH₃ | OCH₃ |
| H | CHClCH₃ | H | CH₃ | CH₃ |
| H | CHClCH₃ | H | Cl | OCH₃ |
| H | CHClCH₃ | H | Br | OCH₃ |
| H | CHClCH₃ | H | CH₃ | H |
| H | CHClCH₃ | H | OCH₃ | H |
| H | CHClCH₃ | H | OCH₃ | CH₂OC₂H₅ |
| H | CHClCH₃ | H | OCF₂H | OCH₃ |
| H | CHClCH₃ | H | OCH₃ | CH(OCH₃)₂ |
| H | CHClCH₃ | H | CH₃ | OC₂H₅ |
| H | CHClCH₃ | H | CH₃ | CH₂OCH₃ |
| H | CHClCH₃ | H | OCH₃ | CH₂OCH₃ |
| H | CHClCH₃ | H | OCH₃ | C₂H₅ |
| H | CHClCH₃ | H | OC₂H₅ | OCH₃ |
| H | CHClCH₃ | H | OCH₂CF₃ | OCH₃ |
| H | CHClCH₃ | H | CF₃ | OCH₃ |
| H | CHClCH₃ | H | CH₂F | OCH₃ |
| H | CHClCH₃ | H | CH₂Cl | OCH₃ |
| H | CHClCH₃ | H | CH₂Br | OCH₃ |
| H | CHClCH₃ | H | F | OCH₃ |
| H | CHClCH₃ | H | I | OCH₃ |
| H | CHClCH₃ | H | OCH₂CH₂F | OCH₃ |
| H | CHClCH₃ | H | OCH₂CH₂CF₃ | OCH₃ |
| H | CHClCH₃ | H | OCH₂CHF₂ | CH₃ |
| H | CHClCH₃ | H | OCH₂CF₃ | CH₃ |
| H | CHClCH₃ | H | Cl | OC₂H₅ |
| H | CHClCH₃ | H | OC₂H₅ | NHCH₃ |
| H | CHClCH₃ | H | OCH₃ | CH₂SCH₃ |
| H | CHClCH₃ | H | OCF₂H | CH₃ |
| H | CHClCH₃ | H | Cl | OCF₂H |
| H | CH₂Br | H | OCH₃ | OCH₃ |
| H | CH₂Br | H | CH₃ | OCH₃ |
| H | CH₂Br | H | CH₃ | CH₃ |
| H | CH₂Br | H | Cl | OCH₃ |
| H | CH₂Br | H | Br | OCH₃ |
| H | CH₂Br | H | CH₃ | H |
| H | CH₂Br | H | OCH₃ | H |
| H | CH₂Br | H | OCH₃ | CH₂OC₂H₅ |
| H | CH₂Br | H | OCF₂H | OCH₃ |
| H | CH₂Br | H | OCH₃ | CH(OCH₃)₂ |
| H | CH₂Br | H | CH₃ | OC₂H₅ |
| H | CH₂Br | H | CH₃ | CH₂OCH₃ |
| H | CH₂Br | H | OCH₃ | CH₂OCH₃ |
| H | CH₂Br | H | OCH₃ | C₂H₅ |
| H | CH₂Br | H | OC₂H₅ | OCH₃ |
| H | CH₂Br | H | OCH₂CF₃ | OCH₃ |
| H | CH₂Br | H | CF₃ | OCH₃ |
| H | CH₂Br | H | CH₂F | OCH₃ |
| H | CH₂Br | H | CH₂Cl | OCH₃ |
| H | CH₂Br | H | CH₂Br | OCH₃ |
| H | CH₂Br | H | F | OCH₃ |
| H | CH₂Br | H | I | OCH₃ |
| H | CH₂Br | H | OCH₂CH₂F | OCH₃ |
| H | CH₂Br | H | OCH₂CH₂CF₃ | OCH₃ |
| H | CH₂Br | H | OCH₂CHF₂ | CH₃ |
| H | CH₂Br | H | OCH₂CF₃ | CH₃ |
| H | CH₂Br | H | Cl | OC₂H₅ |
| H | CH₂Br | H | OC₂H₅ | NHCH₃ |
| H | CH₂Br | H | OCH₃ | CH₂SCH₃ |
| H | CH₂Br | H | OCF₂H | CH₃ |
| H | CH₂Br | H | Cl | OCF₂H |
| H | CHF₂ | H | OCH₃ | OCH₃ |
| H | CHF₂ | H | CH₃ | OCH₃ |
| H | CHF₂ | H | CH₃ | CH₃ |
| H | CHF₂ | H | Cl | OCH₃ |
| H | CHF₂ | H | Br | OCH₃ |
| H | CHF₂ | H | CH₃ | H |
| H | CHF₂ | H | OCH₃ | H |
| H | CHF₂ | H | OCH₃ | CH₂OC₂H₅ |
| H | CHF₂ | H | OCF₂H | OCH₃ |
| H | CHF₂ | H | OCH₃ | CH(OCH₃)₂ |
| H | CHF₂ | H | CH₃ | OC₂H₅ |
| H | CHF₂ | H | CH₃ | CH₂OCH₃ |
| H | CHF₂ | H | OCH₃ | CH₂OCH₃ |
| H | CHF₂ | H | OCH₃ | C₂H₅ |

| | | | | |
|---|---|---|---|---|
| H | CHF$_2$ | H | OC$_2$H$_5$ | OCH$_3$ |
| H | CHF$_2$ | H | OCH$_2$CF$_3$ | OCH$_3$ |
| H | CHF$_2$ | H | CF$_3$ | OCH$_3$ |
| H | CHF$_2$ | H | CH$_2$F | OCH$_3$ |
| H | CHF$_2$ | H | CH$_2$Cl | OCH$_3$ |
| H | CHF$_2$ | H | CH$_2$Br | OCH$_3$ |
| H | CHF$_2$ | H | F | OCH$_3$ |
| H | CHF$_2$ | H | I | OCH$_3$ |
| H | CHF$_2$ | H | OCH$_2$CH$_2$F | OCH$_3$ |
| H | CHF$_2$ | H | OCH$_2$CH$_2$CF$_3$ | OCH$_3$ |
| H | CHF$_2$ | H | OCH$_2$CF$_3$ | CH$_3$ |
| H | CHF$_2$ | H | OCH$_2$CHF$_2$ | CH$_3$ |
| H | CHF$_2$ | H | Cl | OC$_2$H$_5$ |
| H | CHF$_2$ | H | OC$_2$H$_5$ | NHCH$_3$ |
| H | CHF$_2$ | H | OCH$_3$ | CH$_2$SCH$_3$ |
| H | CHF$_2$ | H | OCF$_2$H | CH$_3$ |
| H | CHF$_2$ | H | Cl | OCF$_2$H |
| H | CHFCl | H | OCH$_3$ | OCH$_3$ |
| H | CHFCl | H | CH$_3$ | OCH$_3$ |
| H | CHFCl | H | CH$_3$ | CH$_3$ |
| H | CHFCl | H | Cl | OCH$_3$ |
| H | CHFCl | H | Br | OCH$_3$ |
| H | CHFCl | H | CH$_3$ | H |
| H | CHFCl | H | OCH$_3$ | H |
| H | CHFCl | H | OCH$_3$ | CH$_2$OC$_2$H$_5$ |
| H | CHFCl | H | OCF$_2$H | OCH$_3$ |
| H | CHFCl | H | OCH$_3$ | CH(OCH$_3$)$_2$ |
| H | CHFCl | H | CH$_3$ | OC$_2$H$_5$ |
| H | CHFCl | H | CH$_3$ | CH$_2$OCH$_3$ |
| H | CHFCl | H | OCH$_3$ | CH$_2$OCH$_3$ |
| H | CHFCl | H | OCH$_3$ | C$_2$H$_5$ |
| H | CHFCl | H | OC$_2$H$_5$ | OCH$_3$ |
| H | CHFCl | H | OCH$_2$CF$_3$ | OCH$_3$ |
| H | CHFCl | H | CF$_3$ | OCH$_3$ |
| H | CHFCl | H | CH$_2$F | OCH$_3$ |
| H | CHFCl | H | CH$_2$Cl | OCH$_3$ |
| H | CHFCl | H | CH$_2$Br | OCH$_3$ |
| H | CHFCl | H | F | OCH$_3$ |
| H | CHFCl | H | I | OCH$_3$ |
| H | CHFCl | H | OCH$_2$CH$_2$F | OCH$_3$ |
| H | CHFCl | H | OCH$_2$CH$_2$CF$_3$ | OCH$_3$ |
| H | CHFCl | H | OCH$_2$CHF$_2$ | CH$_3$ |
| H | CHFCl | H | OCH$_2$CF$_3$ | CH$_3$ |
| H | CHFCl | H | Cl | OC$_2$H$_5$ |
| H | CHFCl | H | OC$_2$H$_5$ | NHCH$_3$ |
| H | CHFCl | H | OCH$_3$ | CH$_2$SCH$_3$ |
| H | CHFCl | H | OCF$_2$H | CH$_3$ |
| H | CHFCl | H | Cl | OCF$_2$H |
| H | CHFCl | H | n-C$_3$H$_7$ | OCH$_3$ |
| H | CHFCl | H | OCH$_3$ | NHCH$_3$ |
| H | CHFCl | H | OCH$_3$ | N(CH$_3$)$_2$ |
| H | CHFCl | H | OCH$_3$ | cyclopropyl |
| H | CHFCl | H | OCH$_3$ | OCH$_2$CH$_2$OCH$_3$ |
| H | CHFCl | H | OC$_2$H$_5$ | CH$_2$SCH$_3$ |
| H | CHFCl | H | OCH$_3$ | CH(SCH$_3$)OC$_2$H$_5$ |
| H | CHFCl | H | OCH$_3$ | CH(SC$_2$H$_5$)$_2$ |
| H | CHFCl | H | OCH$_3$ | 1,3-dioxolan-2-yl |
| H | CHFCl | H | OCH$_3$ | N(OCH$_3$)CH$_3$ |
| H | CHFCl | H | OCH$_3$ | C$_2$H$_5$ |
| H | CHFCl | H | OCH$_3$ | CF$_3$ |
| 5-F | CH$_2$F | H | OCH$_3$ | OCH$_3$ |
| 5-Cl | CH$_2$F | H | OCH$_3$ | OCH$_3$ |
| 5-Cl | CH$_2$F | H | OCH$_3$ | OCH$_3$ |
| 5-Cl | CH$_2$F | H | CH$_3$ | OCH$_3$ |
| 5-Cl | CH$_2$F | H | CH$_3$ | CH$_3$ |
| 5-Cl | CH$_2$F | H | Cl | OCH$_3$ |
| 5-Br | CH$_2$F | H | OCH$_3$ | OCH$_3$ |
| 5-CH$_2$CN | CH$_2$F | H | OCH$_3$ | OCH$_3$ |
| 5-OCH$_3$ | CH$_2$F | H | OCH$_3$ | OCH$_3$ |
| 5-SCH$_3$ | CH$_2$F | H | OCH$_3$ | OCH$_3$ |
| 5-OCF$_2$H | CH$_2$F | H | OCH$_3$ | OCH$_3$ |
| H | CH$_2$F | CH$_3$ | OCH$_3$ | OCH$_3$ |
| H | CH$_2$F | CH$_3$ | OCH$_3$ | OCH$_3$ |
| H | CH$_2$Cl | CH$_3$ | OCH$_3$ | OCH$_3$ |
| H | CHF$_2$ | CH$_3$ | OCH$_3$ | OCH$_3$ |
| H | CH$_2$Br | CH$_3$ | OCH$_3$ | OCH$_3$ |
| 4-Cl | CH$_2$Cl | CH$_3$ | OCH$_3$ | OCH$_3$ |

TABLE 3

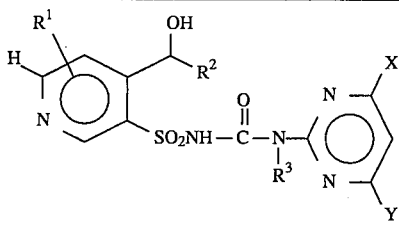

| R¹ | R² | R³ | X | Y | mp (°C.) |
|---|---|---|---|---|---|
| H | CH₂F | H | OCH₃ | OCH₃ | |
| H | CH₂F | H | CH₃ | OCH₃ | |
| H | CH₂F | H | CH₃ | CH₃ | |
| H | CH₂F | H | Cl | OCH₃ | |
| H | CH₂F | H | Br | OCH₃ | |
| H | CH₂F | H | H | CH₃ | |
| H | CH₂F | H | OCH₃ | H | |
| H | CH₂F | H | OCH₃ | CH₂OC₂H₅ | |
| H | CH₂F | H | OCF₂H | OCH₃ | |
| H | CH₂F | H | OCH₃ | CH(OCH₃)₂ | |
| H | CH₂F | H | CH₃ | OC₂H₅ | |
| H | CH₂F | H | CH₃ | CH₂OCH₃ | |
| H | CH₂F | H | OCH₃ | CH₂OCH₃ | |
| H | CH₂F | H | C₂H₅ | OCH₃ | |
| H | CH₂F | H | OC₂H₅ | OCH₃ | |
| H | CH₂F | H | OCH₂CF₃ | OCH₃ | |
| H | CH₂F | H | CF₃ | OCH₃ | |
| H | CH₂F | H | CH₂F | OCH₃ | |
| H | CH₂F | H | CH₂Cl | OCH₃ | |
| H | CH₂F | H | CH₂Br | OCH₃ | |
| H | CH₂F | H | F | OCH₃ | |
| H | CH₂F | H | I | OCH₃ | |
| H | CH₂F | H | OCH₂CH₂F | OCH₃ | |
| H | CH₂F | H | OCH₂CH₂CF₃ | OCH₃ | |
| H | CH₂F | H | OCH₂CHF₂ | CH₃ | |
| H | CH₂F | H | OCH₂CF₃ | CH₃ | |
| H | CH₂F | H | Cl | OC₂H₅ | |
| H | CH₂F | H | OC₂H₅ | NHCH₃ | |
| H | CH₂F | H | OC₂H₅ | CH₂SCH₃ | |
| H | CH₂F | H | OCF₂H | CH₃ | |
| H | CH₂F | H | Cl | OCF₂H | |
| H | CH₂F | H | NH₂ | OC₂H₅ | |
| H | CH₂F | H | n-C₃H₇ | OCH₃ | |
| H | CH₂F | H | NHCH₃ | OCH₃ | |
| H | CH₂F | H | OCH₃ | SCH₃ | |
| H | CH₂F | H | OCH₃ | SCF₂H | |
| H | CH₂F | H | OCH₃ | OCH₂CCH | |
| H | CH₂F | H | OCH₃ | OCH₂CH=CH₂ | |
| H | CH₂F | H | OCH₃ | CCH | |
| H | CH₂F | H | OCH₃ | N(CH₃)₂ | |
| H | CH₂F | H | OCH₃ | cyclopropyl | |
| H | CH₂F | H | OCH₃ | NH₂ | |
| H | CH₂F | H | OCH₃ | CF₃ | |
| H | CH₂F | H | OCH₃ | OCH₂CH₂OCH₃ | |
| H | CH₂F | H | OCH₃ | CH₂SCH₃ | |
| H | CH₂F | H | OCH₃ | CHO | |
| H | CH₂F | H | OCH₃ | COCH₃ | |
| H | CH₂F | H | OCH₃ | CH(SCH₃)OC₂H₅ | |
| H | CH₂F | H | OCH₃ | C(CH₃)(SCH₃)₂ | |
| H | CH₂F | H | OCH₃ | C(SC₂H₅)₂ | |
| H | CH₂F | H | OCH₃ | 1,3-dioxolan-2-yl | |
| H | CH₂F | H | OCH₃ | 2-methyl-1,3-oxathiolan-2yl | |
| H | CH₂F | H | OCH₃ | 1,3-oxathian-2-yl | |
| H | CH₂F | H | OCH₃ | 2-methyl-1,3-dithian-2-yl | |
| H | CH₂F | H | OCH₃ | 4-methyl-1,3-dioxolan-2-yl | |
| H | CH₂F | H | OCH₃ | 2-4-dimethyl-1,3-dithiolan-2-yl | |
| H | CH₂F | H | OCH₃ | N(OCH₃)(CH₃) | |
| H | CH₂F | H | OCH₃ | CCCH₃ | |
| H | CH₂F | H | OCH₃ | C₂H₅ | |
| H | CH₂F | H | OCH₃ | OCF₂Br | |
| H | CHFCH₃ | H | OCH₃ | OC₂H₅ | |

TABLE 3-continued

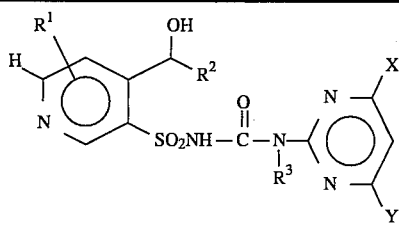

| R¹ | R² | R³ | X | Y | mp (°C.) |
|---|---|---|---|---|---|
| H | CHFCH₃ | H | CH₃ | OCH₃ | |
| H | CHFCH₃ | H | CH₃ | CH₃ | |
| H | CHFCH₃ | H | Cl | OCH₃ | |
| H | CHFCH₃ | H | Br | OCH₃ | |
| H | CHFCH₃ | H | CH₃ | H | |
| H | CHFCH₃ | H | OCH₃ | H | |
| H | CHFCH₃ | H | OCH₃ | CH₂OC₂H₅ | |
| H | CHFCH₃ | H | OCF₂H | OCH₃ | |
| H | CHFCH₃ | H | OCH₃ | CH(OCH₃)₂ | |
| H | CHFCH₃ | H | CH₃ | OC₂H₅ | |
| H | CHFCH₃ | H | CH₃ | CH₂OCH₃ | |
| H | CHFCH₃ | H | OCH₃ | CH₂OCH₃ | |
| H | CHFCH₃ | H | OCH₃ | C₂H₅ | |
| H | CHFCH₃ | H | OC₂H₅ | OCH₃ | |
| H | CHFCH₃ | H | OCH₂CF₃ | OCH₃ | |
| H | CHFCH₃ | H | CF₃ | OCH₃ | |
| H | CHFCH₃ | H | CH₂F | OCH₃ | |
| H | CHFCH₃ | H | CH₂Cl | OCH₃ | |
| H | CHFCH₃ | H | CH₂Br | OCH₃ | |
| H | CHFCH₃ | H | F | OCH₃ | |
| H | CHFCH₃ | H | I | OCH₃ | |
| H | CHFCH₃ | H | OCH₂CH₂F | OCH₃ | |
| H | CHFCH₃ | H | OCH₂CH₂CF₃ | OCH₃ | |
| H | CHFCH₃ | H | OCH₂CHF₂ | CH₃ | |
| H | CHFCH₃ | H | OCH₂CF₃ | CH₃ | |
| H | CHFCH₃ | H | Cl | OC₂H₅ | |
| H | CHFCH₃ | H | OC₂H₅ | NHCH₃ | |
| H | CHFCH₃ | H | OCH₃ | CH₂SCH₃ | |
| H | CHFCH₃ | H | OCF₂H | CH₃ | |
| H | CHFCH₃ | H | Cl | OCF₂H | |
| H | CH₂CH₂F | H | OCH₃ | OCH₃ | |
| H | CH₂CH₂F | H | CH₃ | OCH₃ | |
| H | CH₂CH₂F | H | CH₃ | CH₃ | |
| H | CH₂CH₂F | H | Cl | OCH₃ | |
| H | CH₂CH₂F | H | Br | OCH₃ | |
| H | CH₂CH₂F | H | CH₃ | H | |
| H | CH₂CH₂F | H | OCH₃ | H | |
| H | CH₂CH₂F | H | OCH₃ | CH₂OC₂H₅ | |
| H | CH₂CH₂F | H | OCF₂H | OCH₃ | |
| H | CH₂CH₂F | H | OCH₃ | CH(OCH₃)₂ | |
| H | CH₂CH₂F | H | CH₃ | OC₂H₅ | |
| H | CH₂CH₂F | H | CH₃ | CH₂OCH₃ | |
| H | CH₂CH₂F | H | OCH₃ | CH₂OCH₃ | |
| H | CH₂CH₂F | H | OCH₃ | C₂H₅ | |
| H | CH₂CH₂F | H | OCH₂CF₃ | OCH₃ | |
| H | CH₂CH₂F | H | CF₃ | OCH₃ | |
| H | CH₂CH₂F | H | CH₂F | OCH₃ | |
| H | CH₂CH₂F | H | CH₂Cl | OCH₃ | |
| H | CH₂CH₂F | H | CH₂Br | OCH₃ | |
| H | CH₂CH₂F | H | F | OCH₃ | |
| H | CH₂CH₂F | H | I | OCH₃ | |
| H | CH₂CH₂F | H | OCH₂CH₂F | OCH₃ | |
| H | CH₂CH₂F | H | OCH₂CH₂CF₃ | OCH₃ | |
| H | CH₂CH₂F | H | OCH₂CHF₂ | CH₃ | |
| H | CH₂CH₂F | H | OCH₂CF₃ | CH₃ | |
| H | CH₂CH₂F | H | Cl | OC₂H₅ | |
| H | CH₂CH₂F | H | OC₂H₅ | NHCH₃ | |
| H | CH₂CH₂F | H | OCH₃ | CH₂SCH₃ | |
| H | CH₂CH₂F | H | OCF₂H | CH₃ | |
| H | CH₂CH₂F | H | Cl | OCF₂H | |
| H | CHFCH₃ | H | OC₂H₅ | OC₂H₅ | |
| H | CHFCH₃ | H | CH₃ | OCH₃ | |
| H | CHFCH₃ | H | CH₃ | CH₃ | |
| H | CHFCH₃ | H | Cl | OCH₃ | |

TABLE 3-continued

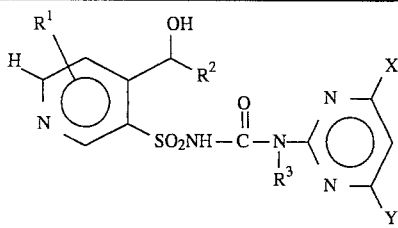

| R¹ | R² | R³ | X | Y | mp (°C.) |
|---|---|---|---|---|---|
| H | CHFCH₃ | H | Br | OCH₃ | |
| H | CHFCH₃ | H | CH₃ | H | |
| H | CHFCH₃ | H | OCH₃ | H | |
| H | CHFCH₃ | H | OCH₃ | CH₂OC₂H₅ | |
| H | CHFCH₃ | H | OCF₂H | OCH₃ | |
| H | CHFCH₃ | H | OCH₃ | CH(OCH₃)₂ | |
| H | CHFCH₃ | H | CH₃ | OC₂H₅ | |
| H | CHFCH₃ | H | CH₃ | CH₂OCH₃ | |
| H | CHFCH₃ | H | OCH₃ | CH₂OCH₃ | |
| H | CHFCH₃ | H | OCH₃ | C₂H₅ | |
| H | CHFCH₃ | H | OC₂H₅ | OCH₃ | |
| H | CHFCH₃ | H | OCH₂CF₃ | OCH₃ | |
| H | CHFCH₃ | H | CF₃ | OCH₃ | |
| H | CHFCH₃ | H | CH₂F | OCH₃ | |
| H | CHFCH₃ | H | CH₂Cl | OCH₃ | |
| H | CHFCH₃ | H | CH₂Br | OCH₃ | |
| H | CHFCH₃ | H | F | OCH₃ | |
| H | CHFCH₃ | H | I | OCH₃ | |
| H | CHFCH₃ | H | OCH₂CH₂F | OCH₃ | |
| H | CHFCH₃ | H | OCH₂CH₂CF₃ | OCH₃ | |
| H | CHFCH₃ | H | OCH₂CHF₂ | CH₃ | |
| H | CHFCH₃ | H | OCH₂CF₃ | CH₃ | |
| H | CHFCH₃ | H | Cl | OC₂H₅ | |
| H | CHFCH₃ | H | OC₂H₅ | NHCH₃ | |
| H | CHFCH₃ | H | OCH₃ | CH₂SCH₃ | |
| H | CHFCH₃ | H | OCF₂H | CH₃ | |
| H | CHFCH₃ | H | Cl | OCF₂H | |
| H | CH₂Br | H | OCH₃ | OCH₃ | |
| H | CH₂Br | H | CH₃ | OCH₃ | |
| H | CH₂Br | H | CH₃ | CH₃ | |

TABLE 3-continued

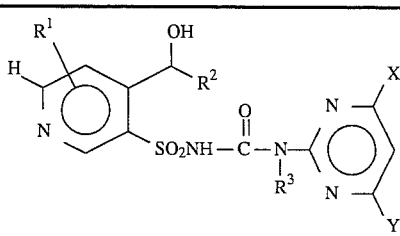

| R¹ | R² | R³ | X | Y | mp (°C.) |
|---|---|---|---|---|---|
| H | CH₂Br | H | Cl | OCH₃ | |
| H | CH₂Br | H | Br | OCH₃ | |
| H | CH₂Br | H | CH₃ | H | |
| H | CH₂Br | H | OCH₃ | H | |
| H | CH₂Br | H | OCH₃ | CH₂OC₂H₅ | |
| H | CH₂Br | H | OCF₂H | OCH₃ | |
| H | CH₂Br | H | OCH₃ | CH(OCH₃)₂ | |
| H | CH₂Br | H | CH₃ | OC₂H₅ | |
| H | CH₂Br | H | CH₃ | CH₂OCH₃ | |
| H | CH₂Br | H | OCH₃ | CH₂OCH₃ | |
| H | CH₂Br | H | OCH₃ | C₂H₅ | |
| H | CH₂Br | H | OC₂H₅ | OCH₃ | |
| H | CH₂Br | H | OCH₂CF₃ | OCH₃ | |
| H | CH₂Br | H | CF₃ | OCH₃ | |
| H | CH₂Br | H | CH₂F | OCH₃ | |
| H | CH₂Br | H | CH₂Cl | OCH₃ | |
| H | CH₂Br | H | CH₂Br | OCH₃ | |
| H | CH₂Br | H | F | OCH₃ | |
| H | CH₂Br | H | I | OCH₃ | |
| H | CH₂Br | H | OCH₂CH₂F | OCH₃ | |
| H | CH₂Br | H | OCH₂CH₂CF₃ | OCH₃ | |
| H | CH₂Br | H | OCH₂CHF₂ | CH₃ | |
| H | CH₂Br | H | OCH₂CF₃ | CH₃ | |
| H | CH₂Br | H | Cl | OC₂H₅ | |
| H | CH₂Br | H | OC₂H₅ | NHCH₃ | |
| H | CH₂Br | H | OCH₃ | CH₂SCH₃ | |
| H | CH₂Br | H | OCF₂H | CH₃ | |
| H | CH₂Br | H | Cl | OCF₂H | |

TABLE 4

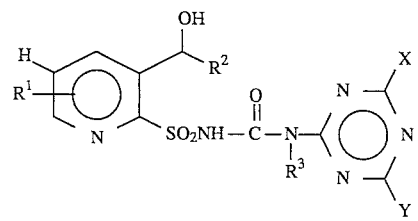

| R¹ | R² | R³ | X | Y | mp (°C.) |
|---|---|---|---|---|---|
| H | CH₂F | H | CH₃ | OCH₃ | 137–139 |
| H | CH₂F | H | OCH₃ | OCH₃ | |
| H | CH₂F | H | OC₂H₅ | NHCH₃ | |
| H | CH₂F | H | OCH₃ | Cl | 138–140 |
| H | CH₂F | H | OCH₃ | N(CH₃)₂ | |
| H | CH₂Cl | H | CH₃ | OCH₃ | 95–97 |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Cl | H | Cl | OCH₃ | 117–120 |
| H | CH₂Br | H | OCH₃ | OCH₃ | |
| H | CH₂Br | H | OC₂H₅ | NHCH₃ | |
| H | CH₂Br | H | OCH₃ | N(OCH₃)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |

TABLE 4-continued

Structure: pyridine with R¹, CH(OH)R², SO₂NH-C(=O)-N(R³)- linked to pyrimidine/triazine with X and Y.

| R¹ | R² | R³ | X | Y | mp (°C.) |
|---|---|---|---|---|---|
| H | CHF₂ | H | OC₂H₅ | NHCH₃ | |
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |
| H | CHF₂ | CH₃ | OCH₃ | OCH₃ | |
| H | CHF₂ | CH₃ | CH₃ | OCH₃ | |
| H | CH₂F | CH₃ | OC₂H₅ | NHCH₃ | |
| H | CH₂F | CH₃ | OCH₃ | N(CH₃)₂ | |
| H | CHFCH₃ | H | CH₃ | OCH₃ | 96–98 |
| H | CHFCH₃ | H | OCH₃ | OCH₃ | |
| H | CHFCH₃ | H | OC₂H₅ | NHCH₃ | |
| H | CHFCH₃ | H | OCH₃ | N(OCH₃)(CH₃) | |
| H | CHFCH₃ | H | OCH₃ | Cl | 112–113 |
| H | CHClCH₃ | H | CH₃ | OCH₃ | |
| H | CHClCH₃ | H | OCH₃ | OCH₃ | |
| H | CHClCH₃ | H | OC₂H₅ | NHCH₃ | |
| H | CHClCH₃ | H | OCH₃ | N(OCH₃)(CH₃) | |
| H | CHClCH₃ | H | OCH₃ | N(CH₃)₂ | |
| H | CH₂CH₂F | H | CH₃ | OCH₃ | |
| H | CH₂CH₂F | H | OCH₃ | OCH₃ | |
| H | CH₂CH₂F | H | OC₂H₅ | NHCH₃ | |
| H | CH₂CH₂F | H | OCH₃ | N(OCH₃)(CH₃) | |
| H | CH₂CH₂F | H | OCH₃ | N(CH₃)₂ | |
| H | CHFCl | H | OCH₃ | OCH₃ | |
| H | CHFCl | H | CH₃ | OCH₃ | |
| H | CHFCl | H | CH₃ | CH₃ | |
| H | CHFCl | H | Cl | OCH₃ | |
| H | CHFCl | H | OCH₃ | CH₂OCH₃ | |
| H | CHFCl | H | CH₃ | OC₂H₅ | |
| H | CHFCl | H | CH₂Cl | OCH₃ | |
| H | CHFCl | H | F | OCH₃ | |
| H | CHFCl | H | OCH₃ | CH(OCH₃)₂ | |
| H | CHFCl | H | OCHF₂ | OCH₃ | |
| H | CHFCH₂CH₃ | H | CH₃ | OCH₃ | 89–91 |
| 6-F | CH₂F | H | CH₃ | OCH₃ | |
| 6-Cl | CH₂F | H | OCH₃ | CH₃ | |
| 6-Br | CH₂F | H | CH₃ | OCH₃ | |
| 6-CH₂CN | CH₂F | H | OCH₃ | OCH₃ | |
| 6-OCH₃ | CH₂F | H | CH₃ | OCH₃ | |
| 6-SCH₃ | CH₂F | H | CH₃ | OCH₃ | |
| 6-OCF₂H | CH₂F | H | CH₃ | OCH₃ | |
| 6-Cl | CH₂Cl | H | CH₃ | OCH₃ | |
| 6-Cl | CH₂Br | H | OCH₃ | OCH₃ | |
| 6-Cl | CH₂F | H | OC₂H₅ | NHCH₃ | |
| 6-Cl | CH₂F | H | OCH₃ | OCH₃ | |

TABLE 5

Structure: benzene ring with R¹, CH(OH)R², SO₂NH-C(=O)-N(R³)- linked to pyrimidine/triazine with X and Y.

| R¹ | R² | R³ | X | Y | mp (°C.) |
|---|---|---|---|---|---|
| H | CH₂F | H | CH₃ | OCH₃ | 148–150 |
| H | CH₂F | H | OCH₃ | OCH₃ | |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |

| R¹ | R² | R³ | X | Y |
|---|---|---|---|---|
| H | CH₂Br | H | CH₃ | OCH₃ |
| H | CH₂Br | H | OCH₃ | OCH₃ |
| H | CH₂Br | H | OC₂H₅ | NHCH₃ |
| H | CH₂Br | H | OCH₃ | N(OCH₃)(CH₃) |
| H | CH₂Br | H | OCH₃ | N(CH₃)₂ |
| H | CHF₂ | H | CH₃ | OCH₃ |
| H | CHF₂ | H | OCH₃ | OCH₃ |
| H | CHF₂ | H | OC₂H₅ | NHCH₃ |
| H | CHF₂ | H | OCH₃ | N(OCH₃)(CH₃) |
| H | CHF₂ | H | OCH₃ | N(CH₃)₂ |
| H | CH₂F | CH₃ | OCH₃ | OCH₃ |
| H | CH₂Cl | CH₃ | OCH₃ | OCH₃ |
| H | CH₂F | CH₃ | CH₃ | OCH₃ |
| H | CH₂Br | CH₃ | OCH₃ | OCH₃ |
| H | CH₂Cl | CH₃ | CH₃ | OCH₃ |
| H | CH₂Br | CH₃ | CH₃ | OCH₃ |
| H | CHF₂ | CH₃ | OCH₃ | OCH₃ |
| H | CHF₂ | CH₃ | CH₃ | OCH₃ |
| H | CH₂F | CH₃ | OC₂H₅ | NHCH₃ |
| H | CH₂F | CH₃ | OCH₃ | N(CH₃)₂ |
| H | CHFCH₃ | H | CH₃ | OCH₃ |
| H | CHFCH₃ | H | OCH₃ | OCH₃ |
| H | CHFCH₃ | H | OC₂H₅ | NHCH₃ |
| H | CHFCH₃ | H | OCH₃ | N(OCH₃)(CH₃) |
| H | CHFCH₃ | H | OCH₃ | N(CH₃)₂ |
| H | CHClCH₃ | H | CH₃ | OCH₃ |
| H | CHClCH₃ | H | OCH₃ | OCH₃ |
| H | CHClCH₃ | H | OC₂H₅ | NHCH₃ |
| H | CHClCH₃ | H | OCH₃ | N(OCH₃)(CH₃) |
| H | CHClCH₃ | H | OCH₃ | N(CH₃)₂ |
| H | CH₂CH₂F | H | CH₃ | OCH₃ |
| H | CH₂CH₂F | H | OCH₃ | OCH₃ |
| H | CH₂CH₂F | H | OC₂H₅ | NHCH₃ |
| H | CH₂CH₂F | H | OCH₃ | N(OCH₃)(CH₃) |
| H | CH₂CH₂F | H | OCH₃ | N(CH₃)₂ |
| H | CHFCl | H | OCH₃ | OCH₃ |
| H | CHFCl | H | CH₃ | OCH₃ |
| H | CHFCl | H | CH₃ | CH₃ |
| H | CHFCl | H | Cl | OCH₃ |
| H | CHFCl | H | OCH₃ | CH₂OCH₃ |
| H | CHFCl | H | CH₃ | OC₂H₅ |
| H | CHFCl | H | CH₂Cl | OCH₃ |
| H | CHFCl | H | F | OCH₃ |
| H | CHFCl | H | OCH₃ | CH(OCH₃)₂ |
| H | CHFCl | H | OCHF₂ | OCH₃ |
| H | CHFCl | H | C₂H₅ | OCH₃ |
| 5-F | CH₂F | H | CH₃ | OCH₃ |

TABLE 6

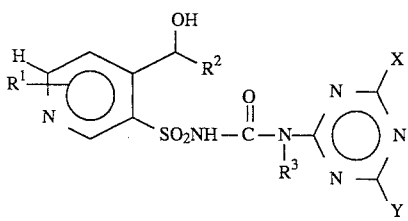

| R¹ | R² | R³ | X | Y | mp (°C.) |
|---|---|---|---|---|---|
| H | CH₂F | H | CH₃ | OCH₃ | |
| H | CH₂F | H | OCH₃ | OCH₃ | |
| H | CH₂F | H | OC₂H₅ | NHCH₃ | |
| H | CH₂F | H | OCH₃ | N(OCH₃)(CH₃) | |
| H | CH₂F | H | OCH₃ | N(CH₃)₂ | |
| H | CH₂Cl | H | CH₃ | OCH₃ | |
| H | CH₂Cl | H | OCH₃ | OCH₃ | |
| H | CH₂Cl | H | OC₂H₅ | NHCH₃ | |
| H | CH₂Cl | H | OCH₃ | N(OCH₃)(CH₃) | |
| H | CH₂Cl | H | OCH₃ | N(CH₃)₂ | |
| H | CH₂Br | H | CH₃ | OCH₃ | |
| H | CH₂Br | H | OCH₃ | OCH₃ | |
| H | CH₂Br | H | OC₂H₅ | NHCH₃ | |
| H | CH₂Br | H | OCH₃ | N(OCH₂)(CH₃) | |
| H | CH₂Br | H | OCH₃ | N(CH₃)₂ | |
| H | CHF₂ | H | CH₃ | OCH₃ | |
| H | CHF₂ | H | OCH₃ | OCH₃ | |
| H | CHF₂ | H | OC₂H₅ | NHCH₃ | |

TABLE 6-continued

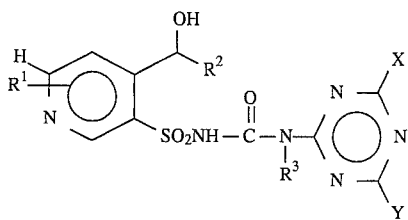

| R¹ | R² | R³ | X | Y | mp (°C.) |
|---|---|---|---|---|---|
| H | CHF₂ | H | OCH₃ | N(OCH₃)(CH₃) | |
| H | CHF₂ | H | OCH₃ | N(CH₃)₂ | |
| H | CH₂F | CH₃ | OCH₃ | OCH₃ | |
| H | CH₂Cl | CH₃ | OCH₃ | OCH₃ | |
| H | CH₂F | CH₃ | CH₃ | OCH₃ | |
| H | CH₂Br | CH₃ | OCH₃ | OCH₃ | |
| H | CH₂Cl | CH₃ | CH₃ | OCH₃ | |
| H | CH₂Br | CH₃ | CH₃ | OCH₃ | |

TABLE 7

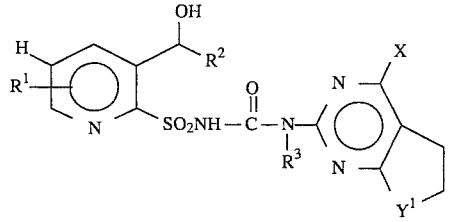

| R¹ | R² | R³ | X¹ | Y¹ | mp (°C.) |
|---|---|---|---|---|---|
| H | CH₂F | H | CH₃ | O | |
| H | CH₂F | H | OCH₃ | O | |
| H | CH₂F | H | OC₂H₅ | O | |
| H | CH₂F | H | OCF₂H | O | |
| H | CH₂F | H | OCH₃ | CH₂ | |
| H | CH₂Cl | H | CH₃ | O | |
| H | CH₂Cl | H | OCH₃ | O | |
| H | CH₂Br | H | CH₃ | O | |
| H | CHFCH₃ | H | CH₃ | O | |
| H | CHClCH₃ | H | CH₃ | O | |
| 6-CH₃ | CH₂F | H | CH₃ | O | |
| 6-Cl | CH₂F | H | CH₃ | O | |
| 4-CH₃ | CH₂F | H | CH₃ | O | |
| 6-CH₂CN | CH₂F | H | CH₃ | O | |
| H | CH₂F | CH₃ | CH₃ | O | |
| H | CHF₂ | H | OCH₃ | O | |

TABLE 8

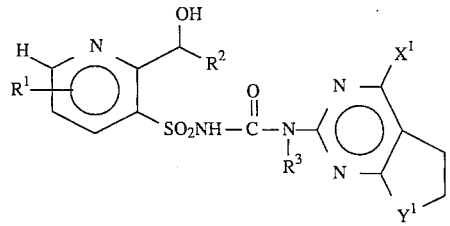

| R¹ | R² | R³ | X¹ | Y¹ | mp (°C.) |
|---|---|---|---|---|---|
| H | CH₂F | H | CH₃ | O | |
| H | CH₂F | H | OCH₃ | O | |
| H | CH₂F | H | OC₂H₅ | O | |
| H | CH₂F | H | OCF₂H | O | |
| H | CH₂F | H | OCH₃ | CH₂ | |
| H | CH₂Cl | H | CH₃ | O | |

TABLE 8-continued

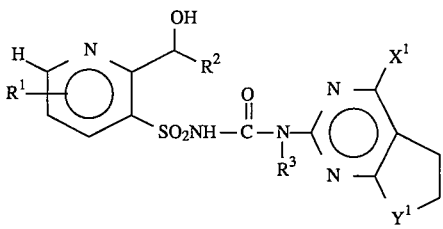

| R¹ | R² | R³ | X¹ | Y¹ | mp (°C.) |
|---|---|---|---|---|---|
| H | CH₂Cl | H | OCH₃ | O | |
| H | CH₂Br | H | CH₃ | O | |
| H | CHFCH₃ | H | CH₃ | O | |
| H | CHClCH₃ | H | CH₃ | O | |
| 5-CH₃ | CH₂F | H | CH₃ | O | |
| 5-Cl | CH₂F | H | CH₃ | O | |
| 5-CH₃ | CH₂F | H | CH₃ | O | |
| 5-CH₂CN | CH₂F | H | CH₃ | O | |
| H | CH₂F | CH₃ | CH₃ | O | |
| H | CHF₂ | H | OCH₃ | O | |

TABLE 9

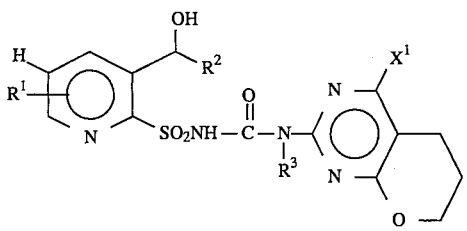

| R¹ | R² | R³ | X¹ | Y³ | mp (°C.) |
|---|---|---|---|---|---|
| H | CH₂F | H | CH₃ | CH₃ | |
| H | CH₂F | H | OCH₃ | CH₃ | |
| H | CH₂F | H | OC₂H₅ | CH₃ | |
| H | CH₂F | H | OCF₂H | CH₃ | |
| H | CH₂F | H | OCH₃ | H | |
| H | CH₂F | H | CH₃ | H | |
| H | CH₂Cl | H | OCH₃ | OCH₃ | |
| H | CHFCl | H | OCH₃ | OCH₃ | |
| H | CHFCl | H | OCH₃ | CH₃ | |
| H | CHFCH₃ | H | OCH₃ | OCH₃ | |
| H | CHF₂ | H | OCH₃ | OCH₃ | |
| 6-F | CH₂F | H | OCH₃ | OCH₃ | |
| 6-OCH₃ | CH₂F | H | OCH₃ | OCH₃ | |
| 6-Cl | CH₂F | H | OCH₃ | OCH₃ | |
| 6-CH₃ | CH₂F | H | OCH₃ | OCH₃ | |
| 6-CH₂CN | CH₂F | H | OCH₃ | CH₃ | |
| H | CH₂Cl | H | OCH₃ | CH₃ | |
| H | CH₂Br | H | OCH₃ | CH₃ | |
| H | CH₂CH₂F | H | OCH₃ | CH₃ | |
| H | CHClCH₃ | H | OCH₃ | CH₃ | |
| H | CHF₂ | CH₃ | OCH₃ | CH₃ | |
| 6-Cl | CH₂F | H | OCH₃ | CH₃ | |

TABLE 10

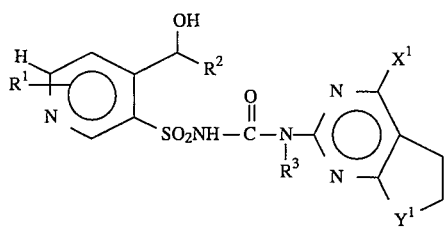

| R¹ | R² | R³ | X¹ | Y¹ | mp (°C.) |
|---|---|---|---|---|---|
| H | CH₂F | H | CH₃ | O | |
| H | CH₂F | H | OCH₃ | O | |
| H | CH₂F | H | OC₂H₅ | O | |
| H | CH₂F | H | OCF₂H | O | |
| H | CH₂F | H | OCH₃ | CH₂ | |
| H | CH₂Cl | H | CH₃ | O | |
| H | CH₂Cl | H | OCH₃ | O | |
| H | CH₂Br | H | CH₃ | O | |
| H | CHFCH₃ | H | CH₃ | O | |
| H | CHClCH₃ | H | CH₃ | O | |
| 2-CH₃ | CH₂F | H | CH₃ | O | |
| 2-Cl | CH₂F | H | CH₃ | O | |
| 2-CH₃ | CH₂F | H | CH₃ | O | |
| 2-CH₂CN | CH₂F | H | CH₃ | O | |
| H | CH₂F | H | CH₃ | O | |
| H | CHF₂ | H | OCH₃ | O | |

TABLE 11

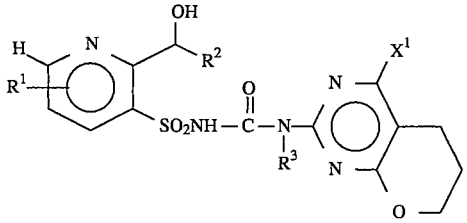

| R¹ | R² | R³ | X¹ | Y³ | mp (°C.) |
|---|---|---|---|---|---|
| H | CH₂F | H | CH₃ | CH₃ | |
| H | CH₂F | H | OCH₃ | CH₃ | |
| H | CH₂F | H | OC₂H₅ | CH₃ | |
| H | CH₂F | H | OCF₂H | CH₃ | |
| H | CH₂F | H | OCH₃ | H | |
| H | CH₂F | H | CH₃ | H | |
| H | CH₂Cl | H | OCH₃ | OCH₃ | |
| H | CHFCl | H | OCH₃ | OCH₃ | |
| H | CHFCl | H | OCH₃ | CH₃ | |
| H | CHFCH₃ | H | OCH₃ | OCH₃ | |
| H | CH₂F | H | OCH₃ | OCH₃ | |
| 5-F | CH₂F | H | OCH₃ | OCH₃ | |
| 5-OCH₃ | CH₂F | H | OCH₃ | OCH₃ | |
| 5-Cl | CH₂F | H | OCH₃ | OCH₃ | |
| 5-CH₃ | CH₂F | H | OCH₃ | OCH₃ | |
| 5-CH₂CN | CH₂F | H | OCH₃ | CH₃ | |
| H | CH₂Cl | H | OCH₃ | CH₃ | |
| H | CH₂Br | H | OCH₃ | CH₃ | |
| H | CH₂CH₂F | H | OCH₃ | CH₃ | |
| H | CHClCH₃ | H | OCH₃ | CH₃ | |
| H | CHF₂ | H | OCH₃ | CH₃ | |
| 4-Cl | CH₂F | H | OCH₃ | CH₃ | |

TABLE 12

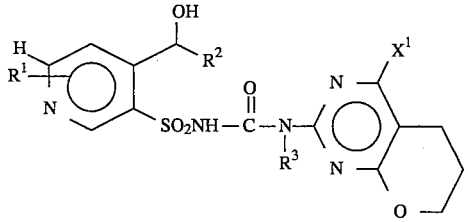

| R¹ | R² | R³ | X¹ | mp (°C.) |
|---|---|---|---|---|
| H | CH₂F | H | CH₃ | |
| H | CH₂F | H | OCH₃ | |
| H | CH₂F | H | OC₂H₅ | |
| H | CH₂F | H | OCF₂H | |
| H | CH₂Cl | H | CH₃ | |

TABLE 12-continued

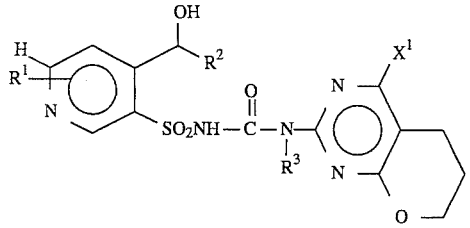

| R¹ | R² | R³ | X¹ | mp (°C.) |
|---|---|---|---|---|
| H | CH₂Cl | H | OCH₃ | |
| H | CH₂Br | H | CH₃ | |
| H | CHF₂ | H | CH₃ | |
| H | CHF₂ | H | OCH₃ | |
| H | CHFCH₃ | H | CH₃ | |
| H | CHFCH₃ | H | OCH₃ | |
| H | CHFCl | H | OCH₃ | |
| H | CHFCl | H | CH₃ | |
| 2-Cl | CHFCl | H | CH₃ | |
| 2-Cl | CHFCl | H | OCH₃ | |
| 2-Cl | CH₂F | H | CH₃ | |
| 2-Cl | CH₂F | H | OCH₃ | |
| 2-CH₃ | CH₂F | H | CH₃ | |
| 2-OCH₃ | CH₂F | H | CH₃ | |
| H | CH₂F | CH₃ | CH₃ | |
| H | CH₂F | CH₃ | OCH₃ | |
| H | CHClCH₃ | H | OCH₃ | |
| H | CH₂CH₂F | H | OCH₃ | |

TABLE 13

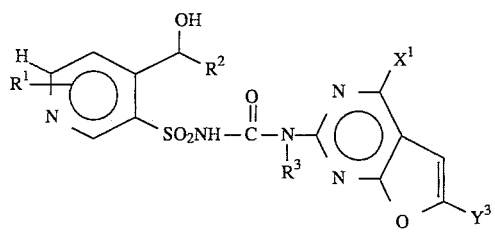

| R¹ | R² | R³ | X¹ | Y³ | mp (°C.) |
|---|---|---|---|---|---|
| H | CH₂F | H | CH₃ | CH₃ | |
| H | CH₂F | H | OCH₃ | CH₃ | |
| H | CH₂F | H | OC₂H₅ | CH₃ | |
| H | CH₂F | H | OCF₂H | CH₃ | |
| H | CH₂F | H | OCH₃ | H | |
| H | CH₂F | H | CH₃ | H | |
| H | CH₂Cl | H | OCH₃ | OCH₃ | |
| H | CHFCl | H | OCH₃ | OCH₃ | |
| H | CHFCl | H | OCH₃ | CH₃ | |
| H | CHFCH₃ | H | OCH₃ | OCH₃ | |
| H | CH₂F | H | OCH₃ | OCH₃ | |
| 2-F | CH₂F | H | OCH₃ | OCH₃ | |
| 2-OCH₃ | CH₂F | H | OCH₃ | OCH₃ | |
| 2-Cl | CH₂F | H | OCH₃ | OCH₃ | |
| 2-CH₃ | CH₂F | H | OCH₃ | OCH₃ | |
| 2-CH₃ | CH₂F | H | OCH₃ | CH₃ | |
| H | CH₂Cl | H | OCH₃ | CH₃ | |
| H | CH₂Br | H | OCH₃ | CH₃ | |
| H | CH₂CH₂F | H | OCH₃ | CH₃ | |
| H | CHClCH₃ | H | OCH₃ | CH₃ | |
| H | CHF₂ | H | OCH₃ | CH₃ | |
| 5-Cl | CH₂F | H | OCH₃ | CH₃ | |

TABLE 14

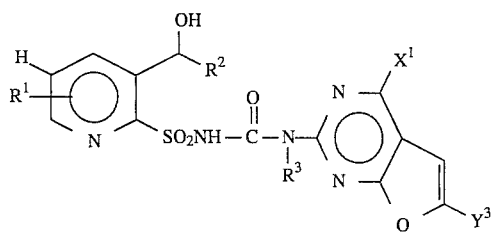

| R¹ | R² | R³ | X¹ | Y³ | mp (°C.) |
|---|---|---|---|---|---|
| H | CH₂F | H | CH₃ | CH₃ | |
| H | CH₂F | H | OCH₃ | CH₃ | |
| H | CH₂F | H | OC₂H₅ | CH₃ | |
| H | CH₂F | H | OCF₂H | CH₃ | |
| H | CH₂F | H | OCH₃ | H | |
| H | CH₂F | H | CH₃ | H | |
| H | CH₂Cl | H | OCH₃ | OCH₃ | |
| H | CHFCl | H | OCH₃ | OCH₃ | |
| H | CHFCl | H | OCH₃ | CH₃ | |
| H | CHFCH₃ | H | OCH₃ | OCH₃ | |
| H | CH₂F | H | OCH₃ | OCH₃ | |
| 6-F | CH₂F | H | OCH₃ | OCH₃ | |
| 6-OCH₃ | CH₂F | H | OCH₃ | OCH₃ | |
| 6-Cl | CH₂F | H | OCH₃ | OCH₃ | |
| 4-CH₃ | CH₂F | H | OCH₃ | OCH₃ | |
| 6-CH₂CN | CH₂F | H | OCH₃ | CH₃ | |
| H | CH₂Cl | H | OCH₃ | CH₃ | |
| H | CH₂Br | H | OCH₃ | CH₃ | |
| H | CH₂CH₂F | H | OCH₃ | CH₃ | |
| H | CHClCH₃ | H | OCH₃ | CH₃ | |
| H | CHF₂ | H | OCH₃ | CH₃ | |
| 6-Cl | CH₂F | H | OCH₃ | CH₃ | |

TABLE 15

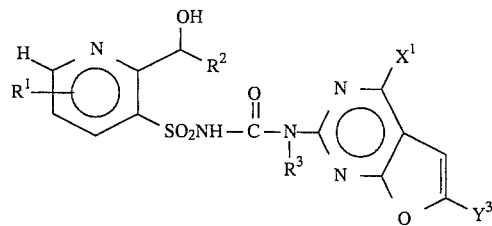

| R¹ | R² | R³ | X¹ | Y³ | mp (°C.) |
|---|---|---|---|---|---|
| H | CH₂F | H | CH₃ | CH₃ | |
| H | CH₂F | H | OCH₃ | CH₃ | |
| H | CH₂F | H | OC₂H₅ | CH₃ | |
| H | CH₂F | H | OCF₂H | CH₃ | |
| H | CH₂F | H | OCH₃ | H | |
| H | CH₂F | H | CH₃ | H | |
| H | CH₂Cl | H | OCH₃ | OCH₃ | |
| H | CHFCl | H | OCH₃ | OCH₃ | |
| H | CHFCl | H | OCH₃ | CH₃ | |
| H | CHFCH₃ | H | OCH₃ | OCH₃ | |
| H | CH₂F | H | OCH₃ | OCH₃ | |
| 5-F | CH₂F | H | OCH₃ | OCH₃ | |
| 5-OCH₃ | CH₂F | H | OCH₃ | OCH₃ | |
| 5-Cl | CH₂F | H | OCH₃ | OCH₃ | |
| 5-CH₃ | CH₂F | H | OCH₃ | OCH₃ | |
| 5-CH₂CN | CH₂F | H | OCH₃ | CH₃ | |
| H | CH₂Cl | H | OCH₃ | CH₃ | |
| H | CH₂Br | H | OCH₃ | CH₃ | |
| H | CH₂CH₂F | H | OCH₃ | CH₃ | |
| H | CHClCH₃ | H | OCH₃ | CH₃ | |
| H | CHF₂ | H | OCH₃ | CH₃ | |
| 5-Cl | CH₂F | H | OCH₃ | CH₃ | |

TABLE 16

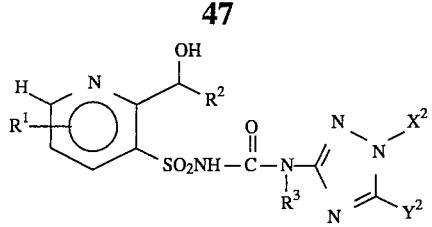

| R¹ | R² | R³ | X² | Y² | mp (°C.) |
|---|---|---|---|---|---|
| H | CH₂F | H | CH₃ | OCH₃ | |
| H | CH₂F | H | CH₃ | OC₂H₅ | |
| H | CH₂F | H | CH₃ | SCH₃ | |
| H | CH₂F | H | CH₃ | SC₂H₅ | |
| H | CH₂F | H | CH₃ | CH₃ | |
| H | CH₂F | H | CH₃ | C₂H₅ | |
| H | CH₂F | H | C₂H₅ | OCH₃ | |
| H | CH₂F | H | CH₂CF₃ | OCH₃ | |
| H | CH₂Cl | H | CH₃ | OCH₃ | |
| H | CHFCl | H | CH₃ | OCH₃ | |
| H | CHF₂ | H | CH₃ | OCH₃ | |
| 5-CH₃ | CH₂F | H | CH₃ | OCH₃ | |
| 5-F | CH₂F | H | CH₃ | OCH₃ | |
| 5-Cl | CH₂F | H | CH₃ | OCH₃ | |
| 5-OCH₃ | CH₂F | H | CH₃ | OCH₃ | |
| 5-Cl | CH₂F | H | CH₃ | CH₃ | |
| 5-CH₂CN | CH₂F | H | CH₃ | OCH₃ | |
| H | CH₂Br | H | CH₃ | OCH₃ | |
| H | CH₂CH₂F | H | CH₃ | OCH₃ | |
| H | CHFCl | H | CH₃ | CH₃ | |
| H | CHFCH₃ | H | CH₃ | OCH₃ | |
| H | CHClCH₃ | H | CH₃ | OCH₃ | |

TABLE 17

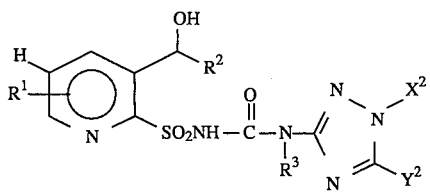

| R¹ | R² | R³ | X² | Y² | mp (°C.) |
|---|---|---|---|---|---|
| H | CH₂F | H | CH₃ | OCH₃ | |
| H | CH₂F | H | CH₃ | OC₂H₅ | |
| H | CH₂F | H | CH₃ | SCH₃ | |
| H | CH₂F | H | CH₃ | SC₂H₅ | |
| H | CH₂F | H | CH₃ | CH₃ | |
| H | CH₂F | H | CH₃ | C₂H₅ | |
| H | CH₂F | H | C₂H₅ | OCH₃ | |
| H | CH₂F | H | CH₂CF₃ | OCH₃ | |
| H | CH₂Cl | H | CH₃ | OCH₃ | |
| H | CHFCl | H | CH₃ | OCH₃ | |
| H | CHF₂ | H | CH₃ | OCH₃ | |
| 6-CH₃ | CH₂F | H | CH₃ | OCH₃ | |
| 6-F | CH₂F | H | CH₃ | OCH₃ | |
| 6-Cl | CH₂F | H | CH₃ | OCH₃ | |
| 6-OCH₃ | CH₂F | H | CH₃ | OCH₃ | |
| 6-Cl | CH₂F | H | CH₃ | CH₃ | |
| 6-CH₂CN | CH₂F | H | CH₃ | OCH₃ | |
| H | CH₂Br | H | CH₃ | OCH₃ | |
| H | CH₂CH₂F | H | CH₃ | OCH₃ | |
| H | CHFCl | H | CH₃ | CH₃ | |
| H | CHFCH₃ | H | CH₃ | OCH₃ | |
| H | CHClCH₃ | H | CH₃ | OCH₃ | |

TABLE 18

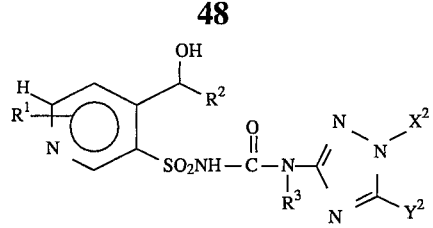

| R¹ | R² | R³ | X² | Y² | mp (°C.) |
|---|---|---|---|---|---|
| H | CH₂F | H | CH₃ | OCH₃ | |
| H | CH₂F | H | CH₃ | OC₂H₅ | |
| H | CH₂F | H | CH₃ | SCH₃ | |
| H | CH₂F | H | CH₃ | SC₂H₅ | |
| H | CH₂F | H | CH₃ | CH₃ | |
| H | CH₂F | H | CH₃ | C₂H₅ | |
| H | CH₂F | H | C₂H₅ | OCH₃ | |
| H | CH₂F | H | CH₂CF₃ | OCH₃ | |
| H | CH₂Cl | H | CH₃ | OCH₃ | |
| H | CHFCl | H | CH₃ | OCH₃ | |
| H | CHF₂ | H | CH₃ | OCH₃ | |
| 2-CH₃ | CH₂F | H | CH₃ | OCH₃ | |
| 2-F | CH₂F | H | CH₃ | OCH₃ | |
| 2-Cl | CH₂F | H | CH₃ | OCH₃ | |
| 2-OCH₃ | CH₂F | H | CH₃ | OCH₃ | |
| 2-Cl | CH₂F | H | CH₃ | CH₃ | |
| 2-CH₂CN | CH₂F | H | CH₃ | OCH₃ | |
| H | CH₂Br | H | CH₃ | OCH₃ | |
| H | CH₂CH₂F | H | CH₃ | OCH₃ | |
| H | CHFCl | H | CH₃ | CH₃ | |
| H | CHFCH₃ | H | CH₃ | OCH₃ | |
| H | CHClCH₃ | H | CH₃ | OCH₃ | |

TABLE 19

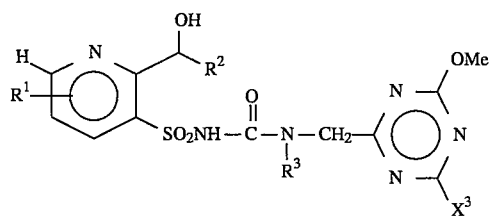

| R¹ | R² | R³ | X³ | mp (°C.) |
|---|---|---|---|---|
| H | CH₂F | H | CH₃ | |
| H | CH₂F | H | OCH₃ | |
| H | CH₂Cl | H | CH₃ | |
| H | CH₂Cl | H | OCH₃ | |
| H | CHF₂ | H | OCH₃ | |
| H | CHF₂ | H | CH₃ | |
| H | CHFCl | H | CH₃ | |
| H | CHFCl | H | OCH₃ | |
| H | CHFCH₃ | H | CH₃ | |
| H | CHFCH₃ | H | OCH₃ | |
| H | CHClCH₃ | H | OCH₃ | |
| 5-F | CH₂F | H | OCH₃ | |
| 5-Cl | CH₂F | H | OCH₃ | |
| 5-CH₃ | CH₂F | H | CH₃ | |
| 5-OCH₃ | CH₂F | H | CH₃ | |
| 5-CH₂CN | CH₂F | H | CH₃ | |
| 5-Cl | CH₂F | H | OCH₃ | |
| H | CH₂CH₂F | H | OCH₃ | |
| H | CH₂F | CH₃ | OCH₃ | |
| H | CH₂CH₂F | H | CH₃ | |

TABLE 20

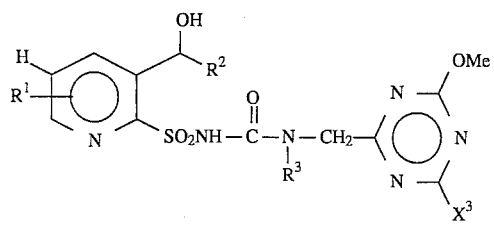

| R¹ | R² | R³ | X³ | mp (°C.) |
|---|---|---|---|---|
| H | CH₂F | H | CH₃ | |
| H | CH₂F | H | OCH₃ | |
| H | CH₂Cl | H | CH₃ | |
| H | CH₂Cl | H | OCH₃ | |
| H | CHF₂ | H | OCH₃ | |
| H | CHF₂ | H | CH₃ | |
| H | CHFCl | H | CH₃ | |
| H | CHFCl | H | OCH₃ | |
| H | CHFCH₃ | H | CH₃ | |
| H | CHFCH₃ | H | OCH₃ | |
| H | CHClCH₃ | H | OCH₃ | |
| 6-F | CH₂F | H | OCH₃ | |
| 6-Cl | CH₂F | H | OCH₃ | |
| 6-CH₃ | CH₂F | H | CH₃ | |
| 6-OCH₃ | CH₂F | H | CH₃ | |
| 6-CH₂CN | CH₂F | H | CH₃ | |
| 6-Cl | CH₂F | H | OCH₃ | |
| H | CH₂CH₂F | H | OCH₃ | |
| H | CH₂F | CH₃ | OCH₃ | |
| H | CH₂CH₂F | H | CH₃ | |

TABLE 21

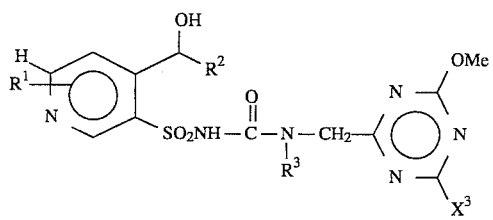

| R¹ | R² | R³ | X³ | mp (°C.) |
|---|---|---|---|---|
| H | CH₂F | H | CH₃ | |
| H | CH₂F | H | OCH₃ | |
| H | CH₂Cl | H | CH₃ | |
| H | CH₂Cl | H | OCH₃ | |
| H | CHF₂ | H | OCH₃ | |
| H | CHF₂ | H | CH₃ | |
| H | CHFCl | H | CH₃ | |
| H | CHFCl | H | OCH₃ | |
| H | CHFCH₃ | H | CH₃ | |
| H | CHFCH₃ | H | OCH₃ | |
| H | CHClCH₃ | H | OCH₃ | |
| 2-F | CH₂F | H | OCH₃ | |
| 2-Cl | CH₂F | H | OCH₃ | |
| 2-CH₃ | CH₂F | H | CH₃ | |
| 2-OCH₃ | CH₂F | H | CH₃ | |
| 2-CH₂CN | CH₂F | H | CH₃ | |
| 2-Cl | CH₂F | H | OCH₃ | |
| H | CH₂CH₂F | H | OCH₃ | |
| H | CH₂F | CH₃ | OCH₃ | |
| H | CH₂CH₂F | H | CH₃ | |

TABLE 22

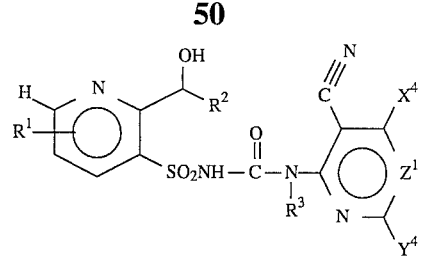

| R¹ | R² | R³ | X⁴ | Y⁴ | Z¹ | mp (°C.) |
|---|---|---|---|---|---|---|
| H | CH₂F | H | CH₃ | CH₃ | CH | |
| H | CH₂F | H | CH₃ | CH₃ | N | |
| H | CH₂F | H | OCH₃ | CH₃ | CH | |
| H | CH₂F | H | OCH₃ | CH₃ | N | |
| H | CH₂F | H | OCH₃ | OCH₃ | CH | |
| H | CH₂F | H | OCH₃ | OCH₃ | N | |
| H | CH₂F | H | Cl | CH₃ | CH | |
| H | CH₂F | H | OCH₃ | Cl | CH | |
| H | CH₂F | H | OC₂H₅ | CH₃ | CH | |
| H | CH₂F | H | CH₂OCH₃ | CH₃ | N | |
| H | CH₂F | H | CH₂OCH₃ | OCH₃ | CH | |
| H | CH₂F | H | OC₂H₅ | OC₂H₅ | N | |
| H | CH₂Cl | H | OCH₃ | CH₃ | CH | |
| H | CH₂Cl | H | OCH₃ | OCH₃ | CH | |
| H | CH₂Cl | H | OCH₃ | CH₃ | N | |
| H | CH₂Cl | H | OCH₃ | OCH₃ | N | |
| H | CHF₂ | H | OCH₃ | CH₃ | CH | |
| H | CHFCl | H | OCH₃ | CH₃ | CH | |
| H | CHFCH₃ | H | OCH₃ | CH₃ | CH | |
| H | CHClCH₃ | H | OCH₃ | CH₃ | CH | |
| 5-F | CH₂F | H | OCH₃ | CH₃ | CH | |
| 5-CH₃ | CH₂F | H | OCH₃ | CH₃ | CH | |
| 5-OCH₃ | CH₂F | H | OCH₃ | CH₃ | CH | |
| 5-Cl | CH₂F | H | OCH₃ | CH₃ | CH | |
| 5-CH₂CN | CH₂F | H | OCH₃ | CH₃ | CH | |
| H | CH₂F | CH₃ | OCH₃ | CH₃ | CH | |
| H | CH₂CH₂F | H | OCH₃ | CH₃ | CH | |
| H | CH₂CH₂Cl | H | OCH₃ | CH₃ | CH | |
| H | CHFCl | H | OCH₃ | OCH₃ | CH | |

TABLE 23

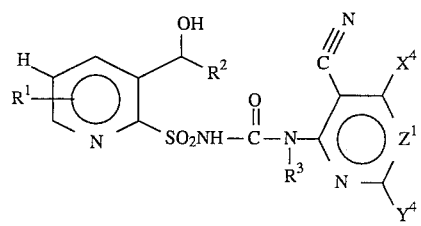

| R¹ | R² | R³ | X⁴ | Y⁴ | Z¹ | mp (°C.) |
|---|---|---|---|---|---|---|
| H | CH₂F | H | CH₃ | CH₃ | CH | |
| H | CH₂F | H | CH₃ | CH₃ | N | |
| H | CH₂F | H | OCH₃ | CH₃ | CH | |
| H | CH₂F | H | OCH₃ | CH₃ | N | |
| H | CH₂F | H | OCH₃ | OCH₃ | CH | |
| H | CH₂F | H | OCH₃ | OCH₃ | N | |
| H | CH₂F | H | Cl | CH₃ | CH | |
| H | CH₂F | H | OCH₃ | Cl | CH | |
| H | CH₂F | H | OC₂H₅ | CH₃ | CH | |
| H | CH₂F | H | CH₂OCH₃ | CH₃ | N | |
| H | CH₂F | H | CH₂OCH₃ | OCH₃ | CH | |
| H | CH₂F | H | OC₂H₅ | OC₂H₅ | N | |
| H | CH₂Cl | H | OCH₃ | CH₃ | CH | |
| H | CH₂Cl | H | OCH₃ | OCH₃ | CH | |
| H | CH₂Cl | H | OCH₃ | CH₃ | N | |
| H | CH₂Cl | H | OCH₃ | OCH₃ | N | |
| H | CHF₂ | H | OCH₃ | CH₃ | CH | |
| H | CHFCl | H | OCH₃ | CH₃ | CH | |
| H | CHFCH₃ | H | OCH₃ | CH₃ | CH | |
| H | CHClCH₃ | H | OCH₃ | CH₃ | CH | |

TABLE 23-continued

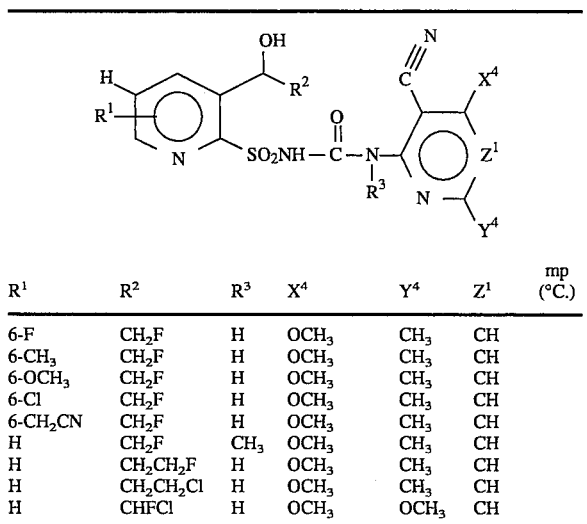

| R¹ | R² | R³ | X⁴ | Y⁴ | Z¹ | mp (°C.) |
|---|---|---|---|---|---|---|
| 6-F | CH₂F | H | OCH₃ | CH₃ | CH | |
| 6-CH₃ | CH₂F | H | OCH₃ | CH₃ | CH | |
| 6-OCH₃ | CH₂F | H | OCH₃ | CH₃ | CH | |
| 6-Cl | CH₂F | H | OCH₃ | CH₃ | CH | |
| 6-CH₂CN | CH₂F | H | OCH₃ | CH₃ | CH | |
| H | CH₂F | CH₃ | OCH₃ | CH₃ | CH | |
| H | CH₂CH₂F | H | OCH₃ | CH₃ | CH | |
| H | CH₂CH₂Cl | H | OCH₃ | CH₃ | CH | |
| H | CHFCl | H | OCH₃ | OCH₃ | CH | |

TABLE 24

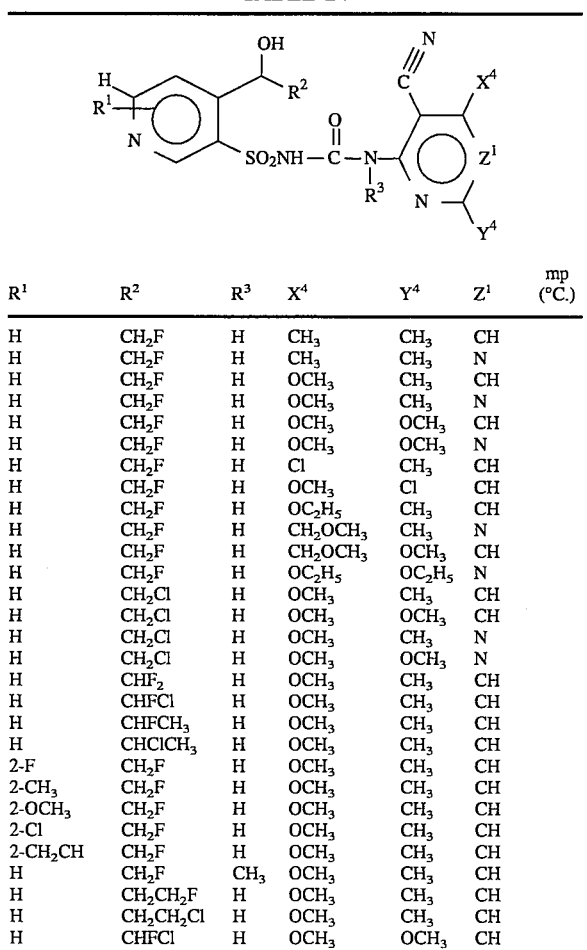

| R¹ | R² | R³ | X⁴ | Y⁴ | Z¹ | mp (°C.) |
|---|---|---|---|---|---|---|
| H | CH₂F | H | CH₃ | CH₃ | CH | |
| H | CH₂F | H | CH₃ | CH₃ | N | |
| H | CH₂F | H | OCH₃ | CH₃ | CH | |
| H | CH₂F | H | OCH₃ | CH₃ | N | |
| H | CH₂F | H | OCH₃ | OCH₃ | CH | |
| H | CH₂F | H | OCH₃ | OCH₃ | N | |
| H | CH₂F | H | Cl | CH₃ | CH | |
| H | CH₂F | H | OCH₃ | Cl | CH | |
| H | CH₂F | H | OC₂H₅ | CH₃ | CH | |
| H | CH₂F | H | CH₂OCH₃ | CH₃ | N | |
| H | CH₂F | H | CH₂OCH₃ | OCH₃ | CH | |
| H | CH₂F | H | OC₂H₅ | OC₂H₅ | CH | |
| H | CH₂Cl | H | OCH₃ | CH₃ | CH | |
| H | CH₂Cl | H | OCH₃ | OCH₃ | CH | |
| H | CH₂Cl | H | OCH₃ | CH₃ | N | |
| H | CH₂Cl | H | OCH₃ | OCH₃ | N | |
| H | CHF₂ | H | OCH₃ | CH₃ | CH | |
| H | CHFCl | H | OCH₃ | CH₃ | CH | |
| H | CHFCH₃ | H | OCH₃ | CH₃ | CH | |
| H | CHClCH₃ | H | OCH₃ | CH₃ | CH | |
| 2-F | CH₂F | H | OCH₃ | CH₃ | CH | |
| 2-CH₃ | CH₂F | H | OCH₃ | CH₃ | CH | |
| 2-OCH₃ | CH₂F | H | OCH₃ | CH₃ | CH | |
| 2-Cl | CH₂F | H | OCH₃ | CH₃ | CH | |
| 2-CH₂CH | CH₂F | H | OCH₃ | CH₃ | CH | |
| H | CH₂F | CH₃ | OCH₃ | CH₃ | CH | |
| H | CH₂CH₂F | H | OCH₃ | CH₃ | CH | |
| H | CH₂CH₂Cl | H | OCH₃ | CH₃ | CH | |
| H | CHFCl | H | OCH₃ | OCH₃ | CH | |

TABLE 25

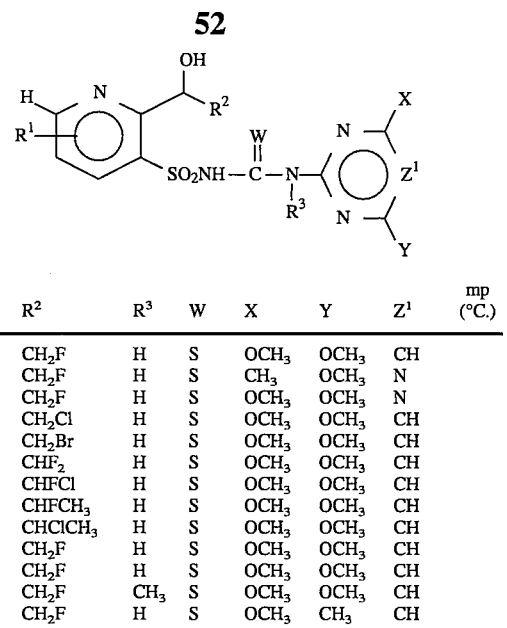

| R¹ | R² | R³ | W | X | Y | Z¹ | mp (°C.) |
|---|---|---|---|---|---|---|---|
| H | CH₂F | H | S | OCH₃ | OCH₃ | CH | |
| H | CH₂F | H | S | CH₃ | OCH₃ | N | |
| H | CH₂F | H | S | OCH₃ | OCH₃ | N | |
| H | CH₂Cl | H | S | OCH₃ | OCH₃ | CH | |
| H | CH₂Br | H | S | OCH₃ | OCH₃ | CH | |
| H | CHF₂ | H | S | OCH₃ | OCH₃ | CH | |
| H | CHFCl | H | S | OCH₃ | OCH₃ | CH | |
| H | CHFCH₃ | H | S | OCH₃ | OCH₃ | CH | |
| H | CHClCH₃ | H | S | OCH₃ | OCH₃ | CH | |
| 5-OCH₃ | CH₂F | H | S | OCH₃ | OCH₃ | CH | |
| 5-Cl | CH₂F | H | S | OCH₃ | OCH₃ | CH | |
| H | CH₂F | CH₃ | S | OCH₃ | OCH₃ | CH | |
| H | CH₂F | H | S | OCH₃ | CH₃ | CH | |

TABLE 26

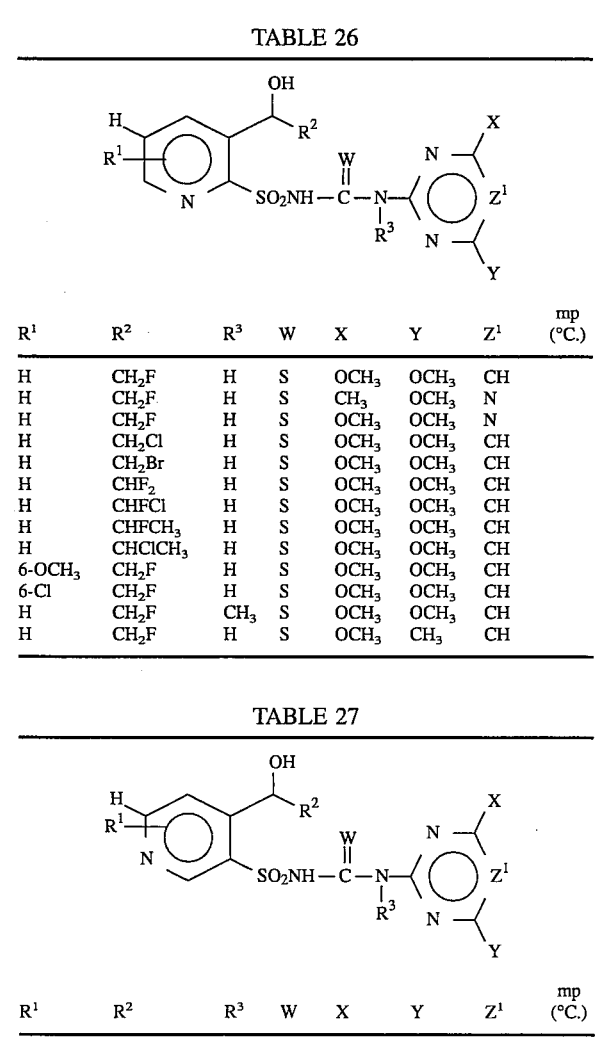

| R¹ | R² | R³ | W | X | Y | Z¹ | mp (°C.) |
|---|---|---|---|---|---|---|---|
| H | CH₂F | H | S | OCH₃ | OCH₃ | CH | |
| H | CH₂F | H | S | CH₃ | OCH₃ | N | |
| H | CH₂F | H | S | OCH₃ | OCH₃ | N | |
| H | CH₂Cl | H | S | OCH₃ | OCH₃ | CH | |
| H | CH₂Br | H | S | OCH₃ | OCH₃ | CH | |
| H | CHF₂ | H | S | OCH₃ | OCH₃ | CH | |
| H | CHFCl | H | S | OCH₃ | OCH₃ | CH | |
| H | CHFCH₃ | H | S | OCH₃ | OCH₃ | CH | |
| H | CHClCH₃ | H | S | OCH₃ | OCH₃ | CH | |
| 6-OCH₃ | CH₂F | H | S | OCH₃ | OCH₃ | CH | |
| 6-Cl | CH₂F | H | S | OCH₃ | OCH₃ | CH | |
| H | CH₂F | CH₃ | S | OCH₃ | OCH₃ | CH | |
| H | CH₂F | H | S | OCH₃ | CH₃ | CH | |

TABLE 27

| R¹ | R² | R³ | W | X | Y | Z¹ | mp (°C.) |
|---|---|---|---|---|---|---|---|
| H | CH₂F | H | S | OCH₃ | OCH₃ | CH | |
| H | CH₂F | H | S | CH₃ | OCH₃ | N | |
| H | CH₂F | H | S | OCH₃ | OCH₃ | N | |
| H | CH₂Cl | H | S | OCH₃ | OCH₃ | CH | |
| H | CH₂Br | H | S | OCH₃ | OCH₃ | CH | |

TABLE 27-continued

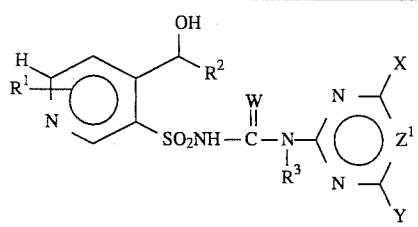

| $R^1$ | $R^2$ | $R^3$ | W | X | Y | $Z^1$ | mp (°C.) |
|---|---|---|---|---|---|---|---|
| H | $CHF_2$ | H | S | $OCH_3$ | $OCH_3$ | CH | |
| H | CHFCl | H | S | $OCH_3$ | $OCH_3$ | CH | |
| H | $CHFCH_3$ | H | S | $OCH_3$ | $OCH_3$ | CH | |
| H | $CHClCH_3$ | H | S | $OCH_3$ | $OCH_3$ | CH | |
| 2-$OCH_3$ | $CH_2F$ | H | S | $OCH_3$ | $OCH_3$ | CH | |
| 2-Cl | $CH_2F$ | H | S | $OCH_3$ | $OCH_3$ | CH | |
| H | $CH_2F$ | $CH_3$ | S | $OCH_3$ | $OCH_3$ | CH | |
| H | $CH_2F$ | H | S | $OCH_3$ | $CH_3$ | CH | |

TABLE 28

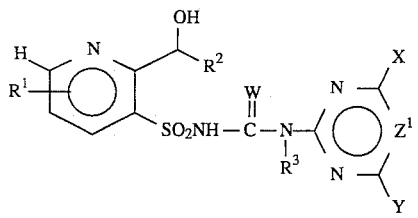

| $R^1$ | $R^2$ | $R^3$ | W | X | Y | $Z^1$ | mp (°C.) |
|---|---|---|---|---|---|---|---|
| H | $CH_2F$ | H | S | $OCH_3$ | $OCH_3$ | CH | |
| H | $CH_2F$ | H | S | $CH_3$ | $OCH_3$ | N | |
| H | $CH_2F$ | H | S | $OCH_3$ | $OCH_3$ | N | |
| H | $CH_2Cl$ | H | S | $OCH_3$ | $OCH_3$ | CH | |
| H | $CH_2Br$ | H | S | $OCH_3$ | $OCH_3$ | CH | |
| H | $CHF_2$ | H | S | $OCH_3$ | $OCH_3$ | CH | |
| H | CHFCl | H | S | $OCH_3$ | $OCH_3$ | CH | |
| H | $CHFCH_3$ | H | S | $OCH_3$ | $OCH_3$ | CH | |
| H | $CHClCH_3$ | H | S | $OCH_3$ | $OCH_3$ | CH | |
| 5-$OCH_3$ | $CH_2F$ | H | S | $OCH_3$ | $OCH_3$ | CH | |
| 5-Cl | $CH_2F$ | H | S | $OCH_3$ | $OCH_3$ | CH | |
| H | $CH_2F$ | $CH_3$ | S | $OCH_3$ | $OCH_3$ | CH | |
| H | $CH_2F$ | H | S | $OCH_3$ | $CH_3$ | CH | |

Test results indicate that the compounds of the present invention are highly active pre-emergent or post-emergent herbicides or plant growth regulants. Many of them have utility for broad-spectrum pre- and/or post-emergency weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat and barley. Alternatively, the subject compounds are useful to modify plant growth.

The rates of application for the compounds of the present invention are determined by a number of factors, including their use as plant growth modifiers or as herbicides, the crop species involved, the types of weeds to be controlled, weather and climate, formulations selected, mode of application, amount of foliage present, etc.

In general terms, the subject compounds should be applied at levels of around 0.05 to 10 kg/ha, the lower rates being suggested for use on lighter soils and/or those having a low organic matter content, for plant growth modifications or for situations where only short-term persistence is required.

Formulations

Useful formulations of the compounds of formula(I) can be prepared in conventional ways. They include dusts, granules, pellets, solutions, suspensions, emulsions, wettable powders, emulsifiable concentrates and the like. Many of these may be applied directly.

Sprayable formulations can be extented in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (1) about 0.1% to 20% surfactant(s) and (2) about 1% to 99.9% solid or liquid inert diluent(s). More specially, they will contain these ingredients in the following approximate proportions:

| Formulations | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or a Diluent equals 100 weight percent.

Lower or higher levels of active ingredient can, of course, be present depending on the intended use and the physical properties of the compound. Higher ratios of surfactants to activate ingredient are sometimes desirable, and are achieved by incorporation into the formation or by tank mixing.

Typical solid diluents are described in Watkins, et al., "Handbook of Insecticide Dust Diluents and Carriers", 2nd Ed., Dorland Books, Caldwell, N.J., but other solids, either mined or monufactured, may be used. The more absorptive diluents are preferred for wettable powders and the denser ones for dusts.

Typical liquid diluents and solvents are described in Marsden, "Solvent Guide", 2nd Ed., Interscience, New York, 1950. Solubility under 0.1% is preferred for suspension concentrates; Solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses.

All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques.

See J. E. Browning, "Agglomeration", Chemical Engineering, Dec. 4, 1967, pp, 147ff. and "Perry's chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41; R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182; H. Gysin and E. Knusli, U.S. Pat. No. 2,891,855, Jun. 23, 1959, Col. 3, line 66 through Col. 5, line 17 and Examples 1–4; G. C. Klingman, "Weed Control as a Science", John Wiley and S. A. Evans, "Weed control Handbook", 5th Ed., Blackwell Scientific Publications, Oxford, 1968, pp. 101–103.

The compounds of the present invention can be used independently and may be used in combination with any other commercial herbicide. A summary of the possible combination herbicides is given below.

+HL,1 Common Name+HZ,1/32 ?

| | | |
|---|---|---|
| acetochlor | acifluorfen | AC 252,214 |
| AC 263,499 | acrolein | alachlor |
| ametryn | amitrole | AMS |
| asulam | assure | atrazine |
| BAS-514 | barban | benefin |
| bensulfuron methyl | bensulide | bentazon |
| benzofluor | benzoylprop | bifenox |
| bromacil | bromoxynil | butachlor |
| buthidazole | butralin | butylate |
| cacodylic acid | CDAA | CDEC |
| CGA 82725 | CH-83 | chloramben |
| chlorbromuron | chlorimuron ethyl | chloroxuron |
| chlorpropham | chlorsulfuron | chlortoluron |
| cinmethylin | clethodim | clomazone |
| cloproxydim | clopyralid | CMA |
| cyanzine | cycloate | cycluron |
| cyperquat | cyprazine | cyprazole |
| cypromid | dalapon | dazomet |
| DCPA | desmediphan | desmetryn |
| diallate | dicamba | dichlorbenil |
| dichlorprop | dichlofop | diethatyl |
| difenzoquat | dinitramine | dinoseb |
| diphenamid | dipropetryn | diquat |
| diuron | DNOC | DOWCO453ME |
| DPX-M6316 | DSMA | endothall |
| EPTC | ethalfluralin | ethoxfumesate |
| Express | fenac | fenoxaprop ethyl |
| fenuron | fenuron TCA | flamprop |
| fluazifop | fluazifop-butyl | fluazifop-P |
| fluchloralin | fluometuron | fluorochloridone |
| fluorodifen | fluoroglycofen | fluridone |
| fomesafen | fosamine | glyphosate |
| haloxyfop | harmoney | hexaflurate |
| hexazinone | HW-52 | imazamethabenz |
| imazapyr | imazaquin | imazethapyr |
| ioxynil | isopropalin | isoproturon |
| isouron | isoxaben | karbutilate |
| lactofen | lenacil | linuron |
| MAA | MAMA | MCPA |
| MCPB | mecoprop | mefluidide |
| methalpropalin | methabenzthiazuron | metham |
| methazole | methoxuron | metolachlor |
| metribuzin | metsulfuron methyl | MH |
| molinate | monolinuron | monuron |
| monuron TCA | MSMA | My-93 |
| napropamide | naproanilide | naptalam |
| neburon | nitralin | nitrofen |
| nitrofluorfen | norea | norfluazon |
| NTN-801 | oryzalin | oxadiazon |

+HL,1 Common Name+HZ,1/32 ?-continued

| | | |
|---|---|---|
| oxyfluorfen | paraquat | pebulate |
| pendimethalin | perfluidone | phenmedipham |
| picloram | PPG-1013 | pretilachlor |
| procyazine | profluralin | prometon |
| prometryn | pronamide | propachlor |
| propanil | propazine | propham |
| prosulfalin | prynachlor | pyrazon |
| pyrazolate | quizalofop ethyl | quizalofop |
| SC-2957 | secbumeton | sethoxydim |
| siduron | simazine | SL-49 |
| sulfometuron methyl | TCA | tebuthiuron |
| terbacil | terbuchlor | terbuthylazine |
| terbutol | terbutryn | thiameturon methyl |
| thiobencarb | triallate | triclopyr |
| tridiphane | trifluralin | trimeturon |
| 2,4-D | 2,4-DB | vernolat |
| X-52 | xylachlor | |

EXAMPLE 1

2-Fluoro-3-fluoroacetyl pyridine

To a stirring solution of 1.5M lithium diisopropylamide mono (tetrahydrofuran) (69 ml) in 50 ml anhydrous tetrahydrofuran cooled to −70° C. under nitrogen atmosphere is added dropwise 2-fluoropyridine (10 g).

To the solution is added dropwise ethyl fluoroacetate (13 g) in 5 ml of anhydrous tetrahydrofuran at −70° C. and stirred for 3 hours at −70° C.

The reaction mixture is then poured into 200 ml of cold water and neutralized with dilute $H_2SO_4$. The mixture is extracted three times with methylene chloride. The methylene chloride portions are combined, dried over magnesium sulfate, filtered and evaporation of the methylene chloride, a residue is obtained. This is chromatographed through silica gel using 1:3 ethyl acetatehexane as eluant.

Evaporation of the solvent mixture yields 12 g of the desired product (Yield: 74%).

$^1$HNMR ($CDCl_3$): δ 5.1(s, 1H), 5.8(s, 1H), 7.4(m, 1H), 8.4(m, 2H).

EXAMPLE 2

2-Fluoro-3-(2-fluoro-1-hydroxyethyl)pyridine

To 12 g of 2-fluoro-3-(fluoroacetyl)pyridine dissolved in 30 ml of methanol is added dropwise 1.44 g of sodium borohydride. After stirring at 0° C. for 30 minutes to the solution is added 40 ml of water.

The resulting solution is extracted three times with methylene chloride and the methylene chloride phase is dried over magnesium sulfate, filtered and evaporated to obtain 12 g of the desired product (colorless oil, Yield: 98%).

EXAMPLE 3

3-(2-Fluoro-1-hydroxyethyl)-2-(phenylmethylthio)pyridine

To a stirring solution of a 60% dispersion of sodium hydride in mineral oil (3.9 g) in 200 ml anhydrous dimethylformamide cooled to −5° C. under nitrogen atmosphere is added 11.6 ml of benzyl mercaptan by using a syringe at a temperature of <0° C.

After stirring at room temperature for one hour a solution of 2-fluoro-3-(2-fluoro-1-hydroxyethyl)pyridine (12 g) in 4 ml of anhydrous dimethylformamide is slowly injected at 5° C. The resulting mixture is warmed slowly to room temperature and stirred for 24 hours.

Water (200 ml) is then added and the mixture is extracted three times with Et$_2$O. The organic phase is washed with cold water and dried with magnesium sulfate.

The solvent is removed under reduced pressure, and the residue is chromatographed on silica gel(n-hexane/EtoAc= 5:1) to afford the desired product (16 g, oil).

$^1$H NMR(CDCl$_3$): δ 3.4(m, 1H), 3.9–4.3(m, 1H), 4.6(s, 2H), 4.7–5.1(m, 1H), 5.2–5.6(m, 1H), 7.0–7.6(m, 6H), 7.9(m, 1H), 8.6(m, 1H).

EXAMPLE 4

3-(1-Acetoxy-2-fluoroethyl)-2-(phenylmethylthio) pyridine

A solution of 3-(2-fluoro-1-hydroxyethyl)-2-(phenylmethylthio)pyridine (16 g) in dry THF and acetic anhydride (7.4 g) is stirred with a catality amount of 4-dimethylaminopyridine at room temperature for 12 hours. The reaction mixture is then poured into water and neutralized with dilute H$_2$SO$_4$. The mixture is extracted three times with methylene chloride, the combined extracts are dried (MgSO$_4$), evaporated to obtain the desired product (oil, 17.2 g, Yield: 93%).

$^1$H NMR(CDCl$_3$): δ 2.2(s, 3H), 4.2(d, 1H), 4.5(s, 2H), 5.0(d, 1H), 6.1, 6.4(m, 1H) 7.0–7.8(m, 7H), 8.4(m, 1H).

EXAMPLE 5

3-(1-Acetoxy-2-fluoroethyl)-2-pyridinesulfonamide

To a stirred solution of 3-(1-acetoxy-2-fluoroethyl)-2-(phenylmethylthio) pyridine (21 g) in 350 ml of methylene chloride and 350 ml of water is added at 0° C. 10.5 ml of conc. HCl.

To the reaction mixture 175 ml of 10% sodium hypochlorite solution is added for 30 minutes keeping the temperature below 1° C.

The mixture is stirred at 0° C. for 20 minutes, poured into 80 ml of cold water and extracted three times with cold methylene chloride. The organic phase is separated, washed with sodium bisulfite and dried with magnesium sulfate keeping the temperature below 0° C. The dried solution is cooled in a dry ice-acetone bath (−70° C.) and then a slow stream of ammonia gas is passed for 10 minutes. The mixture is evaporated until the volume of the solution reaches 100 ml.

To the concentrated solution 50 ml of water is add and the mixture is extracted three times with methylene chloride. The combined organic layer is dried with magnesium sulfate. The solvent is removed under reduced pressure and the residue is chromatographed on silica gel to afford the product (12 g, Yield: 67%).

m.p.: 127°–129° C.

$^1$H NMR(DMSO-d6): δ 2.2(s, 3H), 4.3(m, 1H), 5.2(m, 1H), 6.7, 7.1(m, 1H), 7.2(s, 2H), 7.7(m, 1H), 8.0(m, 1H), 8.6(m, 1H).

EXAMPLE 6

3-(1-Acetoxy -2-fluoroethyl)-N-[(4,6-dimethoxypyrimidin-2-yl)amino carbonyl]-2-pyridinesulfonamide To 4.1 g of 3-(1-acetoxy-2-fluoroethyl)-2-pyridine-sulfonamide in 50 ml of acetonitrile is added 4.22 g of phenyl(4,6-dimethoxypyrimidin-2-yl)carbamate and 2.4 g of 1,8-diazabicyclo[5.4.0]undec-7-ene (DBU). After stirring at room temperature for 2 hours the solution is acidified to pH 4.5 with 5% hydrochloric acid. The resultant solution is extracted with methylene chloride and the methylene chloride phase is dried over magnesium sulfate, filtered and evaporated. Trituration of the residue with Et$_2$O yields 6 g of the product (solid, Yield: 89%), which is washed with a mixture solvent of ethylacetate/n-hexane(1/1).

m.p.: 145°–147° C.

$^1$H NMR (CDCl$_3$): δ 2.2(s, 3H), 4.0(s, 6H), 4.5 (m, 1H), 5.3(m, 1H), 5.8(s, 1H), 6.8–7.2(m, 1H), 7.6(m, 1H), 8.3(m, 1H), 8.7(m, 1H), 13.0(ls, 1H).

EXAMPLE 7

N-[(4,6-Dimethoxypyrimidin-2-yl)aminocarbonyl]-3-(2-fluoro-1 -hydroxyethyl)-2-pyridinesulfonamide To 4 g of 3-(1-acetoxy-2-fluoroethyl)-N-[(4,6-dimethoxypyrimidin-2-yl)aminocarbonyl] -2-pyridinesulfonamide in 100 ml of methanol is added 0.46 g of lithium hydroxide monohydrate and 1 ml of water.

After stirring at room temperature for 3 hours the solution is acidified to pH 4.5 with 5% hydrochloric acid. The resultant solution is extracted three times with methylene chloride. The organic phase is washed three times with water, dried over magnesium sulfate, filtered and evaporated to yield 3.3 g of the subject compound (Yield:90%).

m.p.: 119°–120° C.

$^1$H NMR(Acetone-d$_6$): δ 3.97(s, 6H), 4.38–4.91(m, 2H), 5.36(s, 1H), 5.91(s, 1H), 6.03(m, 1H), 7.74(m, 1H), 8.43(m, 1H), 8.57(m, 1H), 9.55(s, 1H), 13.02(s, 1H)

EXAMPLE 8

2-(1-Acetoxy-2-fluoroethyl)-3-pyridinesulfonamide 5.3 g of 2-(1-acetoxy-2-fluoroethyl)-N-t-butyl-3-pyridinesulfonamide is added to 20 ml of trifluoroacetic acid and allowed to stir at room temperature for 12 hours. The acid is evaporated and the residual oil is taken up in CH$_2$Cl$_2$. The solution is washed with sat. aq. NaHCO$_3$, dried (MgSO$_4$), evaporated and the crude solid product is crystallized from ethyl acetate and n-haxane; 3.1 g (Yield: 71%).

m.p.: 141°–143° C.

$^1$HNMR(CDCl$_3$+ DMSO-d$_6$): δ 2.13(s, 3H), 4.83(m, 2H), 6.63–7.06(m, 1H), 7.20(s, 2H), 7.42–7.63(m, 1H), 8.32–8.86(m, 2H), IR(KBr) 1717 cm$^{-1}$ (C=O)

EXAMPLE 9

2-(1-Acetoxy-2-fluoroethyl)-N-[(4,6-dimethoxypyrimidin-2 -yl)aminocarbonyl]-3-pyridinesulfonamide To a solution of 2-(1-acetoxy-2-fluoroethyl)-3-pyridine-sulfonamide (2.10 g) and phenyl(4,6-dimethoxypyrimidin-2-yl)carbamate (1.49 g) in 50 ml acetonitrile is added dropwise 0.7 ml of 1,8-diazabicyclo[5.4.0]undec-7-ene-(DBU) at 15° C. After stirring for 2 hours the resultant solution is extracted with methylene chloride and 5% hydrochloric acid. The organic phase is dried over magnesium sulfate, filtered and evaporated to yield the subject compound.

m.p.: 188°–190° C.

$^1$HNMR(CDCl$_3$): δ 2.03(s, 3H), 4.00(s, 6H), 4.84(dd, J$_1$=46.0Hz, J$_2$=6.0Hz, 2H), 5.84(s, 1H), 6.50–6.90(m, 1H), 7.33–7.68(m, 2H), 8.60–8.93(m, 2H), 13.33(s, 1H) IR(KBr): 1737, 1702 cm$^{-1}$ (C=O)

EXAMPLE 10

2-(2-Fluoro-1-hydroxyethyl)-N-[(4,6-dimethoxy-pyrimidin-2
-yl)aminocarbonyl]-3-pyridinesulfonamide To 0.88 g of 2-(1-acetoxy-2-fluoroethyl)-N-[(4,6-dimethoxypyrimidin-2 -yl)aminocarbonyl]-3-pyridine-sulfonamide in 20 ml of methanol is added 0.25 g of lithium hydroxide monohydrate. The mixture is heated to reflux for 1 hour, then allowed to cool and the methanol is evaporated.

The residue is taken up in 15 ml of CH$_2$Cl$_2$ and 10 ml of water, and acidified to pH 2–3 with 1N HClaq. The organic phase is dried over magnesium sulfate, filtered and evaporated to yield 0.42 g of the subject compound.

m.p.: 162°–164° C.

$^1$HNMR(CDCl$_3$+DMSO-d$_6$): δ 4.02(s, 6H), 4.78(dd, J$_1$ = 46.0Hz, J$_2$= 5.0Hz, 2H), 5.88(s, 1H), 7.53–7.73(m, 1H), 8.53–8.98(m, 2H). IR(KBr): 1704 cm$^{-1}$ (C=O)

EXAMPLE 11

3-(Chloroacetyl)-N-(1,1-dimethylethyl)-2-pyridine-sulfonamide

Under a nitrogen atmosphere, to a stirred solution of N-(1,1-dimethylethyl)- 2-pyridinesulfonamide(4.0 g, 18.7 mmole) in 50 ml of anhydrous THF is slowly injected at −70° C. 17 ml of 2.5M n-BuLi.

The mixture is stirred for 3 hours at −40° C., cooled to −70° C. and then 3 g of ethyl chloroacetate is injected dropwise.

The reaction mixture is stirred at −40° C. for 1 hour, poured into cold water and extracted three times with CH$_2$Cl$_2$. The organic phase is dried over magnesium sulfate, filtered and evaporated.

The residue is purified by chromatography to give the pure product (3.68 g, Yield: 68%).

NMR(CDCl$_3$): δ 1.2(s, 9H), 4.67(s, 2H), 5.3(s, 1H), 7.8(m, 2H), 9.0(m, 1H)

EXAMPLE 12

3-(2-Chloro-1-hydroxyethyl)-N-(1,1-dimethylethyl)-2
-pyrimidinesulfonamide

To a stirred solution of 3-(chloroacetyl)-N-(1,1-dimethylethyl)-2-pyridinesulfonamide (3.68 g, 12.7 mmole) in 100 ml of methanol is added at 0° C. NaBH$_4$ (0.24 g, 6.35 mmole). The reaction mixture is stirred at 0° C. for 1 hour, added 10 ml of water and extracted three times with CH$_2$Cl$_2$.

The organic phase is dried over magnesium sulfate, filtered and evaporated to yield 3.56 g of the subject compound (Yield: 96%).

EXAMPLE 13

3-(1-Acetoxy-2-chloroethyl)-N-(1,1-dimethylethyl)-2-pyrimidinesulfonamide

To a stirred solution of 3-(2-chloro-1-hydroxyethyl)-N-(1,1-dimethylethyl)- 2-pyridinesulfonamide in dry THF is added 1.6 g of Ac$_2$O and a catality amount of 4-dimethy-laminopyridine. The mixture is stirred at room temperature for 12 hours, water is added, neutralized with dilute H$_2$SO$_4$ and extracted three times with CH$_2$Cl$_2$. The organic phase is evaporated to give the subject compound (3.6 g, Yield: 88%).

NMR(CDCl$_3$): δ 1.2(s, 9H), 2.2(s, 3H), 4.0(m, 2H), 5.7(s, 1H), 7.0(m, 1H), 7.7(m, 1H), 8.1(m, 1H), 8.7(m, 1H).

EXAMPLE 14

3-(1-Acetoxy-2-chloroethyl)-2-pyridinesulfonamide 3.6 g of 3-(1-acetoxy-2-chloroethyl)-N-(1,1-dimethylethyl)-2-pyridinesulfonamide is added to 20 ml of trifluoroacetic acid and allowed to stir at 40° C. for 12 hours. The acid is evaporated and the crude product is purified by column chromatography to give the subject compound (3 g).

m.p.: 146°–147° C.

NMR(CDCl$_3$): δ 2.1(s, 3H), 4.0(m, 2H), 6.0(s, 2H), 6.9(m, 1H), 7.7(m, 1H), 8.1(m, 1H), 8.7(m, 1H)

EXAMPLE 15

3-(1-Acetoxy-2-chloroethyl)-N-[(4,6-dimethoxy-pyrimidin-2
-yl)aminocarbonyl]-2-pyridinesulfonamide To a stirred solution of 3-(1-acetoxy-2-chloroethyl)-2-pyridinesulfonamide (200 mg) and phenyl(4,6-dimethoxy-pyrimidin-2-yl)carbamate (197 mg) in 20 ml of acetonitrile is added dropwise 109 mg of DBU.

After stirring at room temperature for 2 hours the solution is acidified to pH 4.5 with 5% aq. HCl. The resultant solution is extracted three times with methylene chloride and the methylene chloride phase is dried over MgSO$_4$, filtered and evaporated.

Trituration of the residue with Et$_2$O (10 ml) yield 280 mg of the solid product.

m.p.: 159°–161° C.

EXAMPLE 16

3-(2-Chloro-1-hydroxyethyl)-N-[(4,6-dimethoxypyrimidin-2-yl)aminocarbonyl]-2-pyridine sulfonamide To 140 mg of 3-(1-acetoxy-2-chloroethyl)-N-[(4,6-dimethoxypyrimidin-2-yl)aminocarbonyl] -2-pyridine-sulfonamide in 20 ml of methanol is added 20 mg of LiOH.H$_2$O and 0.5 ml of water. After stirring at room temperature for 3 hours the solution is acidified to pH 4.5 with 5% aq. HCl. The resultant solution is extracted three times with CH$_2$Cl$_2$. The organic phase is evaporated and the trituration of the residue with Et$_2$O yields the solid product.

m.p.: 135°–137° C.

In the following example, all parts are by weight unless otherwise indicated.

EXAMPLE 17

| Wettable Powder | |
|---|---|
| N-[(4,6-dimethoxy pyrimidin-2-yl)amino carbonyl]-3-(2-fluoro-1-hydroxyethyl)-2-pyridinesulfonamide | 80% |

-continued

| Wettable Powder | |
|---|---|
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 18

| Wettable Powder | |
|---|---|
| 3-(2-fluoro-1-hydroxyethyl)-N-[(4-methoxy-6-methyl-pyrimidin-2-yl) amino carbonyl]-2-pyridine sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 19

| Granule 2 | |
|---|---|
| wettable powder of Example 18 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender.

The granules are dried and packaged.

EXAMPLE 20

| Extruded Pellet | |
|---|---|
| N-[(4,6-dimethoxypyrimidin-2-yl)amino carbonyl]-3-(2-fluoro-1-hydroxyethyl)-2-pyridinesulfonamide | 25% |
| anhydrous sodium sulfate | 10% |
| crude calcium lignisulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. They may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 21

| Oil Suspension | |
|---|---|
| N-[(4,6-dimethoxy pyrimidin-2-yl)amino carbonyl]-3-(2-fluoro-1-hydroxyethyl)-2-pyridinesulfonamide | 25% |
| polyoxyethylene sorbitol hexaoleate | 5% |
| highly aliphatic hydrocarbon oil | 70% |

The ingredients are ground together in sand mill until the solid particles have been reduced to under about 5 microns. The resulting thick suspension may be applied directly, but preferably after being extended with oils or emulsified in water.

EXAMPLE 22

| Wetting Powder | |
|---|---|
| N-[(4,6-dimethoxypyrimidin-2-yl)aminocarbonyl]-3-(2-fluoro-1-hydroxyethyl)-2-pyridinesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm openings) and packaged.

EXAMPLE 23

| Low Strength Granule | |
|---|---|
| N-[(4,6-dimethoxypyrimidin-2-yl)aminocarbonyl]-3-(2-fluoro-1-hydroxyethyl)-2-pyridinesulfonamide | 1% |
| N,N-dimethylformamide | 9% |
| attapulgite granule (U.S.S. 20–40 sieve) | 90% |

The active ingredient is dissolved in the solvent and the solution is sprayed upon dedusted granules in a double cone blender.

After spraying of the solution has been completed, the blender is allowed to run for a short period and then the granules are packaged.

EXAMPLE 24

| Aqueous Suspension | |
|---|---|
| N-[(4,6-dimethoxy pyrimidin-2-yl)aminocarbonyl]-3-(2-fluoro-1-hydroxyethyl)-2-pyridinesulfonamide | 40% |
| polyacrylic acid thickener | 0.3% |
| dodecylphenol polyethylen glycol ether | 0.5% |
| disodium phosphate | 1% |
| monosodium phosphate | 0.5% |
| polyvinyl alcohol | 1% |
| water | 56.7% |

The ingredients are blended and ground together in a sand mill to produce particles essentially all under 5 microns in size.

EXAMPLE 25

| Solution | |
|---|---|
| N-[(4,6-dimethoxy pyrimidin-2-yl)aminocarbonyl]-3-(2-fluoro-1-hydroxyethyl)-2-pyridinesulfonamide, ammonium salt | 5% |
| water | 95% |

The salt is added directly to the water with stirring to produce the solution, which may then be packaged for use.

EXAMPLE 26

| Low Strength Granule | |
|---|---|
| N-[(4,6-dimethoxy pyrimidin-2-yl)aminocarbonyl]-3-(2-fluoro-1-hydroxyethyl)-2-pyridinesulfonamide | 0.1% |
| attapulgite granules (U.S.S. No. 20–140 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and packaged.

EXAMPLE 27

| Wettable Powder | |
|---|---|
| N-[(4,6-dimethoxy pyrimidin-2-yl)aminocarbonyl]-3-(2-fluoro-1-hydroxyethyl)-2-pyridinesulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredient are thoroughly blended, passed through an air mill, to produce an average particle size under 15 microns, reblended, and sifted through a U.S.S. No. 50 sieve (0.3 mm opening) before packaging. All compounds of the invention may be formulated in the same manner.

EXAMPLE 28

| Granule | |
|---|---|
| wettable powder of Example 18 | 15% |
| gypsum | 69% |
| potassium sulfate | 16% |

The ingredients are blended in rotating mixer and water sprayed on to accomplish granulation. When most of the material has reached the desired range of 1.0 to 0.42 cm (U.S.S. #18 to 40 sieves), the granules are removed, dried, and screened. Oversized material is crushed additional material in the desired range. These granules contain % active ingredient.

EXAMPLE 29

| High Strength Concentrate | |
|---|---|
| N-[(4,6-dimethoxy pyrimidin-2-yl)aminocarbonyl]-3-(2-fluoro-1-hydroxyethyl)-2-pyridinesulfonamide | 99% |
| silica aerogel | 0.5% |
| synthetic amorphous silica | 0.5% |

The ingredient are blended and ground in a hammer-mill to produce a material essentially all passing a U.S.S. No. 50 screen (0.3 mm opening). The concentrate may be formulated further if necessary.

EXAMPLE 30

| Wettable Powder | |
|---|---|
| 3-(2-fluoro-1-hydroxyethyl)-N-[(4-methoxy-6-methyl-pyrimidin-2-yl) aminocarbonyl]-2-pyridinesulfonamide | 90% |
| dioctyl sodium sulfosuccinate | 0.1% |
| synthetic fine silica | 9.9% |

The ingredient are blended and ground in a hammer-mill to produce particles essentially all below 100 microns. The material is sifted through a U.S.S. No. 50 screen and the packaged.

EXAMPLE 31

| Wettable Powder | |
|---|---|
| N-[(4,6-dimethoxy pyrimidin-2-yl)aminocarbonyl)-3-(2-fluoro-1-hydroxyethyl)-2-pyridinesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and the packaged.

EXAMPLE 32

| Oil Suspension | |
|---|---|
| N-[(4,6-dimethoxy pyrimidin-2-yl)aminocarbonyl)-3-(2-fluoro-1-hydroxyethyl)-2-pyridinesulfonamide | 35% |
| blended of polyalcohol carboxylic estes and oil soluble petroleum | 6% |
| xylene | 59% |

The ingredients are combined and ground together in a sand mill to produce particle essentially all below 5 microns. The product can be used directly, extended with oil, or emulsified in water.

EXAMPLE 33

| Dust | |
|---|---|
| N-[(4,6-dimethoxy pyrimidin-2-yl),aminocarbonyl]-3-(2-fluoro-1-hydroxyethyl)-2-pyridinesulfonamide | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 34

| Emulsifiable Concentrate | |
|---|---|
| N-[(4,6-dimethoxypyrimidin-2-yl)aminocarbonyl]-3-(2-fluoro-1-hydroxyethyl)-2-pyridinesulfonamide | 10% |
| chlorobenzene | 84% |
| sorbitan monostearate and polyoxyethylene condensates thereof | 6% |

The ingredients are combined and stirred to produce a solution which can be emulsified in water for application.

EXAMPLE 35

Pre-emergence test

To produce a suitable preparation of active compound, 1 part by weight of active compound is mixed with 5 parts by weight of acetone, 1 part by weight of alkylaryl polyglycol ether of emulsifier is added and the concentrate is diluted with water to the desired concentration.

Seeds of the test plants are shown in normal soil and, after 24 hours, watered with the preparation of the active compound.

It is expedient to keep constant the amount of water per unit area. The concentration of the active compound in the preparation is of no importance, only the amount of active compound applied per unit area being desicive. After three weeks, the degree of damage to the plants is rated in % damage in comparison to the development of the untreated control.

The figures denote:

0%= no action (like untreated control)

20%= slight effect

70%= herbicidal effect

100%= total destruction.

In this test, the active compounds(I) according to the preparation Examples exhibit a better herbicidal activity against nomo- and dicotyledon weeds.

EXAMPLE 36

Post-emergence test

To produce a suitable preparation of active compound, 1 part by weight of active compound is mixed with 5 pans by weight of acetone, 1 part by weight of alkylaryl polyglycol ether of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparasion to the development of the untreated control.

The figures denote:

0%= no action (like untreated control)

20%= slight effect

70%= herbicidal effect

100%= total destruction.

In this test, the active compounds(I) according to the preparation Examples exhibit a better herbicidal activity against mono- and dicotyledon weeds.

It is understood that the specification and examples are illustrative but not limitative of the present invention and that other embodiments within the spirit and scope of the invention will suggest themselves to those skilled in the art.

The herbicidal proficiency of the active ingredients of the present invention is evident from the test results which are recorded in following Table 29.

The following Table 29 below is represented pre- and post-emergence herbicidal evaluation [PRIMARY SCREENING (Herbicide)] of following "test compounds".

| Structure | X | Y | Compound No. |
|---|---|---|---|
| (pyridine with OH, F, SO$_2$NHCONH-pyrimidine-X,Y substituents) | OCH$_3$ | OCH$_3$ | 1 |
| | OCH$_3$ | CH$_3$ | 2 |
| | CH$_3$ | CH$_3$ | 3 |
| | Cl | OCH$_3$ | 4 |
| | Cl | OEt | 5 |

-continued

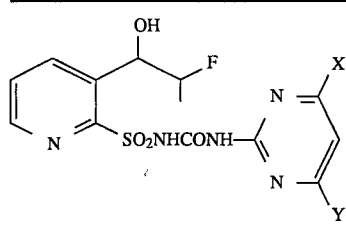
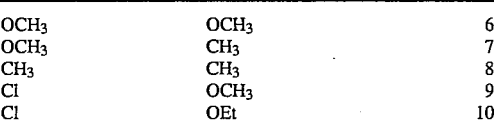

| | X | Y | |
|---|---|---|---|
| | OCH₃ | OCH₃ | 6 |
| | OCH₃ | CH₃ | 7 |
| | CH₃ | CH₃ | 8 |
| | Cl | OCH₃ | 9 |
| | Cl | OEt | 10 |

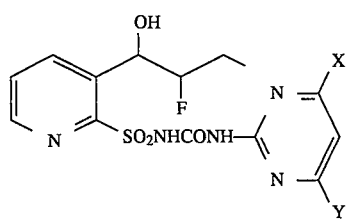
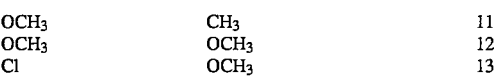

| | X | Y | |
|---|---|---|---|
| | OCH₃ | CH₃ | 11 |
| | OCH₃ | OCH₃ | 12 |
| | Cl | OCH₃ | 13 |

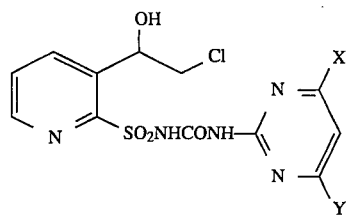
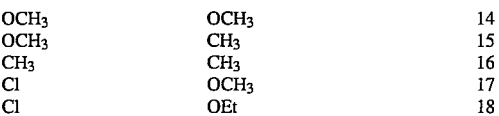

| | X | Y | |
|---|---|---|---|
| | OCH₃ | OCH₃ | 14 |
| | OCH₃ | CH₃ | 15 |
| | CH₃ | CH₃ | 16 |
| | Cl | OCH₃ | 17 |
| | Cl | OEt | 18 |

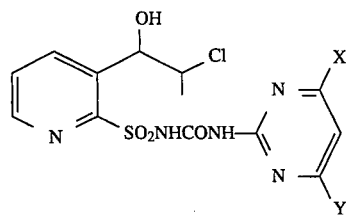
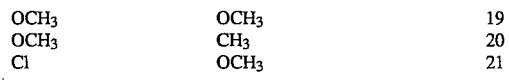

| | X | Y | |
|---|---|---|---|
| | OCH₃ | OCH₃ | 19 |
| | OCH₃ | CH₃ | 20 |
| | Cl | OCH₃ | 21 |

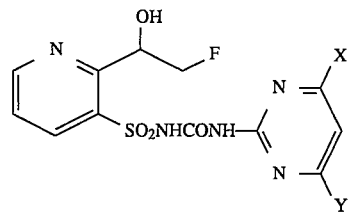
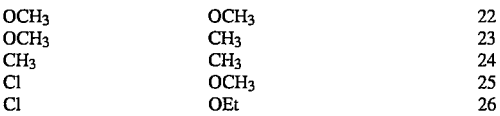

| | X | Y | |
|---|---|---|---|
| | OCH₃ | OCH₃ | 22 |
| | OCH₃ | CH₃ | 23 |
| | CH₃ | CH₃ | 24 |
| | Cl | OCH₃ | 25 |
| | Cl | OEt | 26 |

PLANT RESPONSE SCREENING (Herbicide)

| Compound no. | TYPE | kg/ha | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|
| 1 | PRE | .05 | 100 | 100 | 100 | 100 | 100 | 50 | 90 | 100 | 100 | 100 |
|   | POST | .05 | 100 | 100 | 100 | 100 | 100 | 50 | 100 | 100 | 100 | 100 |
| 2 | PRE | .05 | 100 | 100 | (100) | 100 | 100 |  | 30 | 80 | 90 | 100 |
|   | POST | .05 | 100 | 100 | (100) | 100 | 100 | 20 | 100 | 90 | 100 | 100 |
| 3 | PRE | .05 | 90 | 60 | [0] | 50 | 100 | 0 | 0 | 0 | 0 | 85 |
|   | POST | .05 | 90 | 100 | [70] | 90 | 100 | 60 | 25 | 20 | 50 | 70 |
| 4 | PRE | .05 | 100 | 100 | [90] | 100 | 100 | 100 | 80 | 90 | 90 | 100 |
|   | POST | .05 | 100 | 100 | [100] | 100 | 100 | 70 | 100 | 90 | 100 | 100 |
| 5 | PRE | .05 | 100 | 100 | [50] | 100 | 100 | 65 | 30 | 90 | 85 | 100 |
|   | POST | .05 | 100 | 100 | [60] | 100 | 100 | 60 | 90 | 85 | 100 | 100 |
| 6 | PRE | 4 | 100 | 100 | [100] | 100 | 100 | 100 | 100 | 90 | 100 | 100 |
|   | POST | 4 | 100 | 100 | [100] | 100 | 100 | 100 | 100 | 100 | 100 | 100 |
| 7 | PRE | 4 | 100 | 100 | [90] | 100 | 100 | 100 | 90 | 100 | 90 | 100 |
|   | POST | 4 | 100 | 100 | [100] | 100 | 100 | 100 | 100 | 100 | 100 | 100 |
| 8 | PRE | 4 | 100 | 100 | [90] | 100 | 100 | 100 | 100 | 90 | 90 | 100 |
|   | POST | 4 | 100 | 100 | [100] | 100 | 100 | 100 | 100 | 100 | 100 | 100 |
| 9 | PRE | 4 | 100 | 100 | [100] | 100 | 100 | 100 | 100 | 90 | 90 | 100 |
|   | POST | 4 | 100 | 100 | [100] | 100 | 100 | 100 | 100 | 100 | 100 | 100 |
| 10 | PRE | 4 | 100 | 100 | [90] | 100 | 100 | 100 | 90 | 90 | 90 | 100 |

-continued

|    |      |     |     |     |       |     |     |     |     |     |     |     |
|----|------|-----|-----|-----|-------|-----|-----|-----|-----|-----|-----|-----|
|    | POST | 4   | 100 | 100 | [100] | 100 | 100 | 100 | 100 | 90  | 100 | 100 |
| 11 | PRE  | .05 | 100 | 90  | [70]  | 95  | 90  | 30  | 40  | 75  | 90  | 100 |
|    | POST | .05 | 60  | 100 | [50]  | 60  | 80  | 0   | 90  | 65  | 90  | 85  |
| 12 | PRE  | .05 | 100 | 100 | [90]  | 95  | 100 | 80  | 65  | 80  | 85  | 100 |
|    | POST | .05 | 100 | 100 | [80]  | 100 | 100 | 40  | 100 | 80  | 100 | 60  |
| 13 | PRE  | .05 | 90  | 70  | [20]  | 50  | 90  | 90  | 0   | 25  | 60  | 60  |
|    | POST | .05 | 70  | 65  | [15]  | 0   | 60  | 30  | 20  | 0   | 70  | 60  |
| 14 | PRE  | 4   | 100 | 100 | [90]  | 100 | 100 | 100 | 100 | 90  | 100 | 100 |
|    | POST | 4   | 100 | 100 | [100] | 100 | 100 | 100 | 100 | 100 | 100 | 100 |
| 15 | PRE  | 4   | 100 | 100 | [90]  | 100 | 100 | 100 | 100 | 90  | 90  | 100 |
|    | POST | 4   | 100 | 100 | [100] | 100 | 100 | 100 | 100 | 100 | 100 | 100 |
| 16 | PRE  | 4   | 100 | 90  | [90]  | 100 | 100 | 100 | 70  | 90  | 90  | 100 |
|    | POST | 4   | 100 | 100 | [80]  | 100 | 100 | 100 | 100 | 90  | 100 | 100 |
| 17 | PRE  | 4   | 100 | 100 | [90]  | 100 | 100 | 100 | 90  | 90  | 90  | 100 |
|    | POST | 4   | 100 | 100 | [90]  | 100 | 100 | 100 | 100 | 100 | 100 | 100 |
| 18 | PRE  | 4   | 90  | 90  | [70]  | 100 | 100 | 100 | 85  | 90  | 90  | 100 |
|    | POST | 4   | 100 | 100 | [70]  | 100 | 100 | 100 | 90  | 80  | 90  | 100 |
| 19 | PRE  | .05 | 100 | 100 | [90]  | 100 | 100 | 70  | 30  | 80  | 90  | 95  |
|    | POST | .05 | 100 | 100 | [70]  | 65  | 100 | 30  | 100 | 70  | 100 | 70  |
| 20 | PRE  | .05 | 100 | 90  | [80]  | 100 | 90  | 60  | 20  | 60  | 90  | 100 |
|    | POST | .05 | 90  | 100 | [65]  | 60  | 90  | 10  | 65  | 30  | 80  | 70  |
| 21 | PRE  | .05 | 100 | 80  | [60]  | 65  | 50  | 30  | 0   | 0   | 45  | 70  |
|    | POST | .05 | 100 | 80  | [0]   | 0   | 65  | 20  | 0   | 0   | 35  | 20  |
| 22 | PRE  | .05 | 100 | 100 | [50]  | 100 | 100 | 60  | 50  | 85  | 90  | 100 |
|    | POST | .05 | 100 | 100 | [40]  | 100 | 100 | 60  | 100 | 90  | 90  | 90  |
| 23 | PRE  | .05 | 90  | 90  | [40]  | 100 | 100 | 60  | 50  | 90  | 90  | 100 |
|    | POST | .05 | 90  | 65  | [55]  | 60  | 60  | 30  | 80  | 85  | 90  | 85  |
| 24 | PRE  | .05 | 0   | 0   | [0]   | 15  | 50  | 0   | 0   | 10  | 0   | 0   |
|    | POST | .05 | 0   | 0   | [0]   | 0   | 0   | 0   | 0   | 0   | 0   | 0   |
| 25 | PRE  | .05 | 0   | 0   | [0]   | 0   | 0   | 0   | 0   | 0   | 0   | 65  |
|    | POST | .05 | 0   | 0   | [0]   | 0   | 0   | 0   | 0   | 0   | 0   | 10  |
| 26 | PRE  | .05 | 20  | 10  | [0]   | 0   | 0   | 0   | 0   | 0   | 0   | 0   |
|    | POST | .05 | 0   | 0   | [0]   | 0   | 0   | 0   | 0   | 0   | 0   | 0   |

PRIMARY SCREENING (Herbicide)

| Compound No. | TYPE | kg/ha | ZEAMX | GLXMX | GOSHI | TRZAW | ORYSA | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|---|---|---|---|---|
| 1 | PRE | .1 | 100 | 100 | 100 | 100 | 100 | 100 | 100 | (100) | 100 | 100 | 70 | 70 | 100 | 100 | 100 |
|   |   | .05 | 100 | 100 | 100 | 100 | 100 | 100 | 100 | (100) | 100 | 100 | 40 | 60 | 100 | 100 | 100 |
|   |   | .025 | 70 | 100 | 100 | 100 | 100 | 100 | 100 | (100) | 100 | 100 | 0 | 40 | 90 | 100 | 100 |
|   |   | .0125 | 60 | 70 | 70 | 100 | 100 | 100 | 90 | (100) | 100 | 100 | 0 | 30 | 80 | 70 | 100 |
|   |   | .00625 | 40 | 70 | 40 | 65 | 100 | 100 | 100 | (90) | 100 | 100 | 0 | 0 | 90 | 70 | 100 |
|   |   | .025 | 80 | 100 | 70 | 100 | 100 | 100 | 100 | (85) | 100 | 100 | 50 | 65 | 80 | 100 | 100 |
|   |   | .0125 | 70 | 90 | 70 | 90 | 100 | 100 | 90 | (80) | 100 | 100 | 40 | 40 | 70 | 90 | 100 |
|   |   | .00625 | 40 | 80 | 50 | 80 | 100 | 100 | 85 | (70) | 100 | 100 | 40 | 30 | 70 | 100 | 100 |
|   |   | .003125 | 0 | 65 | 50 | 75 | 100 | 90 | 80 | (70) | 100 | 100 | 30 | 20 | 50 | 100 | 100 |
|   |   | .00151 | 0 | 50 | 40 | 40 | 70 | 80 | 70 | (70) | 100 | 100 | 30 | 0 | 100 | 100 | 100 |
| 1 | POST | .1 | 100 | 100 | 100 | 100 | 100 | 100 | 100 | (100) | 100 | 100 |   | 100 | 100 | 100 | 60 |
|   |   | .05 | 100 | 100 | 90 | 100 | 100 | 100 | 100 | (100) | 100 | 100 | 40 | 100 | 100 | 100 | 100 |
|   |   | .025 | 70 | 100 | 70 | 80 | 100 | 100 | 100 | (100) | 100 | 100 | 40 | 100 | 100 | 100 | 100 |
|   |   | .0125 | 70 | 100 | 60 | 70 | 100 | 100 | 100 | (100) | 100 | 100 | 20 | 90 | 80 | 70 | 90 |
|   |   | .00625 | 30 | 100 | 20 | 80 | 100 | 100 | 100 | (100) | 100 | 100 | 0 | 60 | 100 | 100 | 80 |
|   |   | .025 | 80 | 100 | 60 | 90 | 90 | 100 | 80 | (100) | 100 | 90 | 40 | 100 | 100 | 100 | 100 |
|   |   | .0125 | 70 | 100 | 50 | 90 | 95 | 100 | 95 | (100) | 90 | 80 | 20 | 100 | 100 | 95 | 65 |
|   |   | .00625 | 60 | 30 | 30 | 65 | 90 | 90 | 75 | (100) | 100 | 80 | 0 | 50 | 60 | 65 | 65 |
|   |   | .003125 | 0 | 70 | 0 | 0 | 60 | 90 | 50 | (80) | 95 | 100 | 40 | 60 | 70 | 90 | 100 |
|   |   | .00151 | 0 | 90 | 50 | 50 | 70 | 100 | 100 | (90) | 80 | 100 | 20 | 20 | 40 | 90 | 100 |
| 2 | PRE | .1 | 80 | 90 | 40 | 100 | 100 | 100 | 100 | (80) | 100 | 100 | 0 | 0 | 20 | 40 | 100 |
|   |   | .025 | 50 | 60 | 0 | 90 | 90 | 80 | 95 | (70) | 100 | 100 | 0 | 0 | 0 | 0 | 100 |
|   |   | .006 | 0 | 20 | 0 | 50 | 30 | 20 | 50 | (30) | 80 | 90 | 0 | 0 | 20 | 0 | 20 |
|   |   | .0015 | 0 | 0 | 0 | 60 | 70 | 100 | 100 | (100) | 100 | 90 | 70 | 80 | 100 | 100 | 0 |
| 2 | POST | .1 | 65 | 100 | 50 | 40 | 80 | 60 | 90 | (90) | 100 | 90 | 30 | 60 | 60 | 100 | 100 |
|   |   | .025 | 60 | 100 | 10 | 40 | 80 | 50 | 60 | (90) | 80 | 90 | 10 | 40 | 60 | 90 | 100 |
|   |   | .006 | 30 | 100 | 0 | 40 | 60 | 40 | 0 | (90) | 70 | 30 | 80 | 20 | 40 | 60 | 90 |
|   |   | .0015 | 0 | 60 | 0 | 0 | 0 | 0 | 0 | (0) | 0 | 100 | 60 | 65 | 100 | 100 | 60 |
| 4 | PRE | .1 | 80 | 100 | 100 | 100 | 100 | 100 | 100 | (100) | 100 | 100 | 0 | 0 | 65 | 100 | 100 |
|   |   | .025 | 70 | 70 | 80 | 65 | 100 | 60 | 70 | (70) | 100 | 100 | 20 | 10 | 20 | 70 | 65 |
|   |   | .006 | 30 | 30 | 50 | 20 | 70 | 20 | 40 | (40) | 40 | 70 | 0 | 0 | 0 | 40 | 20 |
|   |   | .00156 | 0 | 0 | 0 | 0 | 10 | 0 | 30 | (0) | 0 | 0 | 0 | 0 | 0 | 0 | 0 |
|   |   | .00039 | 0 | 0 | 0 | 0 | 0 | 0 | 0 | (0) | 0 | 0 | 0 | 0 | 0 | 0 | 0 |
| 4 | POST | .1 | 100 | 100 | 100 | 100 | 100 | 100 | 100 | [100] | 100 | 100 | 60 | 70 | 90 | 100 | 100 |
|   |   | .025 | 50 | 30 | 20 | 50 | 100 | 100 | 100 | [70] | 100 | 100 | 60 | 60 | 70 | 100 | 80 |
|   |   | .006 | 0 | 0 | 0 | 0 | 100 | 70 | 80 | [60] | 100 | 100 | 30 | 20 | 40 | 50 | 40 |
|   |   | .00156 | 0 | 0 | 0 | 0 | 70 | 70 | 50 | [20] | 70 | 65 | 0 | 0 | 0 | 30 | 0 |
|   |   | .00039 | 0 | 0 | 0 | 0 | 0 | 30 | 0 | [0] | 0 | 0 | 0 | 30 | 0 | 0 | 0 |
| 5 | PRE | .1 | 100 | 100 | 90 | 100 | 100 | 100 | 100 | [100] | 100 | 100 | 60 | 70 | 70 | 100 | 100 |
|   |   | .025 | 20 | 30 | 20 | 65 | 100 | 100 | 100 | [50] | 100 | 100 | 20 | 0 | 20 | 50 | 50 |
|   |   | .006 | 0 | 0 | 0 | 20 | 70 | 100 | 90 | [0] | 100 | 90 | 0 | 0 | 0 | 30 | 30 |
|   |   | .00156 | 0 | 0 | 0 | 0 | 10 | 20 | 20 | [0] | 20 | 40 | 0 | 0 | 0 | 0 | 0 |
|   |   | .00039 | 0 | 0 | 0 | 0 | 0 | 0 | 0 | [0] | 0 | 0 | 0 | 0 | 0 | 0 | 0 |
| 5 | POST | .1 | 90 | 100 | 40 | 100 | 100 | 100 | 100 | [50] | 100 | 100 | 50 | 70 | 60 | 90 | 100 |
|   |   | .025 | 30 | 90 | 0 | 90 | 100 | 100 | 100 | [40] | 100 | 100 | 40 | 40 | 50 | 80 | 60 |

-continued

| Compound No. | TYPE | kg/ha | ZEAMX | GLXMX | GOSHI | TRZAW | ORYSA | SORBI | ECHOR | BROJA (SETVI) [AGRSMI] | DIGSA | PANDI | SOLNI | AESIN | ABUTH | XANSI | CAGHE |
|---|---|---|---|---|---|---|---|---|---|---|---|---|---|---|---|---|---|
| 6 | PRE | .006 | 10 | 60 | 0 | 30 | 60 | 60 | 70 | [0] | 30 | 90 | 0 | 20 | 0 | 70 | 30 |
|  |  | .00156 | 0 | 40 | 0 | 0 | 0 | 0 | 0 | [0] | 0 | 60 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
|  | POST | .1 | 100 | 100 | 100 | 100 | 100 | 100 | 100 | [100] | 100 | 100 | 70 | 100 | 100 | 100 | 100 |
|  |  | .025 | 100 | 100 | 100 | 100 | 100 | 100 | 100 | [100] | 100 | 100 | 60 | 30 | 100 | 100 | 100 |
|  |  | .00625 | 100 | 60 | 70 | 70 | 100 | 100 | 100 | [60] | 100 | 100 | 40 | 0 | 50 | 90 | 80 |
|  |  | .001562 | 40 | 30 | 40 | 30 | 70 | 90 | 60 | [0] | 80 | 100 | 0 | 0 | 0 | 30 | 30 |
|  |  | .00039 | 0 | 0 | 0 | 0 | 0 | 0 | 0 | [0] | 0 | 0 | 20 | 0 | 0 | 0 | 0 |
| 9 | PRE | .1 | 100 | 100 | 90 | 100 | 100 | 100 | 100 | [100] | 100 | 100 | 100 | 100 | 100 | 100 | 100 |
|  |  | .025 | 100 | 100 | 80 | 100 | 100 | 100 | 100 | [100] | 100 | 100 | 50 | 60 | 80 | 100 | 100 |
|  |  | .00625 | 100 | 100 | 70 | 90 | 100 | 100 | 100 | [70] | 100 | 100 | 30 | 0 | 70 | 100 | 60 |
|  |  | .001562 | 40 | 80 | 40 | 30 | 60 | 80 | 80 | [30] | 60 | 90 | 0 | 0 | 0 | 60 | 50 |
|  |  | .00039 | 0 | 30 | 0 | 0 | 0 | 60 | 40 | [0] | 0 | 60 | 0 | 0 | 0 | 0 | 20 |
|  | POST | .1 | 100 | 100 | 80 | 100 | 100 | 100 | 100 | [80] | 100 | 100 | 70 | 20 | 60 | 70 | 100 |
|  |  | .025 | 50 | 70 | 50 | 60 | 100 | 90 | 100 | [40] | 100 | 100 | 40 | 0 | 30 | 65 | 60 |
|  |  | .00625 | 40 | 40 | 20 | 30 | 60 | 60 | 70 | [0] | 30 | 40 | 20 | 0 | 0 | 40 | 30 |
|  |  | .001562 | 0 | 0 | 0 | 0 | 40 | 0 | 20 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
| 10 | PRE | .1 | 70 | 100 | 80 | 100 | 100 | 100 | 100 | [100] | 100 | 100 | 100 | 65 | 60 | 90 | 80 |
|  |  | .025 | 20 | 70 | 40 | 40 | 60 | 60 | 70 | [80] | 100 | 80 | 100 | 40 | 30 | 80 | 90 |
|  |  | .00625 | 0 | 40 | 30 | 20 | 20 | 50 | 50 | [30] | 40 | 80 | 30 | 0 | 0 | 40 | 30 |
|  |  | .001562 | 0 | 0 | 0 | 0 | 0 | 20 | 20 | [0] | 0 | 30 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
|  | POST | .1 | 70 | 0 | 40 | 20 | 100 | 100 | 70 | [30] | 65 | 80 | 20 | 0 | 30 | 30 | 50 |
|  |  | .025 | 20 | 0 | 30 | 0 | 60 | 60 | 20 | [0] | 20 | 60 | 0 | 0 | 0 | 0 | 0 |
|  |  | .00625 | 0 | 0 | 0 | 0 | 20 | 0 | 0 | [0] | 0 | 0 | 0 | 0 | 0 | 0 | 0 |
|  |  | .001562 | 0 | 0 | 0 | 0 | 0 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
| 11 | PRE | .1 | 50 | 50 | 40 | 30 | 90 | 100 | 60 | [30] | 30 | 100 | 0 | 40 | 0 | 50 | 50 |
|  |  | .025 | 40 | 40 | 30 | 0 | 50 | 70 | 40 | [0] | 0 | 0 | 0 | 0 | 0 | 20 | 40 |
|  |  | .00625 | 0 | 0 | 0 | 0 | 0 | 0 | 0 | [0] | 0 | 0 | 0 | 0 | 0 | 0 | 0 |
|  |  | .001562 | 0 | 0 | 0 | 0 | 0 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
|  | POST | .1 | 0 | 70 | 60 | 40 | 100 | 70 | 60 | [60] | 80 | 100 | 20 | 20 | 70 | 80 | 70 |
|  |  | .025 | 0 | 10 | 30 | 0 | 65 | 20 | 40 | [0] | 40 | 50 | 0 | 0 | 0 | 30 | 20 |
|  |  | .00625 | 0 | 0 | 0 | 0 | 20 | 0 | 0 | [0] | 30 | 0 | 0 | 0 | 0 | 0 | 0 |
|  |  | .001562 | 0 | 0 | 0 | 0 | 0 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
|  | POST | .1 | 0 | 100 | 60 | 40 | 90 | 50 | 100 | [50] | 80 | 70 | 0 | 70 | 50 | 100 | 50 |
|  |  | .025 | 0 | 50 | 30 | 10 | 40 | 0 | 30 | [0] | 30 | 0 | 0 | 20 | 0 | 60 | 40 |
|  |  | .00625 | 0 | 0 | 0 | 0 | 0 | 0 | 0 | [0] | 0 | 0 | 0 | 0 | 0 | 0 | 0 |
|  |  | .001562 | 0 | 0 | 0 | 0 | 0 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
| 12 | PRE | .1 | 100 | 100 | 100 | 70 | 100 | 100 | 100 | [80] | 100 | 100 | 100 | 70 | 100 | 100 | 100 |
|  |  | .025 | 70 | 50 | 50 | 30 | 100 | 90 | 80 | [30] | 50 | 100 | 30 | 10 | 40 | 80 | 65 |
|  |  | .00625 | 20 | 0 | 0 | 0 | 90 | 30 | 20 | [0] | 20 | 70 | 0 | 0 | 0 | 20 | 20 |

-continued

PRIMARY SCREENING (Herbicide)

| Compound No. | TYPE | kg/ha | ZEAMX | GLXMX | GOSHI | TRZAW | ORYSA | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|---|---|---|---|---|
|  | POST | .001562 | 0 | 0 | 0 | 0 | 20 | 0 | 0 | [0] | 0 | 20 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
| 14 | PRE | .1 | 100 | 100 | 80 | 100 | 100 | 100 | 100 | [80] | 100 | 100 | 60 | 90 | 70 | 100 | 100 |
|  |  | .025 | 100 | 90 | 60 | 30 | 100 | 100 | 100 | [20] | 40 | 100 | 30 | 70 | 40 | 70 | 40 |
|  |  | .00625 | 20 | 50 | 20 | 0 | 70 | 30 | 20 | [0] | 0 | 30 | 0 | 30 | 0 | 40 | 0 |
|  |  | .001562 | 0 | 0 | 0 | 0 | 0 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
|  | POST | .1 | 100 | 100 | 90 | 100 | 100 | 100 | 100 | [100] | 100 | 100 | 70 | 80 | 100 | 100 | 100 |
|  |  | .025 | 20 | 90 | 80 | 100 | 100 | 100 | 100 | [70] | 100 | 100 | 40 | 50 | 70 | 90 | 100 |
|  |  | .00625 | 0 | 60 | 50 | 50 | 50 | 50 | 70 | [30] | 60 | 80 | 0 | 0 | 50 | 80 | 70 |
|  |  | .00156 | 0 | 20 | 0 | 0 | 0 | 0 | 40 | [0] | 0 | 0 | 0 | 0 | 0 | 30 | 30 |
|  |  | .00039 | 0 | 0 | 0 | 0 | 0 | 0 | 0 | [0] | 0 | 0 | 0 | 0 | 0 | 0 | 0 |
| 15 | PRE | .1 | 90 | 100 | 60 | 100 | 100 | 100 | 100 | [90] | 100 | 100 | 60 | 100 | 90 | 100 | 100 |
|  |  | .025 | 40 | 80 | 40 | 90 | 90 | 100 | 100 | [60] | 100 | 90 | 50 | 100 | 60 | 100 | 100 |
|  |  | .00625 | 0 | 60 | 0 | 50 | 50 | 100 | 70 | [40] | 40 | 80 | 30 | 40 | 50 | 100 | 40 |
|  |  | .00156 | 0 | 30 | 0 | 20 | 20 | 50 | 50 | [0] | 0 | 60 | 0 | 0 | 0 | 40 | 20 |
|  |  | .00039 | 0 | 0 | 0 | 0 | 0 | 0 | 0 | [0] | 0 | 20 | 0 | 0 | 0 | 0 | 0 |
|  | POST | .1 | 40 | 100 | 70 | 70 | 100 | 100 | 100 | [60] | 100 | 100 | 70 | 40 | 60 | 80 | 100 |
|  |  | .025 | 0 | 60 | 40 | 50 | 100 | 80 | 80 | [0] | 100 | 80 | 0 | 0 | 20 | 50 | 100 |
|  |  | .00625 | 0 | 20 | 0 | 30 | 40 | 0 | 20 | [0] | 50 | 20 | 0 | 0 | 0 | 0 | 50 |
|  |  | .00156 | 0 | 0 | 0 | 0 | 0 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
| 16 | PRE | .1 | 10 | 100 | 60 | 70 | 100 | 70 | 100 | [70] | 100 | 100 | 0 | 80 | 0 | 90 | 60 |
|  |  | .025 | 0 | 90 | 50 | 50 | 90 | 40 | 90 | [30] | 50 | 80 | 0 | 50 | 0 | 80 | 40 |
|  |  | .00625 | 0 | 50 | 0 | 20 | 40 | 0 | 60 | [0] | 0 | 20 | 0 | 20 | 0 | 60 | 30 |
|  |  | .00156 | 0 | 30 | 0 | 0 | 0 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
|  | POST | .1 | 0 | 0 | 0 | 30 | 90 | 90 | 40 | [70] | 40 | 50 | 40 | 40 | 50 | 90 | 60 |
|  |  | .025 | 0 | 0 | 0 | 0 | 30 | 40 | 0 | [30] | 0 | 0 | 0 | 0 | 40 | 60 | 40 |
|  |  | .00625 | 0 | 0 | 0 | 0 | 0 | 0 | 0 | [0] | 0 | 0 | 0 | 0 | 0 | 0 | 30 |
|  |  | .0250 | 0 | 0 | 0 | 0 | 0 | 0 | 0 | [0] | 0 | 0 | 0 | 0 | 0 | 0 | 0 |
|  |  | .001562 | 0 | 0 | 0 | 0 | 0 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
| 17 | PRE | .1 | 40 | 40 | 40 | 40 | 100 | 60 | 90 | [50] | 100 | 30 | 30 | 0 | 0 | 60 | 60 |
|  |  | .025 | 10 | 10 | 20 | 10 | 50 | 30 | 30 | [30] | 40 | 0 | 20 | 0 | 0 | 0 | 0 |
|  |  | .00625 | 0 | 0 | 0 | 0 | 0 | 20 | 20 | [0] | 0 | 0 | 0 | 0 | 0 | 0 | 0 |
|  |  | .00156 | 0 | 0 | 0 | 0 | 0 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
|  | POST | .1 | 0 | 0 | 50 | 60 | 100 | 100 | 100 | [50] | 100 | 100 | 80 | 40 | 40 | 70 | 70 |
|  |  | .025 | 0 | 0 | 20 | 40 | 100 | 60 | 70 | [30] | 40 | 90 | 40 | 0 | 0 | 40 | 40 |
|  |  | .00625 | 20 | 0 | 30 | 30 | 50 | 30 | 20 | [0] | 0 | 40 | 20 | 0 | 0 | 0 | 0 |
|  |  | .00156 | 0 | 0 | 0 | 0 | 20 | 0 | 0 | [0] | 0 | 0 | 0 | 0 | 0 | 0 | 0 |
|  |  | .00039 | 0 | 0 | 0 | 0 | 0 | 0 | 0 | [0] | 0 | 0 | 0 | 0 | 0 | 0 | 0 |
|  | POST | .1 | 20 | 100 | 50 | 60 | 100 | 100 | 100 | [50] | 100 | 100 | 60 | 40 | 30 | 90 | 40 |
|  |  | .025 | 0 | 50 | 30 | 20 | 65 | 60 | 80 | [0] | 50 | 80 | 40 | 0 | 0 | 60 | 20 |
|  |  | .00625 | 0 | 0 | 0 | 0 | 30 | 20 | 60 | [0] | 0 | 0 | 0 | 0 | 0 | 20 | 0 |
|  |  | .00156 | 0 | 0 | 0 | 0 | 0 | 0 | 0 | [0] | 0 | 0 | 0 | 0 | 0 | 0 | 0 |

-continued

PRIMARY SCREENING (Herbicide)

| Compound No. | TYPE | kg/ha | ZEAMX | GLXMX | GOSHI | TRZAW | ORYSA | SORBI | ECHOR | BROJA (SETVI) [AGRSM] | DIGSA | PANDI | SOLNI | AESIN | ABUTH | XANSI | CAGHE |
|---|---|---|---|---|---|---|---|---|---|---|---|---|---|---|---|---|---|
| 19 | PRE | .00039 | 0 | 0 | 0 | 0 | 0 | 0 | 0 | [0] | 0 | 0 | 0 | 0 | 0 | 0 | 0 |
|  |  | .1 | 70 | 65 | 70 | 60 | 100 | 100 | 100 | [80] | 100 | 100 | 80 | 20 | 80 | 100 | 100 |
|  |  | .025 | 10 | 20 | 20 | 30 | 100 | 80 | 70 | [20] | 50 | 100 | 40 | 0 | 40 | 60 | 70 |
|  |  | .00625 | 0 | 0 | 0 | 0 | 70 | 50 | 0 | [0] | 0 | 70 | 0 | 0 | 0 | 40 | 20 |
|  |  | .001562 | 0 | 0 | 0 | 0 | 0 | 0 | 0 | [0] | 0 | 0 | 0 | 0 | 0 | 0 | 0 |
|  | POST | .00039 | 0 | 0 | 0 | 0 | 0 | 0 | 0 | [0] | 0 | 0 | 0 | 0 | 0 | 0 | 0 |
|  |  | .1 | 70 | 100 | 65 | 100 | 100 | 100 | 100 | [80] | 100 | 100 | 70 | 70 | 80 | 100 | 100 |
|  |  | .025 | 20 | 40 | 40 | 40 | 70 | 100 | 90 | [40] | 20 | 90 | 40 | 40 | 30 | 80 | 60 |
|  |  | .00625 | 0 | 0 | 0 | 20 | 30 | 40 | 40 | [0] | 0 | 40 | 30 | 0 | 0 | 0 | 30 |
|  |  | .001562 | 0 | 0 | 0 | 0 | 0 | 0 | 0 | [0] | 0 | 0 | 0 | 0 | 0 | 0 | 0 |
| 20 | PRE | .00039 | 0 | 0 | 0 | 0 | 0 | 0 | 0 | [0] | 0 | 0 | 0 | 0 | 0 | 0 | 0 |
|  |  | .1 | 10 | 40 | 30 | 50 | 100 | 100 | 100 | [70] | 100 | 100 | 60 | 30 | 70 | 100 | 70 |
|  |  | .025 | 0 | 10 | 0 | 30 | 80 | 20 | 20 | [20] | 30 | 30 | 0 | 0 | 10 | 100 | 50 |
|  |  | .00625 | 0 | 0 | 0 | 0 | 40 | 0 | 0 | [0] | 0 | 0 | 0 | 0 | 0 | 30 | 0 |
|  |  | .001562 | 0 | 0 | 0 | 0 | 0 | 0 | 0 | [0] | 0 | 0 | 0 | 0 | 0 | 0 | 0 |
|  | POST | .00039 | 0 | 0 | 0 | 0 | 0 | 0 | 0 | [0] | 0 | 0 | 0 | 0 | 0 | 0 | 0 |
|  |  | .1 | 0 | 70 | 50 | 60 | 100 | 90 | 100 | [50] | 50 | 60 | 30 | 70 | 30 | 90 | 70 |
|  |  | .025 | 0 | 40 | 30 | 20 | 40 | 40 | 50 | [0] | 0 | 0 | 0 | 20 | 0 | 40 | 40 |
|  |  | .00625 | 0 | 0 | 0 | 0 | 0 | 0 | 0 | [0] | 0 | 0 | 0 | 0 | 0 | 0 | 0 |
|  |  | .001562 | 0 | 0 | 0 | 0 | 0 | 0 | 0 | [0] | 0 | 0 | 0 | 0 | 0 | 0 | 0 |
| 22 | PRE | .00039 | 0 | 0 | 0 | 0 | 0 | 0 | 0 | [0] | 0 | 0 | 0 | 0 | 0 | 0 | 0 |
|  |  | .1 | 100 | 100 | 100 | 20 | 100 | 100 | 100 | [40] | 100 | 100 | 70 | 100 | 100 | 100 | 100 |
|  |  | .025 | 100 | 100 | 80 | 0 | 100 | 100 | 100 | [30] | 90 | 90 | 60 | 60 | 80 | 70 | 100 |
|  |  | .00625 | 90 | 50 | 40 | 0 | 60 | 80 | 80 | [0] | 50 | 60 | 20 | 20 | 70 | 30 | 30 |
|  |  | .001562 | 30 | 40 | 0 | 0 | 40 | 30 | 20 | [0] | 0 | 20 | 0 | 0 | 0 | 20 | 20 |
|  |  | .00039 | 0 | 20 | 0 | 0 | 20 | 0 | 0 | [0] | 0 | 0 | 0 | 0 | 0 | 0 | 0 |
|  | POST | .1 | 100 | 100 | 100 | 60 | 100 | 100 | 100 | [50] | 100 | 100 | 100 | 100 | 100 | 100 | 100 |
|  |  | .0025 | 100 | 100 | 80 | 10 | 50 | 100 | 100 | [30] | 80 | 100 | 50 | 40 | 70 | 100 | 50 |
|  |  | .00625 | 70 | 70 | 40 | 0 | 30 | 60 | 40 | [0] | 40 | 40 | 40 | 30 | 60 | 60 | 40 |
|  |  | .001562 | 20 | 40 | 0 | 0 | 0 | 20 | 0 | [0] | 0 | 0 | 30 | 0 | 0 | 20 | 30 |
|  |  | .00039 | 0 | 0 | 0 | 0 | 0 | 0 | 0 | [0] | 0 | 0 | 0 | 0 | 0 | 0 | 0 |

| | | | PRIMARY SCREENING (PADDY SUBMERGED)-HERBICIDE | | | | | | |
|---|---|---|---|---|---|---|---|---|---|
| Compound no. | DAT | kg/ha | ORYSA (3Leaf) | ORYSA (seed) | ECHOR | SCPJU | MOOVA | CYPSE | SAGPY |
| 1 | 2 | .05 | 100 | 100 | 100 | 80 | 90 | 100 | 70 |
|   |   | .1 | 100 | 100 | 100 | 100 | 100 |   | 100 |
|   |   | 0.25 | 100 | 100 | 100 | 100 | 100 |   | 90 |
|   |   | .006 | 90 | 90 | 100 | 50 | 90 |   | 80 |
|   |   | .0015 | 10 | 10 | 100 | 0 | 70 |   | 70 |
|   |   | .0004 | 0 | 0 | 20 | 0 | 30 |   | 50 |
| 2 | 2 | .05 | 40 | 40 | 50 | 20 | 60 |   | 60 |
| 3 | 2 | .05 | 40 | 0 | 20 | 0 | 0 | 40 | 50 |
| 4 | 2 | .05 | 90 | 70 | 80 | 60 | 90 | 80 | 80 |
| 5 | 2 | .05 | 60 | 70 | 60 | 0 | 80 | 80 | 80 |
| 6 | 2 | 4 | 100 | 100 | 100 | 100 | 100 | 100 | 100 |
|   |   | .05 | 100 | 100 | 90 | 100 | 100 | 100 | 100 |
|   |   | .025 | 100 | 100 | 90 | 90 | 90 | 100 | 100 |
|   |   | .0125 | 100 | 100 | 80 | 70 | 70 | 100 | 100 |
|   |   | .0062 | 60 | 50 | 0 | 0 | 0 | 100 | 100 |
|   |   | .003 | 20 | 0 | 0 | 0 | 0 | 0 | 20 |
| 7 | 2 | 4 | 100 | 100 | 100 | 100 | 100 | 100 | 100 |
|   |   | 4 | 100 | 100 | 100 | 100 | 100 | 100 | 100 |
|   |   | 1 | 100 | 100 | 90 | 100 | 100 | 100 | 100 |
|   |   | .25 | 100 | 100 | 90 | 100 | 100 | 100 | 100 |
|   |   | .06 | 100 | 100 | 80 | 100 | 100 | 100 | 100 |
|   |   | .015 | 100 | 90 | 80 | 100 | 100 | 100 | 100 |
|   |   | .05 | 100 | 100 | 70 | 0 | 50 | 80 | 100 |
|   |   | .025 | 50 | 40 | 40 | 0 | 0 | 30 | 100 |
|   |   | .0125 | 40 | 30 | X | 0 | 0 | 50 | 30 |
|   |   | .0062 | 30 | X | 0 | 0 | 0 | X | 0 |
|   |   | .003 | 0 | 0 | 0 | 0 | 0 | 0 | 0 |
| 8 | 2 | 4 | 100 | 100 | 100 | 100 | 100 | 100 | 100 |
|   |   | 4 | 100 | 100 | 100 | 100 | 100 | 100 | 100 |
|   |   | 1 | 100 | 90 | 80 | 50 | 90 | 100 | 100 |
|   |   | .25 | 100 | 80 | 50 | 20 | 50 | 80 | 90 |
|   |   | .06 | 80 | 60 | 20 | 0 | 0 | X | 70 |
|   |   | .015 | 0 | 0 | 0 | 0 | 0 | 0 | 0 |
| 9 | 2 | 4 | 100 | 100 | 100 | 100 | 100 | 100 | 100 |
|   |   | .05 | 100 | 100 | 70 | 50 | 80 | 100 | 100 |
|   |   | .025 | 40 | 60 | 30 | 0 | 30 | 100 | 100 |
|   |   | .0125 | 0 | 0 | 0 | 0 | 0 | 0 | 0 |
|   |   | .0062 | 0 | 0 | 0 | 0 | 0 | 0 | 0 |
|   |   | .003 | 0 | 0 | 0 | 0 | 0 | 0 | 0 |
|   | 3 | .05 | 80 | 90 | 90 | 60 | 80 | 100 | 100 |
|   |   | .0125 | 0 | 0 | 0 | 0 | 0 | 0 | 0 |
|   |   | .003 | 0 | 0 | 0 | 0 | 0 | 0 | 0 |
|   |   | .00078 | 0 | 0 | 0 | 0 | 0 | 0 | 0 |
|   |   | .0002 | 0 | 0 | 0 | 0 | 0 | 0 | 0 |
|   |   | .05 | 50 | 50 | 70 | 0 | 0 | 30 | 0 |
|   |   | .0125 | 0 | 20 | 0 | 0 | 0 | 0 | 0 |
|   |   | .00312 | 0 | 0 | 0 | 0 | 0 | 0 | 0 |
|   |   | .00078 | 0 | 0 | 0 | 0 | 0 | 0 | 0 |
|   |   | .0002 | 0 | 0 | 0 | 0 | 0 | 0 | 0 |
| 10 | 2 | 4 | 100 | 100 | 100 | 100 | 100 | 100 | 100 |
| 11 | 2 | .05 | 70 | 60 | 70 | 20 | 50 | 70 | 90 |
| 12 | 2 | .05 | 90 | 90 | 90 | 90 | 90 | 90 | 90 |
|   |   | .05 | 100 | 100 | 100 | 100 | 100 | 100 | 100 |
|   |   | .025 | 100 | 100 | 100 | 100 | 100 | 100 | 100 |
|   |   | .0125 | 100 | 100 | 100 | 100 | 100 | 100 | 100 |
|   |   | .006 | 100 | 100 | 70 | 100 | 100 | 100 | 100 |
|   |   | .003 | 80 | 90 | 50 | 70 | 100 | 100 | 100 |
|   | 3 | .05 | 100 | 100 | 100 | 95 | 90 | 100 | 100 |
|   |   | .0125 | 40 | 70 | 40 | 60 | 50 | 70 | 100 |
|   |   | .003 | 0 | 0 | 0 | 0 | 0 | 0 | 0 |
|   |   | .00078 | 0 | 0 | 0 | 0 | 0 | 0 | 0 |
|   |   | .0002 | 0 | 0 | 0 | 0 | 0 | 0 | 0 |
| 13 | 2 | .05 | 70 | 70 | 60 | 50 | 50 | 80 | 70 |
| 14 | 2 | 4 | 100 | 100 | 100 | 100 | 100 | 100 | 100 |
| 15 | 2 | 4 | 100 | 10 | 100 | 100 | 100 | 100 | 100 |
| 16 | 2 | 4 | 100 | 100 | 100 | 100 | 100 | 100 | 100 |
| 17 | 2 | 4 | 100 | 100 | 100 | 100 | 100 | 100 | 100 |
| 19 | 2 | .05 | 80 | 90 | 80 | 90 | 80 | 80 | 80 |
|   |   | .05 | 100 | 100 | 100 | 80 | 100 | 100 | 100 |
|   |   | .025 | 100 | 100 | 90 | 60 | 100 | 100 | 100 |
|   |   | .0125 | 90 | 100 | 70 | 60 | 100 | 100 | 100 |
|   |   | .006 | 90 | 70 | 40 | 30 | 100 | 80 | 90 |
|   |   | .003 | 60 | 60 | 0 | 0 | 100 | 60 | 70 |
| 20 | 2 | .05 | 80 | 70 | 60 | 40 | 40 | 60 | 70 |

| Compound no. | DAT | kg/ha | ORYSA (3Leaf) | ORYSA (seed) | ECHOR | SCPJU | MOOVA | CYPSE | SAGPY |
|---|---|---|---|---|---|---|---|---|---|
| 21 | 2 | .05 | 70 | 60 | 60 | 20 | 30 | 60 | 60 |
| 22 | 3 | .05 | 60 | 60 | 60 | 90 | 90 | 100 | 90 |
|  | 2 | .05 | 0 | 0 | 0 | 40 | 0 | 80 | 100 |
|  |  | .0125 | 0 | 0 | 0 | 0 | 0 | 0 | 0 |
|  |  | .00312 | 0 | 0 | 0 | 0 | 0 | 0 | 0 |
|  |  | .00078 | 0 | 0 | 0 | 0 | 0 | 0 | 0 |
|  |  | .00019 | 0 | 0 | 0 | 0 | 0 | 0 | 0 |
| 23 | 3 | .05 | 50 | 50 | 20 | 70 | 80 | 100 | 90 |
| 24 | 3 | .05 | 0 | 0 | 40 | 0 | 0 | 0 | 0 |
| 25 | 3 | .05 | 20 | 20 | 20 | 0 | 0 | 40 | 50 |
| 26 | 3 | .05 | 0 | 10 | 0 | 0 | 0 | 50 | 60 |

-continued

PRIMARY SCREENING (PADDY SUBMERGED)-HERBICIDE

What is claimed is:

1. Compounds of pyridine sulfonyl urea derivatives having the structure of the following formula(I)

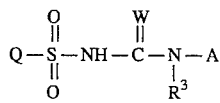

wherein,

Q is Q-1, Q-2, Q-3 or Q-4 as follows;

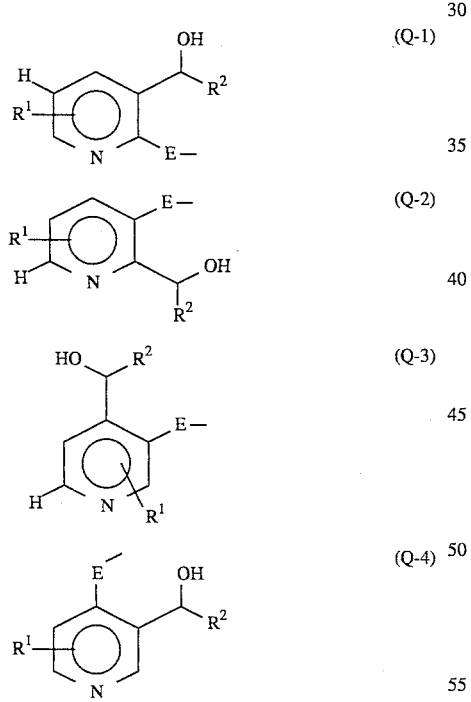

E is single bond or $CH_2$;

$R^1$ is H, $C_1$–$C_3$ alkyl, $C_1$–$C_3$ haloalkyl, halogen, CN, $NO_2$, $C_1$–$C_3$ alkoxy, $C_1$–$C_3$ haloalkoxy, $SO_2NR'R''$, $C_1$–$C_3$ alkylthio, $C_1$–$C_3$ alkylsulfinyl, $C_1$–$C_3$ alkylsulfonyl, $SCH_2F$, $NH_2$, $NHCH_3$, $N(CH_3)_2$, $C_1$–$C_2$ alkyl substituted with $C_1$–$C_2$ alkoxy, $C_1$–$C_2$ haloalkoxy, SH, $SCH_3$, CN or OH or $CO_2R'''$; and then $R'$ is H, $C_1$–$C_4$ alkyl, $C_2$–$C_3$ cyanoalkyl, methoxy or ethoxy; $R''$ is H, $C_1$–$C_4$ alkyl, $C_3$–$C_4$ alkenyl, or when taken together, connecting $R'$ and $R''$, $-(CH_2)_3-$, $-(CH_2)_4-$, $-(CH_2)_5-$ or $CH_2CH_2OCH_2CH_2-$, may be formed;

$R'''$ is $C_1$–$C_4$ alkyl, $C_3$–$C_4$ alkenyl, $C_3$–$C_4$ alkynyl, $C_1$–$C_4$ alkyl substituted with 1–2 halogen or cyano groups, $C_5$–$C_6$, cycloalkyl, $C_3$–$C_7$ cycloalkylalkyl or $C_2$–$C_4$ alkoxyalkyl;

$R^2$ is $C_1$–$C_6$ alkyl substituted with 1–3 halogens;

$R^3$ is H or $CH_3$;

W is O or S;

A is

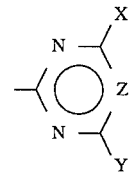

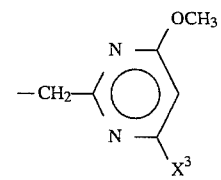

wherein,

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$ alkyl) amino or $C_3$–$C_5$ cycloalkyl;

Y is H, $C_1$–$C_4$ alkyl, $C_1$–$C_4$ alkoxy, $C_1$–$C_4$ haloalkoxy, $C_1$–$C_4$ haloakylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_2$–$C_5$ alkylthioalkyl, $C_1$–$C_4$ haloalkyl, $C_2$–$C_4$ alkynyl, azido, cyano, $C_2$–$C_5$ alkylsulfinylalkyl, $C_2$–$C_5$ alkylsulfonylalkyl, $CH_2OH$, $C_3$–$C_5$ cycloalkyl,

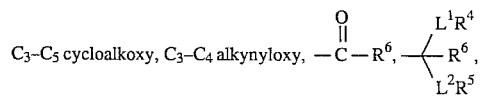

-continued

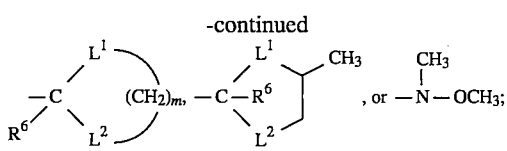

m is 2 or 3,
$L^1$ and $L^2$ are independently O or S;
$R^4$ and $R^5$ are independently $C_1-C_2$ alkyl;
$R^6$ is H or $CH_3$;
Z is CH;
$X^3$ is $CH_3$ or $OCH_3$;
or the agriculturally suitable salts thereof.

2. A compound as defined in the claim 1, wherein E is single bond, W is O, and $R^3$ is H.

3. A compound as defined in claim 1, wherein $R^1$ is selected from the group consisting of H, halogen, $C_1-C_2$ alkyl, $C_1-C_2$ alkoxy, $C_1-C_2$ haloalkyl, $C_1-C_2$ alkylthio, haloalkoxy and $CH_2CN$; X is selected from the group consisting of $C_1-C_2$ alkyl, $C_1-C_2$ alkoxy, Cl, F, Br, I, $OCHF_2$, $CH_2F$, $CF_3$, $OCH_2CH_2F$, $OCH_2CHF_2$, $OCH_2CF_3$, $CH_2Cl$ and $CH_2Br$; and Y is H, $C_1-C_2$ alkyl, $C_1-C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OC_2H_5$, $OCH_2CH_2OCH_3$, $CH_2SCH_3$,

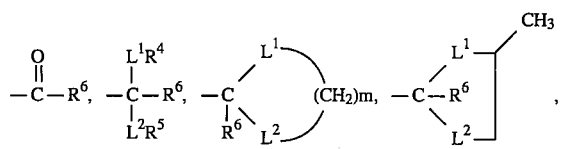

$OCHF_2$, $OCF_2Br$, $SCHF_2$, cyclopropyl, $C\equiv CH$ or $C\equiv C-CH_3$, and then $R^4$ and $R^5$ are $C_1-C_2$ alkyl, $R^6$ is H or $CH_3$, $L^1$ and $L^2$ are O or S and m is 2 or 3.

4. A compound as defined in the claim 1, wherein Q is Q-1 or Q-2; Z is CH; X is $CH_3$, $C_2H_5$, $OCH_3$, $OCH_2CH_3$, Cl or $OCHF_2$; Y is $CH_3$, $OCH_3$, $OC_2H_5$, $C_2H_5$, $CH_2OCH_3$, $NHCH_3$, $CH(OCH_3)_2$ or cyclopropyl.

5. A compound as defined in the claim 1, wherein $R^2$ is $CH_2F$, $CH_2CH_2F$, $CHF-CH_3$, $CH_2Cl$, $CH_2Br$, $CHCl_2$, $CHFCl$, $CH_2CH_2Cl$, $CHClCH_3$, $CHF_2$, $CHCl-CH_2Cl$, $CHFCH_2Cl$, $CHF-CH_2F$ or $CH_2CHF_2$.

6. A compound as defined in claim 1, wherein said general formula(I) is N-[ (4,6-dimethoxypyrimidin-2-yl)aminocarbonyl]-3-(2-fluoro-1-hydroxyethyl)-2-pyridinesulfonamide.

7. A compound as defined in claim 1, wherein said general formula(I) is 3-(2 -fluoro-1-hydroxyethyl)-N-[(4-methoxy-6-methyl-pyrimidin-2 -yl)aminocarbonyl]-2-pyridinesulfonamide.

8. A compound as defined in claim 1, wherein said general formula(I) is N-[(4 -chloro-6-methoxy-pyrimidin-2-yl)aminocarbonyl]-3-(2-fluoro-1 -hydroxyethyl)-2-pyridinesulfonamide.

9. A compound as defined in claim 1, wherein said general formula(I) is N-[ (4,6-dimethyl-pyrimidin-2-yl)aminocarbonyl]-3-(2-fluoro-1-hydroxyethyl)- 2-pyridinesulfonamide.

10. A compound as defined in claim 1, wherein said general formula(I) is N-[(4-chloro-6-ethoxy-pyrimidin-2-yl)aminocarbonyl]-3-(2-fluoro-1-hydroxyethyl)- 2-pyridinesulfonamide.

11. A compound as defined in claim 1, wherein said general formula(I) is N-[(4,6-dimethoxy-pyrimidin-2-yl)amino carbonyl]-2-(2-fluoro-1-hydroxyethyl)- 3-pyridinesulfonamide.

12. A compound as defined in claim 1, wherein said general formula(I) is 3-(2-fluoro-1-hydroxypropyl)-N-[ (4-methyl-6-methoxy-pyrimidin-2-yl) aminocarbonyl] -2-pyridinesulfonamide.

13. A compound as defined in claim 1, wherein said general formula(I) is N-[ (4,6-dimethyl-pyrimidin-2-yl)aminocarbonyl]-3-(2-fluoro-1 -hydroxypropyl)-2-pyridinesulfonamide.

14. A compound as defined in claim 1, wherein said general formula(I) is N-[(4 -chloro-6-methoxy-pyrimidin-2-yl)amino carbonyl]-3-(-2-fluoro-1 -hydroxypropyl)-2-pyridinesulfonamide.

15. A compound as defined in claim 1, wherein said general formula(I) is N-[ (4,6-dimethoxy-pyrimidin-2-yl)aminocarbonyl]-3-(2-chloro-1 -hydroxyethyl)-2-pyridinesulfonamide.

16. A compound as defined in claim 1, wherein said general formula(I) is 3-(2 -chloro-1-hydroxyethyl)-N-[(4-methoxy-6-methyl-pyrimidin-2-yl) aminocarbonyl]-2-pyridinesulfonamide.

17. A compound as defined in claim 1, wherein said general formula(I) is 3-(2 -chloro-1-hydroxyethyl)-N-[(4,6-dimethyl-pyrimidin-2-yl)aminocarbonyl]-2-pyridine-sulfonamide.

18. A compound as defined in claim 1, wherein said general formula(I) is N-[(4-chloro-6-methoxy-pyrimidin-2-yl)aminocarbonyl]-3-(2-chloro-1 -hydroxyethyl)-2-pyridinesulfonamide.

19. A compound as defined in claim 1, wherein said general formula(I) is 3-(2 -fluoro-1-hydroxybutyl)-N-[ (4-methoxy-6-methyl-pyrimidin-2-yl) aminocarbonyl]-2-pyridinesulfonamide.

20. A compound as defined in claim 1, wherein said general formula(I) is N-[ (4,6-dimethoxy-pyrimidin-2-yl)aminocarbonyl]-3-(2-fluoro-1-hydroxybutyl)-2-pyridinesulfonamide.

21. A compound as defined in claim 1, wherein said general formula(I) is 3-(2 -chloro-1-hydroxypropyl)-N-[(4, 6-dimethoxy-pyrimidin-2-yl) aminocarbonyl]-2-pyridinesulfonamide.

22. A compound as defined in claim 1, wherein said general formula(I) is N-[(4- 6-dimethoxy-pyrimidin-2-yl)aminocarbonyl]-3-(2-fluoro-1-hydroxypropyl)- 2-pyridinesulfonamide.

23. A compound as defined in claim 1, wherein said general formula(I) is 3-(2 -chloro-1-hydroxyethyl)-N-[(4-chloro-6-ethoxy-pyrimidin-2 -yl)aminocarbonyl]-2-pyridinesulfonamide.

24. A compound as defined in claim 1, wherein said general formula(I) is N-[(4-chloro-6-ethoxy-pyrimidin-2-yl)aminocarbonyl]-2-(2-fluoro-1 -hydroxyethyl)-3-pyridinesulfonamide.

25. A compound as defined in claim 1, wherein said general formula(I) is 3-(2 -chloro-hydroxypropyl)-N-[(4-methoxy-6-methyl-pyrimidin-2 -yl)aminocarbonyl]-2-pyridinesulfonamide.

26. A compound as defined in claim 1, wherein said general formula(I) is N-[(4-chloro-6-methoxy-pyrimidin-2-yl)aminocarbonyl] -2-(2-fluoro-1 -hydroxyethyl)-3-pyridinesulfonamide.

27. A compound as defined in claim 1, wherein said general formula(I) is N-[ (4,6-dimethoxy-pyrimidin-2-yl)aminocarbonyl]-2-(2-fluoro-1 -hydroxypropyl)-3-pyridinesulfonamide.

28. Compounds as defined in claim 1, wherein said general formula(I) is 2-(2-fluoro-1-hydroxyethyl)-N-[(4-methoxy-6-methyl-pyrimidin-2 -yl)aminocarbonyl]-3-pyridinesulfonamide.

29. Compounds as defined in claim 1, wherein said general formula(I) is N-[ (4,6-dimethyl-pyrimidin-2-yl)aminocarbonyl]-2-(2-fluoro-1-hydroxyethyl)- 3-pyridinesulfonamide.

30. Compounds as defined in the claim 1, wherein, $R^1$ is H; $R^2$ is $CH_2F$, $CH_2Cl$, $CHF_2$, $CHFCH_3$ or $CH_2CH_2F$; $R^3$ is H; A is $A_1$; and W is O.

31. Intermediate compounds of the formula(I) in the claim 1 having the following formula(II)

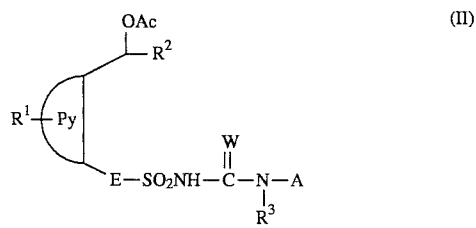 (II)

wherein $R^1$, $R^2$, $R^3$, E, W and A are respectively as defined in claim 1; Ac is acetyl group or protected group regenerating hydroxy group by separating under the condition of acid or alkali;

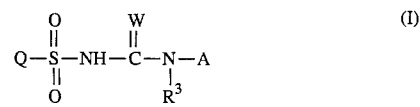

with the proviso that $R^1$ is not a para substituent of sulfonyl urea.

32. A method for controlling weeds by which effective amount of one or more of the following formula (I) of pyridine sulfonyl urea derivatives in weedy area at preemergence or post emergence

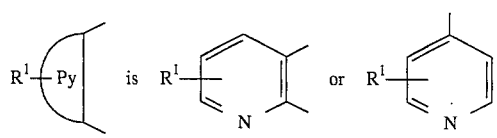 (I)

wherein O, W, $R^3$ and A are respectively as defined in claim 1.

33. A herbicidal composition comprising one or more components selected from formula I of claim 1 in combination with an inert carrier.

* * * * *